(12) United States Patent
Holtzapple et al.

(10) Patent No.: US 7,705,116 B2
(45) Date of Patent: *Apr. 27, 2010

(54) METHOD AND SYSTEM FOR SOLUBILIZING PROTEIN

(75) Inventors: Mark Thomas Holtzapple, College Station, TX (US); Gary P. Noyes, Houston, TX (US); Richard Davison, Bryan, TX (US); Cesar B. Granda, College Station, TX (US)

(73) Assignees: Texas A&M University System, College Station, TX (US); Terrabon Technology Corp., Bryan, TX (US)

( * ) Notice: Subject to any disclaimer, the term of this patent is extended or adjusted under 35 U.S.C. 154(b) by 115 days.

This patent is subject to a terminal disclaimer.

(21) Appl. No.: 11/142,622

(22) Filed: Jun. 1, 2005

(65) Prior Publication Data

US 2006/0069244 A1 Mar. 30, 2006

Related U.S. Application Data

(63) Continuation-in-part of application No. 10/703,985, filed on Nov. 7, 2003.

(60) Provisional application No. 60/424,668, filed on Nov. 7, 2002, provisional application No. 60/576,180, filed on Jun. 1, 2004.

(51) Int. Cl.
*A61K 38/00* (2006.01)
(52) U.S. Cl. .......................................... 530/300; 514/2
(58) Field of Classification Search ........................ None
See application file for complete search history.

(56) References Cited

U.S. PATENT DOCUMENTS

| 2,456,297 | A | * | 12/1948 | Melnick ..................... 435/68.1 |
| 2,694,666 | A | * | 11/1954 | Parfentjev ................... 530/305 |
| 2,991,309 | A | * | 7/1961 | Hoglan et al. ............... 562/516 |
| 3,617,313 | A | | 11/1971 | Harrington, Jr. et al. .. 99/235 R |
| 3,806,501 | A | | 4/1974 | Rymer et al. ............. 260/123.7 |
| 3,846,397 | A | | 11/1974 | Ernster .................... 260/112 R |
| 4,100,154 | A | | 7/1978 | Holloway ................ 260/123.7 |
| 5,008,375 | A | | 4/1991 | Fosbol et al. ................. 530/357 |
| 5,658,605 | A | | 8/1997 | Soeda et al. ..................... 426/7 |
| 5,693,296 | A | | 12/1997 | Holtzapple et al. .......... 423/165 |
| 5,772,968 | A | | 6/1998 | Wolfe ......................... 422/189 |
| 5,780,288 | A | * | 7/1998 | Rohwer ....................... 435/238 |
| 5,865,898 | A | | 2/1999 | Holtzapple et al. ............ 127/37 |
| 6,168,803 | B1 | | 1/2001 | Harris et al. ................. 424/442 |

FOREIGN PATENT DOCUMENTS

| DE | 41 04 174 A1 | 8/1992 |
| FR | 2 065 014 | 7/1971 |
| WO | 8911797 | 12/1989 |
| WO | 2004043159 | 5/2004 |

OTHER PUBLICATIONS

PCT International Search Report with Written Opinion, PCT/US2005/019497, 11 pages, Mailing Date Oct. 12, 2005.
International Search Report for International Application No. PCT/US03/35993 (8 pages), Apr. 1, 2004.
Database WPI, Section Ch, Week 200223, Derwent Publications Ltd., London, GB; XP002274371 & KR 2001 089 928 A (Shin Y H), (abstract), Oct. 17, 2001.
Database WPI, Section Ch, Week 199638, Derwent Publications Ltd., London, GB; XP002274372 & JP 08 183679 A (Hokuyu Kogyo KK), (abstract), Jul. 16, 1996.
Playne "Increased Digestibility of Bagasse by Pretreatment with Alkalis and Steam Explosion"; Biotechnology and Bioengineering., vol. XXVI, (pp. 426-433), May 1, 1984.
Chinese Office Action for Application No. 200580025496.7, 10 pages, Dec. 5, 2008.
European Office Action; Application No. 03 781 891.1-1221; pp. 2, Apr. 20, 2009.
Chinese Office Action; Application No. 200580025496.7; pp. 5, Jul. 24, 2009.
Jia et al.; "Advances of Research on Prion"; Animal Husbandry & Veterinary Medicine; vol. 34; No. 9; pp. 3, 2002.

* cited by examiner

*Primary Examiner*—Andrew D Kosar
*Assistant Examiner*—Satyanarayana R Gudibande
(74) *Attorney, Agent, or Firm*—Conley Rose, P.C.

(57) ABSTRACT

A process for solubilization of protein including application of an alkali, such as lime, and heating. The process may also involve lime recovery and may be accomplished in a single stage or two stages to separate protein solubilized from labile and recalcitrant sources. Systems and devices for use in such process, including a continuous stirred tank reactor and a plug flow reactor are also involved.

31 Claims, 34 Drawing Sheets

METHOD AND SYSTEM FOR SOLUBILIZING PROTEIN

PRIORITY CLAIM

The present application is a Continuation-in-Part under 35 U.S.C. §120 of U.S. patent applications Ser. No. 10/703,985, titled "Process for Solubilizing Protein", filed Nov. 7, 2003 and published as US 2004/0152881 on Aug. 5, 2004, which claims priority under 35 U.S.C. §119(e) to U.S. Provisional Patent Application Ser. No. 60/424,668, titled "Process for Solubilizing Protein" filed Nov. 7, 2002. The present application also claims priority under 35 U.S.C. §119(e) to U.S. Provisional Patent Application Ser. No. 60/576,180, titled "Method and System for Solubilizing Protein", filed Jun. 1, 2004.

JOINT RESEARCH AGREEMENT

The inventions described herein were made pursuant to a Joint Research Agreement as set forth in 35 U.S.C. §103 (c)(3). The parties to the Joint Research Agreement are Terrabon, Inc. and Texas Engineering Experiment Station, a component of the Texas A&M University System.

FIELD OF THE INVENTION

The present invention relates to a process for solubilizing protein, particularly protein from sources in which protein is not readily solubilized. Some embodiments provide a process for destroying prions in solubilized protein.

BACKGROUND OF THE INVENTION

The growing world population has increased food requirements drastically during the past decades, leading to a bigger demand for protein sources for domesticated animals. The increased population also generates an increasing amount of waste that can be a valuable source for producing animal feed.

Processes for protein solubilization from biological sources are useful in turning protein in waste into valuable protein sources. Accordingly, a number of such process have been previously developed. Some processes function only with easily solubilized proteins. Others have been designed to improve solubilization of protein from sources where protein is not easily solubilized, such as chicken feathers.

Thermo-chemical treatments promote the hydrolysis of protein-rich materials, splitting complex polymers into smaller molecules, improving their digestibility, and generating products that enable animals to meet their needs for maintenance, growth, and production with less total feed.

One previous process for the solubilization of protein in chicken feathers involves steam treatment. In this process feathers are treated with steam to make feather meal. The process increases the solubility or digestibility of protein in the feathers only slightly.

Another previous process involves acid treatment of protein sources. The treatment hydrolyzes amino acids, but conditions are usually so harsh that many amino acids are destroyed. Also the acid conditions encourage the formation of disulfide bonds rather than the destruction of such bonds, which would aid solubility.

Additionally, conditions in previous systems may not be suitable for the destruction of prions in the original protein source.

SUMMARY OF THE INVENTION

The present invention includes a novel process for the solubilization of proteins. The process generally involves supplying an alkali, such as lime, to a biological source to produce a slurry. Protein in the slurry is hydrolyzed to produce a liquid product. The slurry may be heated to assist in hydrolysis. A solid residue may also result. This residue may be subjected to further processes of the present invention.

Some embodiments may also be used to separate high-quality protein for use in monogastric feed from low-quality protein which may be used in ruminant feed.

When some processes are used with plant protein sources, removal of the protein provides the additional benefit of simultaneously increasing the enzymatic digestibility of the plant fiber remaining in the solid residue.

According to one specific embodiment, the invention includes a method of solubilizing protein. The method may include applying an alkali to a protein source to form a slurry; heating the slurry to a temperature sufficient to allow hydrolysis of protein in the protein source to obtain a reaction liquid; separating solids from the reaction liquid; neutralizing the reaction liquid with acid or an acid source to produce a neutralized liquid; concentrating the neutralized liquid to produce concentrated liquid and water; and returning the water to the slurry before or during the heating step.

According to another specific embodiment, the invention includes a system for solubilizing protein. The system may include a heated reactor able to react a protein source and an alkali to produce a reaction liquid. It may also include a solid/liquid separator able to separate solids from the reaction liquid. The system may also have a neutralization tank able to allow addition of acid to the reaction liquid to produce a neutralized liquid and a concentration tank able to concentrate neutralized liquid and to produce a concentrated liquid and water. The system may further include a conduit able to pass water from the concentration tank to the heated reactor and at least one heat exchanger able to exchange process heat.

Additional advantages of some embodiments of the invention include:

Mixtures of labile and recalcitrant proteins may be processed simultaneously.

Presently existing plug flow reactors may be used.

Waste reduction is coupled with food or protein supplement production.

Protein digestibility increases significantly when it is solubilized.

The process is simple and allows recovery of some components and heat.

Food safety is improved if prions are destroyed.

Grinding increases the reaction rate of protein digestion, allowing for increased product concentration and decreased product degradation.

Nonreactive components may be purged.

The protein product may be concentrated and dried.

Microorganisms may be destroyed.

The invention also includes reactor systems suitable to house processes of the present invention.

For a better understanding of the invention and its advantages, reference may be made to the following description of exemplary embodiments and accompanying drawings.

BRIEF DESCRIPTION OF THE DRAWINGS

The following figures relate to selected embodiments of the present invention.

DETAILED DESCRIPTION

The present invention relates to a process for solubilizing protein from a biological source through hydrolysis. It also relates to devices for use in such solubilization and to a solubilization system.

Specific embodiments described hereafter relate to solubilization of protein from three different groups of biological sources. The first group includes recalcitrant or keratinous protein sources such as chicken feathers and animal hair. The second group includes labile or animal tissue protein sources such as chicken offal and shrimp heads. The third group includes plant protein sources such as soybean hay and alfalfa. Additional groups of protein sources and examples within the three groups above will be apparent to one skilled in the art.

The process generally involves application of an alkali such as lime ($Ca(OH)_2$ or calcium hydroxide) to the protein source at a particular temperature. A liquid product is obtained with some solid residue. In specific embodiments described below in Table 1, process conditions suitable for each of the three source groups are provided.

TABLE 1

Suitable treatment conditions for solubilizing protein

| | Protein Source | | |
|---|---|---|---|
| | Recalcitrant | Labile | Plant |
| Temperature (° C.) | 100 | 75 | 100 |
| Time (h) | 4-8 (feathers) 16 (hair) | 0.25 | 2.5 |
| Lime Loading (g $Ca(OH)_2$/g material) | 0.1 (feathers) 0.25 (hair) | 0.075 | 0.05-0.075 |
| Concentration (g material/L slurry) | 100 | 60-80 | 60 |

In certain embodiments of the invention, a well-insulated, stirred reactor is used to perform protein hydrolysis (solubilization) for different time periods, to obtain a liquid product rich in amino acids.

Although lime is used in some embodiments of the present invention, alternative alkalis such as magnesium oxide, magnesium hydroxide, sodium hydroxide, sodium carbonate, potassium hydroxide and ammonia may also be used in the present invention. However, most such alkalis may not be recovered by carbonation.

Lime also provides benefits over some other alkalis because it is poorly soluble in water. Due to its low solubility, lime maintains a relatively constant pH (~12) for an aqueous solution, provided enough lime is in suspension in the solution. This ensures a constant pH during the thermo-chemical treatment and relatively weaker hydrolysis conditions (compared to sodium hydroxide and other strong bases), which may reduce the degradation of susceptible amino acids.

The thermo-chemical treatment of high-protein materials generates a mixture of small peptides and free amino acids. During the treatment, newly generated carboxylic acid ends of peptides or amino acids react in an alkaline medium to generate carboxylate ions, consuming lime or other alkali in the process.

Figure 1:
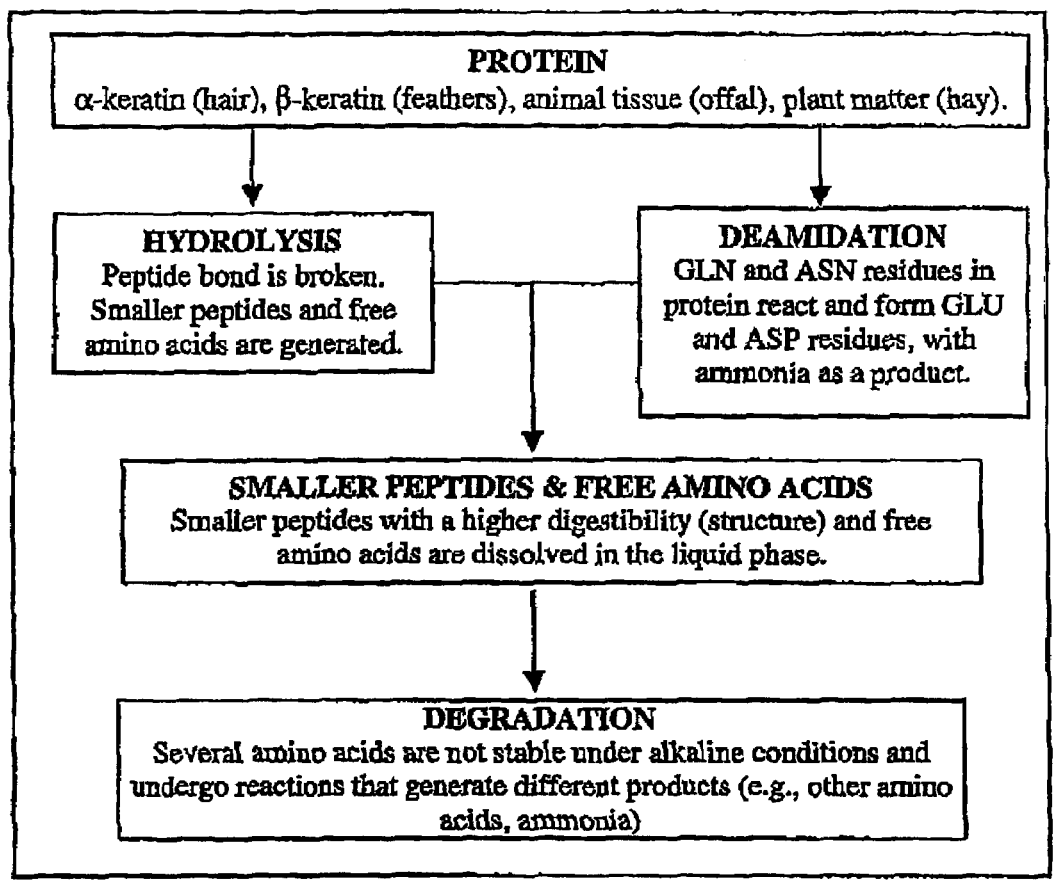
FIG. 1 shows a step-wise diagram for the hydrolysis of protein-rich material under alkaline conditions.

During the protein hydrolysis, several side reactions occur. FIG. 1 shows a step-wise diagram for the hydrolysis of protein-rich material under alkaline conditions. Ammonia is generated as a by-product during amino acid degradation (e.g., deamidation of asparagine and glutamine, generating aspartate and glutamate as products). In some embodiments, this ammonia may be captured and neutralized with an acid, such as sulfuric acid, to produce ammonium salts. These salts may then be used as fertilizer or for other purposes.

Arginine, threonine and serine are also susceptible to degradation under alkaline conditions. The susceptibility of arginine and threonine to degradation of nutritional importance because both are essential amino acids. Reducing the contact time between the soluble peptides and amino acids with the alkaline medium decreases degradation and increases the nutritional quality of the final product. The use of low temperatures (~100° C.) may also reduce and degradation.

A step-wise treatment of protein-rich materials may be used when long-term treatment times are required for high solubilization efficiencies (animal hair and chicken feathers). An initial product of better quality is obtained during the early treatment, whereas a lower quality product is generated thereafter. For example, a series of lime treatments may be used to obtain products with different characteristics when the initial waste is a mixture. For example, in an offal+feathers mixture, an initial treatment may target the hydrolysis of chicken offal, using low temperatures and short times, while a second lime treatment (longer time and higher temperature) may digest the feathers.

Table 2 summarizes the suitable conditions and effects of the different treatment variables (temperature, concentration, lime loading and time) on protein hydrolysis for different materials.

TABLE 2

Suitable conditions for thereto-chemical treatment of materials studied

| Material | Notes | Recommended conditions |
|---|---|---|
| Alfalfa hay (15.8% protein) | Hydrolysis increases with temperature, and alfalfa hay concentration (up to 60 g/L). Lime loading has the least significant effect but is required to convert protein into small peptides and free amino acids. Suitable for ruminants. | 0.075 g $Ca(OH)_2$/g alfalfa, 100° C., 60 min, 60 g/L. |
| Soybean hay (19% protein) | Hydrolysis increases with lime loading and temperature (up to 100° C.), 100° C. recommended because of lower energy | 0.05 g $Ca(OH)_2$/g soybean, 100° C., 150 min. |

TABLE 2-continued

Suitable conditions for thereto-chemical treatment of materials studied

| Material | Notes | Recommended conditions |
|---|---|---|
|  | requirements. Soybean hay concentration has no significant effect. The no-lime experiment gives significantly lower hydrolysis conversions. Suitable for ruminants. |  |
| Shrimp head waste | Reaction is complete after 30 min. Temperature has no significant effect. Hydrolysis increases with lime loading (up to 0.05 g $Ca(OH)_2$/g dry shrimp). Suitable for monogastrics. | 0.05 $Ca(OH)_2$/g dry shrimp, at least 75° C., at least 15 min. |
| Offal (15% protein) | No significant change in conversion occurs after 30 min. Offal concentration has no significant effect. Hydrolysis increases with lime loading (up to 0.1 g $Ca(OH)_2$/g dry offal). Suitable for monogastrics. | 0.075 g $Ca(OH)_2$/g dry offal, 75° C., at least 15 min. |
| Offal + feathers | A two-step process was studied: Step 1 targets the hydrolysis of offal and generates a high-quality amino acid mixture. Step 2 targets the hydrolysis of feathers and generates a ruminant feed. | Step 1: 0.075 g $Ca(OH)_2$/g dry offal, 50-100° C., 30 min. Step 2: ~0.05 g $Ca(OH)_2$/g feathers, 100° C., 2-4 h. |
| Feathers (96% protein) | Hydrolysis occurs faster than with hair, 70% conversion obtained after 6 h. Suitable for ruminants. | 0.1 g $Ca(OH)_2$/g feathers, 100° C., 4-8 h. |
| Hair (92% protein) | Long-term treatment required for high protein hydrolysis. Two-step process recommended for reducing amino acid degradation. Suitable for ruminants. | Step 1: 0.25 g $Ca(OH)_2$/g hair, 100° C., 8 h. Step 2: ~0.25 g $Ca(OH)_2$/g hair, 100° C., 8 h. |

The use of calcium hydroxide as the alkaline material in a process of the present invention produces a relatively high calcium concentration in the liquid product obtained from the reaction (also referred to as the "centrifuged solution" in some embodiments). Because some calcium salts have low solubility, calcium can be recovered by precipitating it as $CaCO_3$, $Ca(HCO_3)_2$, or $CaSO_4$. Calcium carbonate may be preferred because of its low solubility (0.0093 g/L, solubility product for $CaCO_3$ is $8.7 \times 10^{-9}$). In contrast, the solubility of $CaSO_4$ is 1.06 g/L, with a solubility product of $6.1 \times 10^{-5}$, and the solubility of $Ca(HCO_3)_2$ is 166 g/L, with a solubility product of 1.08. Also, it is easier to regenerate $Ca(OH)_2$ from $CaCO_3$ than from $CaSO_4$.

Precipitation of calcium carbonate by bubbling $CO_2$ into the reaction liquid product results in a calcium recovery between of 50 and 70%. A high pH in the reaction liquid product before calcium recovery may be recommended (>10) so that calcium carbonate and not calcium bicarbonate is formed during the process. A pH of 9 may also be sufficient in some embodiments. A final pH after recovery may be between ~8.8 and 9.0.

Proteins resulting from process of the present invention may have many uses, including use as animal feed. As a general rule, the soluble protein from recalcitrant and plant protein sources does not have a well-balanced amino acid profile. These proteins are accordingly best used as ruminant feed. In labile proteins, the amino acid profiles are well balanced, so the solubilized protein may also be used as feed for monogastric animals. Thus the end uses of the proteins solubilized by the present process may be indicated by the original source of such proteins. An additional benefit in animal feed uses may be the lack of prions in protein produced by some processes of the present invention. Lime treatment conditions are severe enough in many processes to substantially destroy prions, thereby improving the safety of any food produced using the solubilized proteins.

Additionally, in some embodiments the invention may include a holding step in which reaction liquid is heated to an elevated temperature for a certain time period to destroy all or a significant amount of prions that may be present in the liquid. For example, the liquid may be heated to a temperature of between 125-250° C. for between 1 second and 5 hours.

Protein-rich materials often found in waste may be subdivided into three categories: keratinous, animal tissue, and plant materials, each with different characteristics.

Animal hair and chicken feathers have high protein content (~92% and ~96%, respectively), with some contaminants such as minerals, blood, and lipids from the slaughter process. The main component in animal hair and chicken feathers is keratin. Keratin is a mechanically durable and chemically unreactive protein, consistent with the physiological role it plays: providing a tough, fibrous matrix for the tissues in which it is found. In mammal hair, hoofs, horns and wool, keratin is present as α-keratin; and in bird feathers it is present as β-keratin. Keratin has a very low nutritional value; it contains large quantities of cysteine and has a very stable structure that render it difficult to digest by most proteolytic enzymes.

Figure 2:
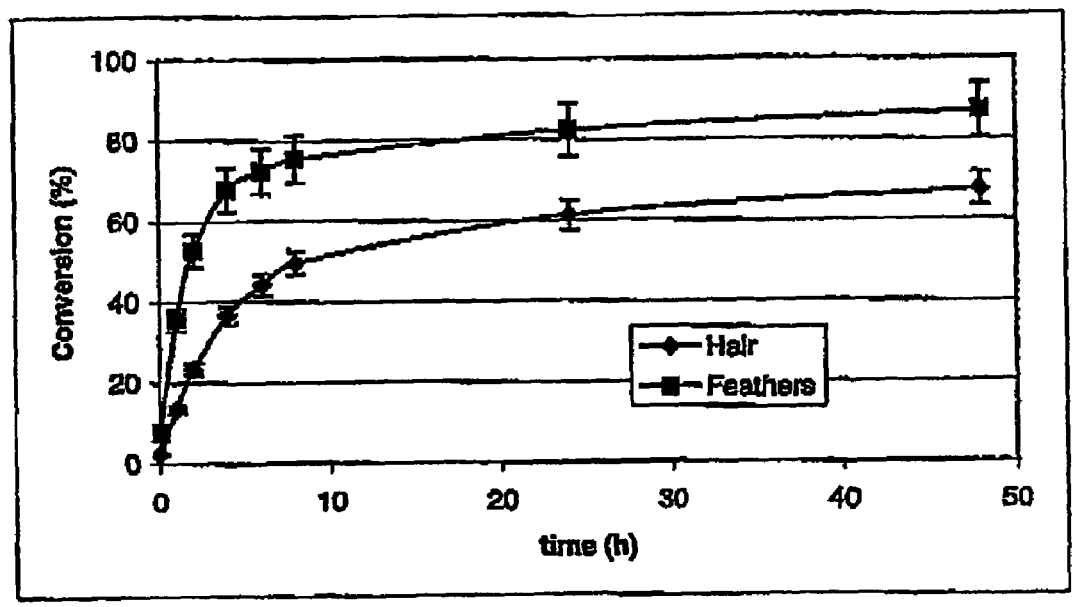
FIG. 2 is a graph showing the hydrolysis of chicken feathers and animal hair. Each point represents the average of three values +/−2 standard deviations.
Figure 3:
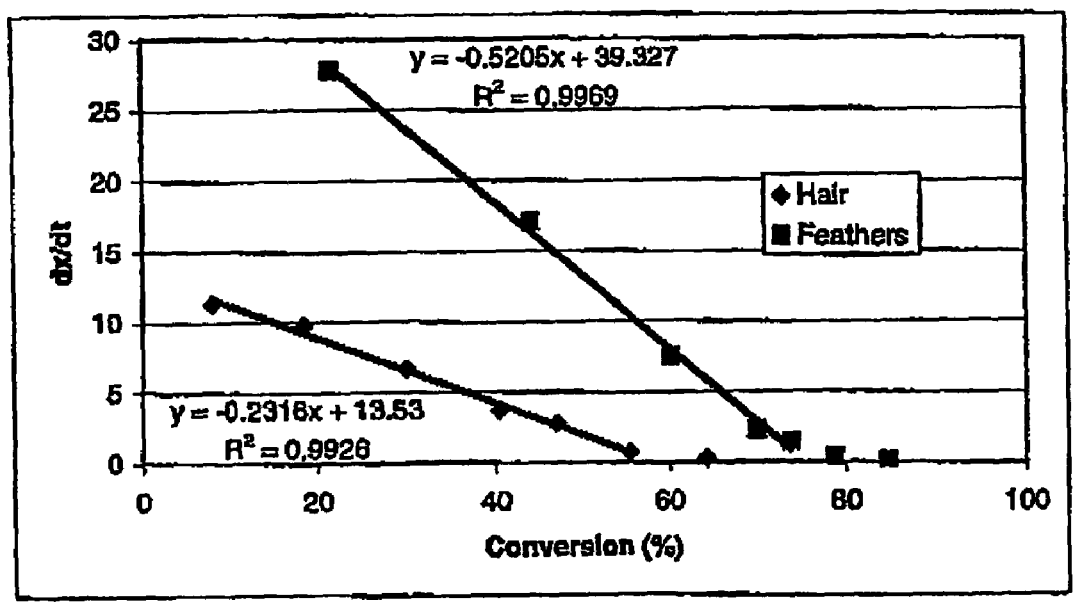
FIG. 3 is a graph showing the reaction rate vs. conversion for animal hair and chicken feathers.
Figure 22:
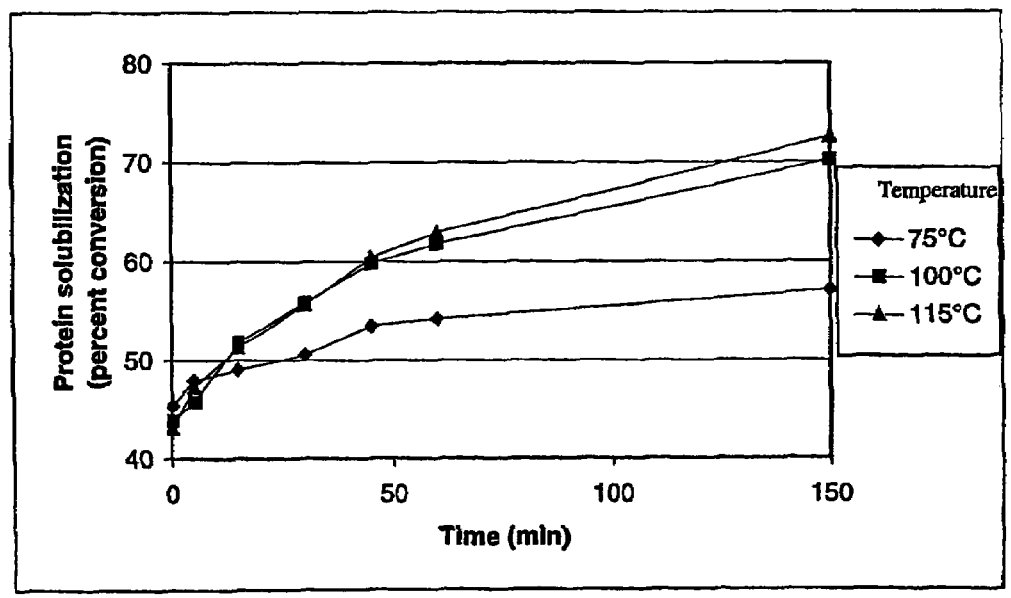
FIG. 22 is a graph illustrating temperature effect on protein solubilization of soybean hay.

The behavior of chicken feathers and animal hair during some the thermo-chemical treatment processed of the present invention is presented in FIGS. 2 and 3. FIG. 22 shows a higher hydrolysis rate for chicken feathers than for animal hair, and a higher final conversion to digestible protein. This difference may be explained by the easier lime accessibility to a more extended conformation in β-keratin, or by the different macro structure present in animal hair when compared to chicken feathers (fibril structure, porosity, etc.). At least 8 hours is recommended for a high hair conversion at 100° C. with 0.1 g $Ca(OH)_2$/g dry matter lime loading, but in the case of feathers, 70% conversion can be achieved in ~4 hours.

A linear relation between the reaction rate and conversion is found for both materials (FIG. 3), indicating a first order reaction rate for the alkaline hydrolysis of protein. A pseudo-equilibrium of hydrolysis vs. degradation is found at high conversions.

Animal tissue offers fewer digestive challenges than keratinous materials. Cells in animal tissues contain nuclei and other organelles in a fluid matrix (cytoplasm) bound by a simple plasma membrane. The plasma membrane breaks easily, liberating glycogen, protein, and other constituents for digestion by enzymes or chemicals.

Figure 4:
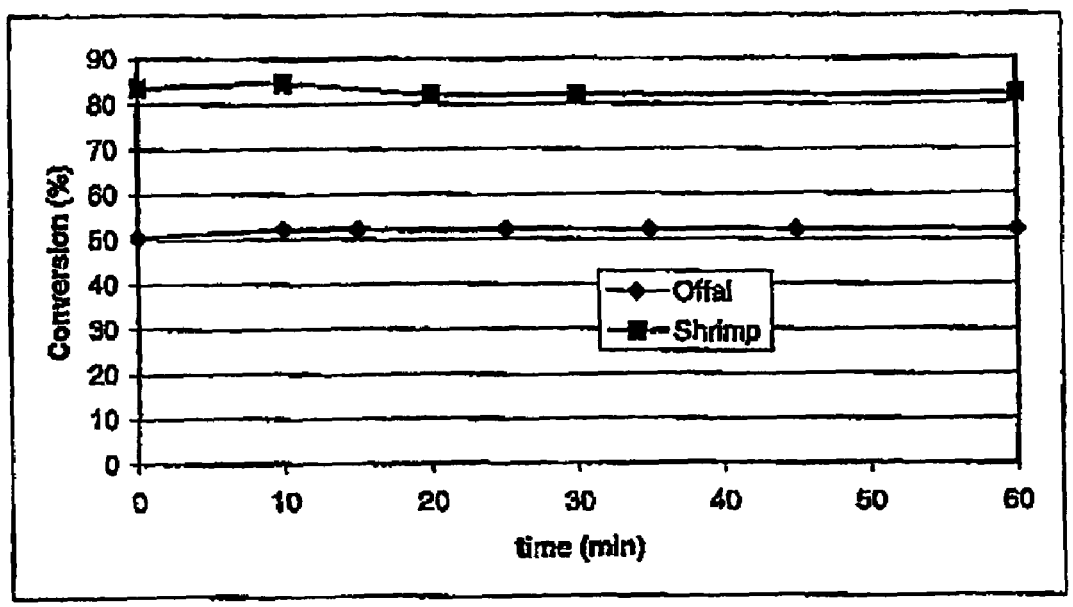
FIG. 4 is a graph showing conversion vs. time for protein hydrolysis of shrimp heads and chicken offal.

Animal tissues (offal and shrimp heads) hydrolyze well in less than 15 minutes (FIG. 4) and do not require strong treatment conditions; low temperature, low lime loading, and short times are suitable. Lipids and other materials present in animal tissue consume lime more rapidly through side reactions such as lipid saponification, resulting in lower pH of the liquid product at the end of the process and making the liquid product susceptible to fermentation.

Shrimp heads and chicken offal are both animal protein by-products from the food industry. Because these are animal tissues, the amino acid distribution of the liquid product is expected to be similar to animal requirements, although quality may vary because the materials vary from batch to batch. Histidine may be the limiting amino acid in the liquid product.

Another specific use for the present process involves the disposal of dead birds in the poultry industry. For example, approximately 5% of chickens die before reaching the slaughterhouse. A typical chicken coop does not, however, have enough dead birds to process on site, so a method is needed to store the dead birds while the await pick up for processing. Using a process of the present invention, the dead birds can be pulverized with suitable equipment such as a hammer mill and lime may be added to raise the pH of the birds and prevent spoilage. The lime concentration may be approximately 0.1 g $Ca(OH)_2$/dry g dead bird. When the lime-treated birds are collected and brought to a central processing plant, they may be heated to complete the protein solubilization process.

Figure 5:
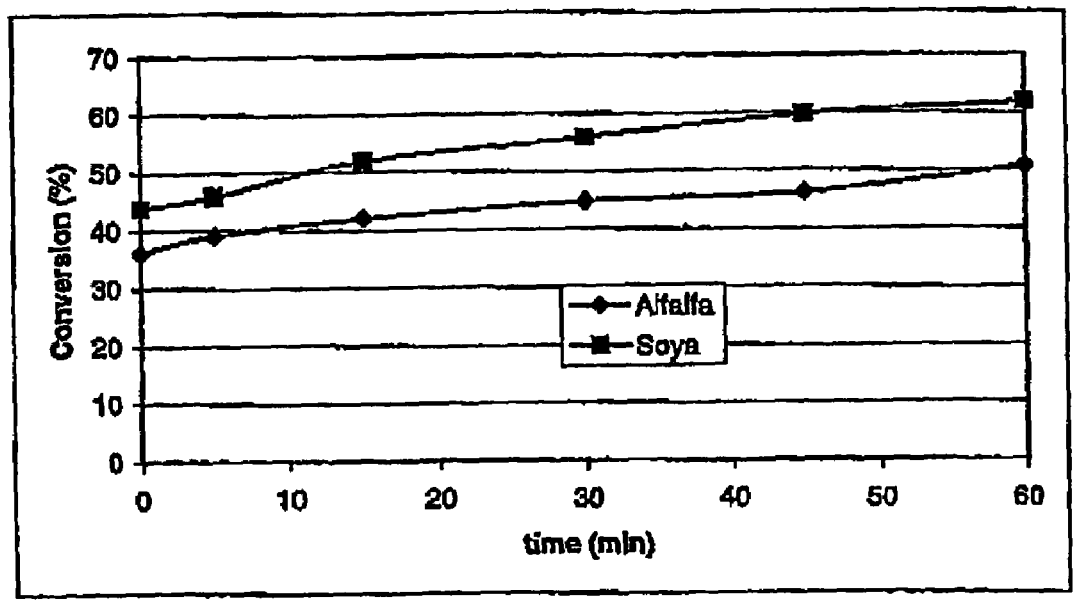
FIG. 5 is a graph showing conversion vs. time for protein hydrolysis of soybean hay and alfalfa hay.

Finally, plants contain a difficult-to-digest lignocellulosic matrix in their the complex cell walls, rendering them more difficult to digest than animal tissue. However, the presence of highly water-soluble components results in a high initial conversion of protein into a liquid during some processes of the present invention. FIG. 5 compares the protein hydrolysis rates for soy bean and alfalfa hay. It shows a higher soluble fraction for soybean hay than alfalfa hay and a similar hydrolysis rate for both materials.

Lime treatment of these plant materials generates a product poor in lysine and threonine, which will decrease the nutritional value of the liquid product for mono-gastric animals.

In some embodiments of the invention in which the process is used to solubilize protein from plants, the resulting fiber in the solid residue is also more digestible because lignin and acetyl groups are removed. Lime treatment of plant materials may generate two products, a liquid product which is rich in protein (small peptides and amino acids from alkaline hydrolysis), and a solid residue rich in holocellulose that can be treated to reduce its crystallinity and increase its degradability. Thus there is an unexpected synergistic effect when some processes of the present invention are combined with plant digestion processes.

Figure 6:
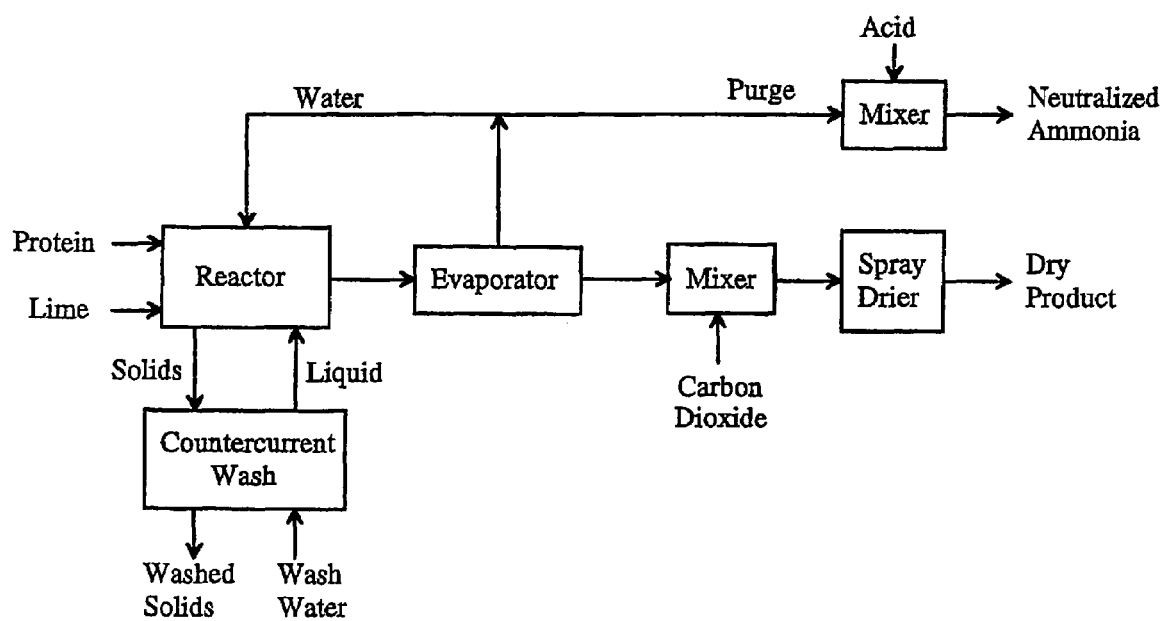
FIG. 6 illustrates a single-stage solubilization process with no calcium recovery according to an embodiment of the present invention.

FIG. 6 shows a process for solubilization of protein in protein-containing materials. The process does not include lime recovery. In the process, the protein-containing material and lime are added to a reactor. In a specific embodiment, quick lime (CaO) is added so that the heat of its reaction creates the hydrated form, slake lime ($Ca(OH)_2$) reduces further heat requirements of the reaction. The unreacted solids may be countercurrently washed to recover the solubilized protein trapped within the unreacted solids. The liquid product exiting the reactor contains the solubilized protein. An evaporator concentrates the solubilized protein by removing nearly all of the water. Preferably enough water may remain so that the concentrated protein is still pumpable.

Suitable evaporators include multi-effect evaporators or vapor-compression evaporators. Vapor compression may be accomplished using either mechanical compressors or jet ejectors. Because the pH is alkaline, any ammonia resulting from protein degradation will volatilize and enter the water returned to the reactor. Eventually the ammonia levels may build up to unacceptable levels. At that time a purge steam may be used to remove excess ammonia. The purged ammonia may be neutralized using an acid. If a carboxylic acid is used, (e.g. acetic, propionic or butyric acid), then the neutralized ammonia can be fed to ruminants as a nonprotein nitrogen source. If a mineral acid is added, the neutralized ammonia may be used as a fertilizer.

The concentrated protein slurry exiting the evaporator may be carbonated to react excess lime. In some applications, this concentrated slurry may be directly added to feeds provided that shipping distances are short. However, if shipping distances are long and a shelf-stable product is needed, the neutralized concentrated slurry may be spray dried to form a dry product. This dry product contains a high calcium concentration. Because many animals need calcium in their diet, the calcium in the solubilized protein may be a convenient method of providing their calcium requirement.

Figure 7:
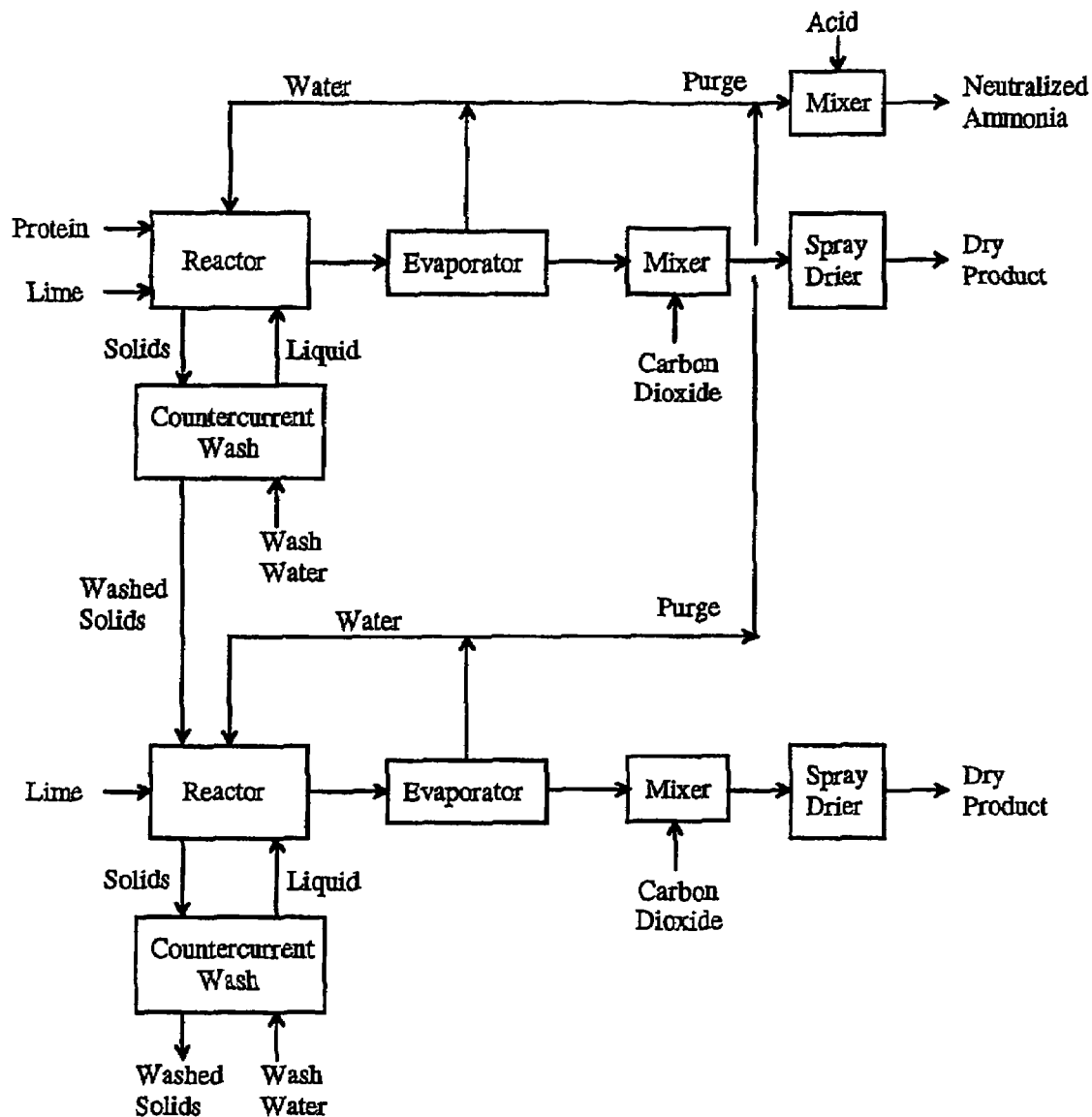
FIG. 7 illustrates a two-stage solubilization process with no calcium recovery according to an embodiment of the present invention.

Referring now to FIG. 7, a similar process divided into two stages is illustrated. This process is suitable for protein-containing materials that have a mixture of proteins suitable for ruminant and monogastric feeds. For example, dead birds contain feathers (suitable for ruminants) and offal (suitable for monogastrics). The first stage of the process employs mild conditions that solubilize labile proteins, which may then be concentrated, neutralized and dried. These proteins may be fed to monogastrics. The second stage employs harsher conditions that solubilize the recalcitrant proteins, which may be concentrated, neutralized and dried. These proteins may be fed to ruminants.

Figure 8:
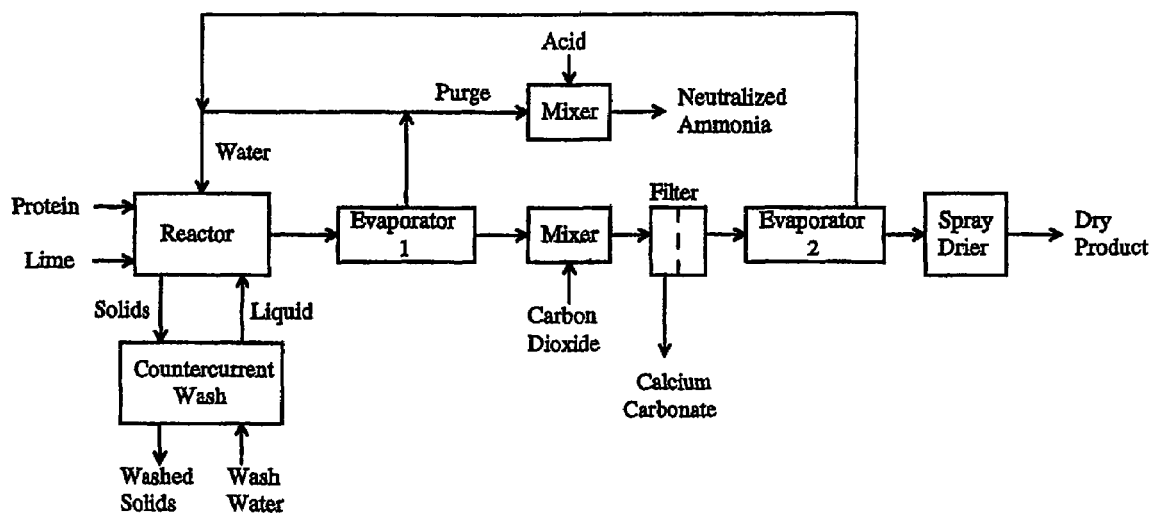
FIG. 8 illustrates a one-stage solubilization process with calcium recovery according to an embodiment of the present invention.

FIG. 8 illustrates a process similar to that of FIG. 6, with an additional calcium recovery step to yield a low-calcium product. To recover calcium, the evaporation stage occurs in two steps. In the first evaporator, the proteins in the existing stream remain in solution. Carbon dioxide is added to precipitate the calcium carbonate. During this step the pH is preferably approximately 9. Addition of too much carbon dioxide results in a drop in pH favoring calcium bicarbonate formation. Because calcium bicarbonate is much more soluble than calcium carbonate, calcium recovery is reduced if this occurs. The calcium carbonate is recovered using a filter. The calcium carbonate may be countercurrently washed to recover soluble protein. The second evaporator then removes most of the remaining water. Enough water may be left so that the exiting slurry is pumpable. Finally, the slurry may be spray dried to form a shelf-stable product.

Figure 9:
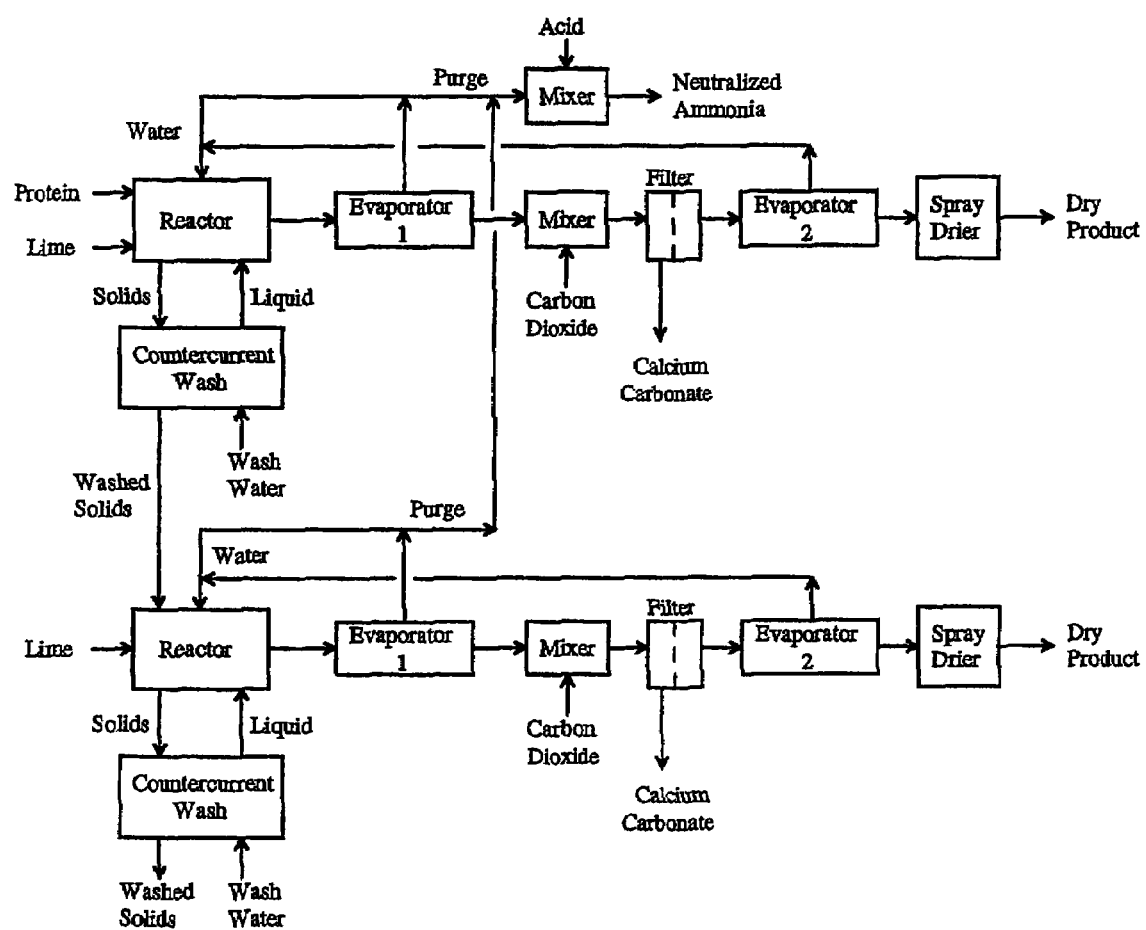
FIG. 9 illustrates a two-stage solubilization process with calcium recovery according to an embodiment of the present invention.

FIG. 9 shows the two-stage version of FIG. 8 which may be used to process protein sources that have a mixture of labile and recalcitrant proteins. The first stage solubilizes labile proteins that are suitable for monogastrics and the second stage solubilizes proteins that are suitable for ruminants.

Figure 10:
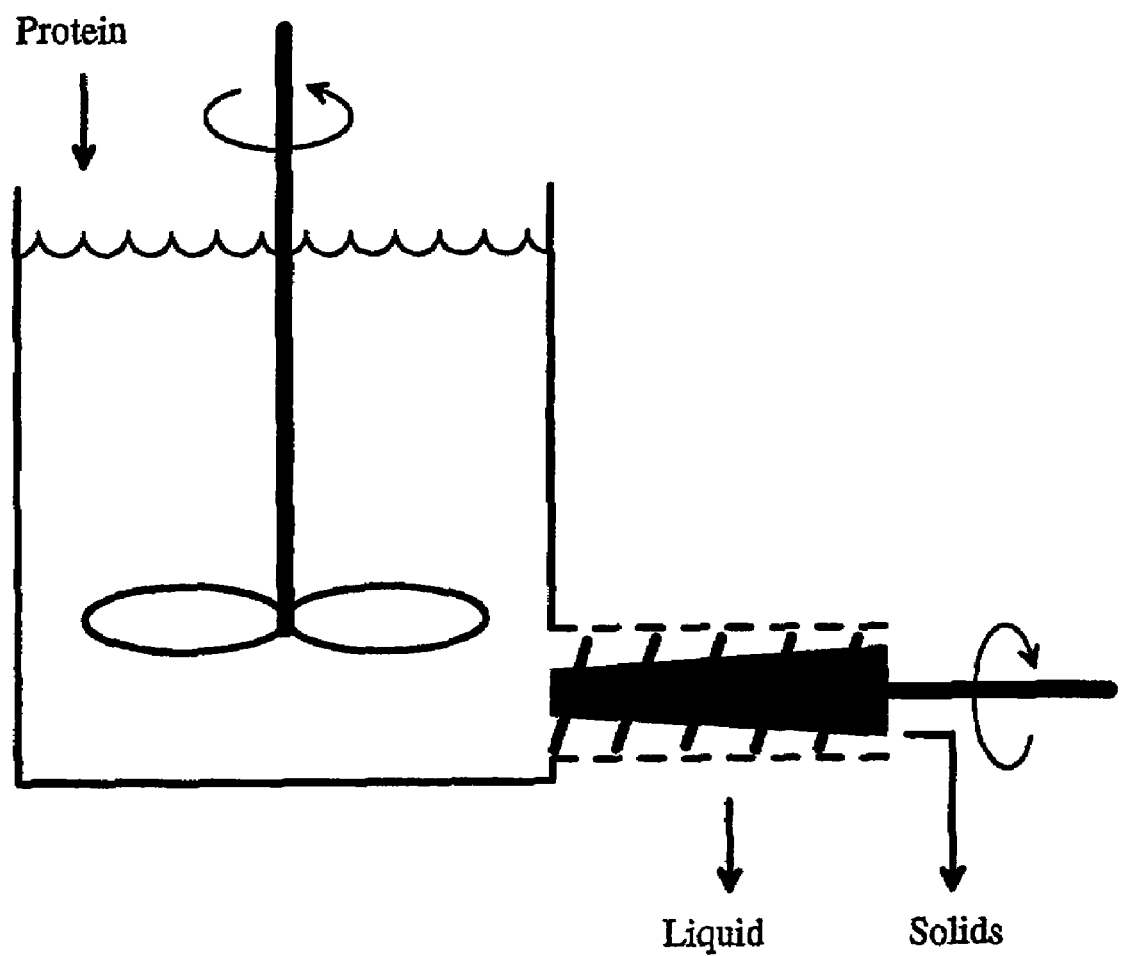
FIG. 10 illustrates a one-stage reactor according to an embodiment of the present invention.

FIG. 10 shows a single-stage continuous stirred tank reactor (CSTR) which is suitable for processing labile proteins. The solids exit the reactor using a screw conveyor that squeezes out liquid from solids.

Figure 11:
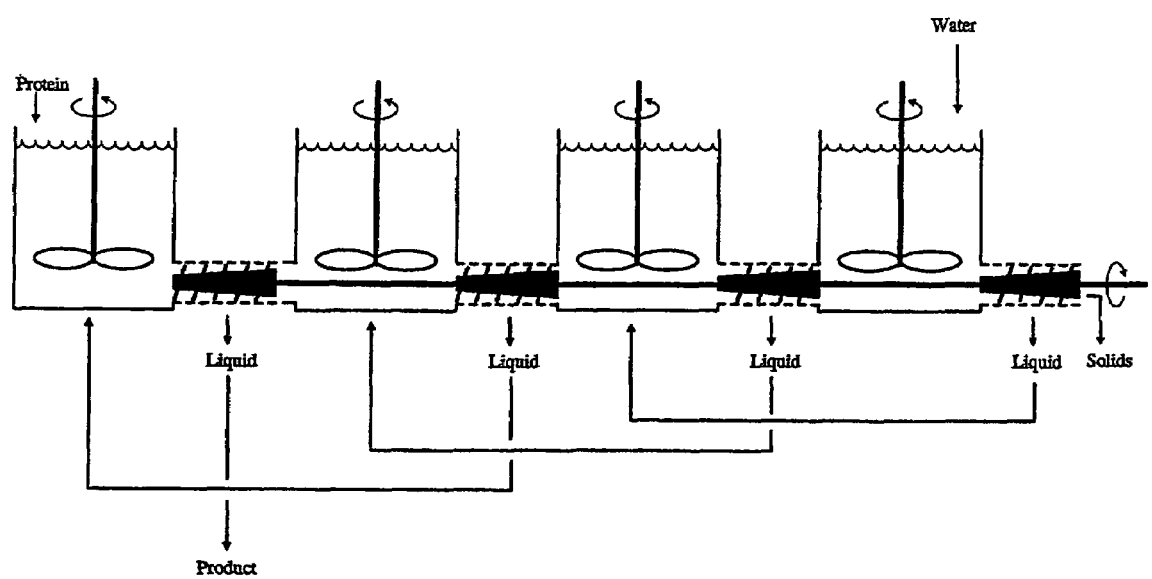
FIG. 11 illustrates a multi-stage reactor with countercurrent flow according to an embodiment of the present invention.

FIG. 11 shows multi-stage CSTRs. Four stages are shown, which approximates a plug flow reactor. This reactor type is well suited for use with recalcitrant and plant protein sources. The plug flow behavior minimizes the amount of reacted feed that exits with spent solids. In this embodiment, the liquid flow is countercurrent to the solid flow.

Figure 12:
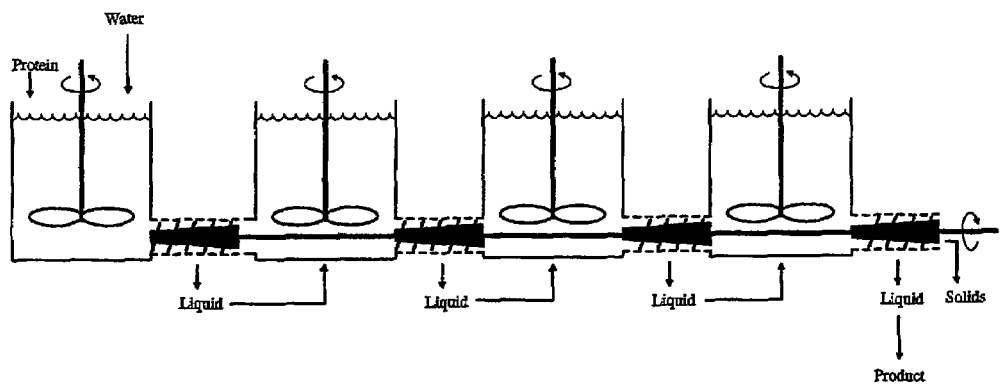
FIG. 12 illustrates a multi-stage reactor with cocurrent flow according to an embodiment of the present invention.

FIG. 12 shows multi-state CSTRs in which the liquid flow is cocurrent to the solids flow.

Figure 13:
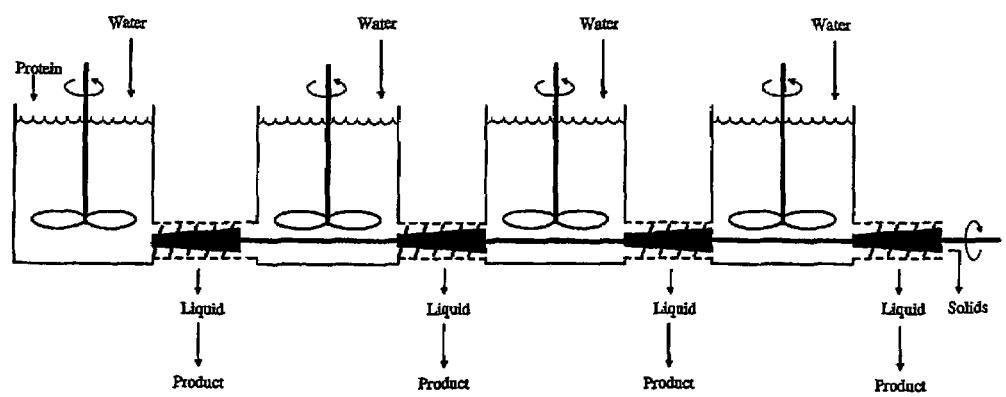
FIG. 13 illustrates a multi-stage reactor with crosscurrent flow according to an embodiment of the present invention.

FIG. 13 shows multi-stage CSTRs in which the liquid flow is crosscurrent to the solids flow.

Figure 14:
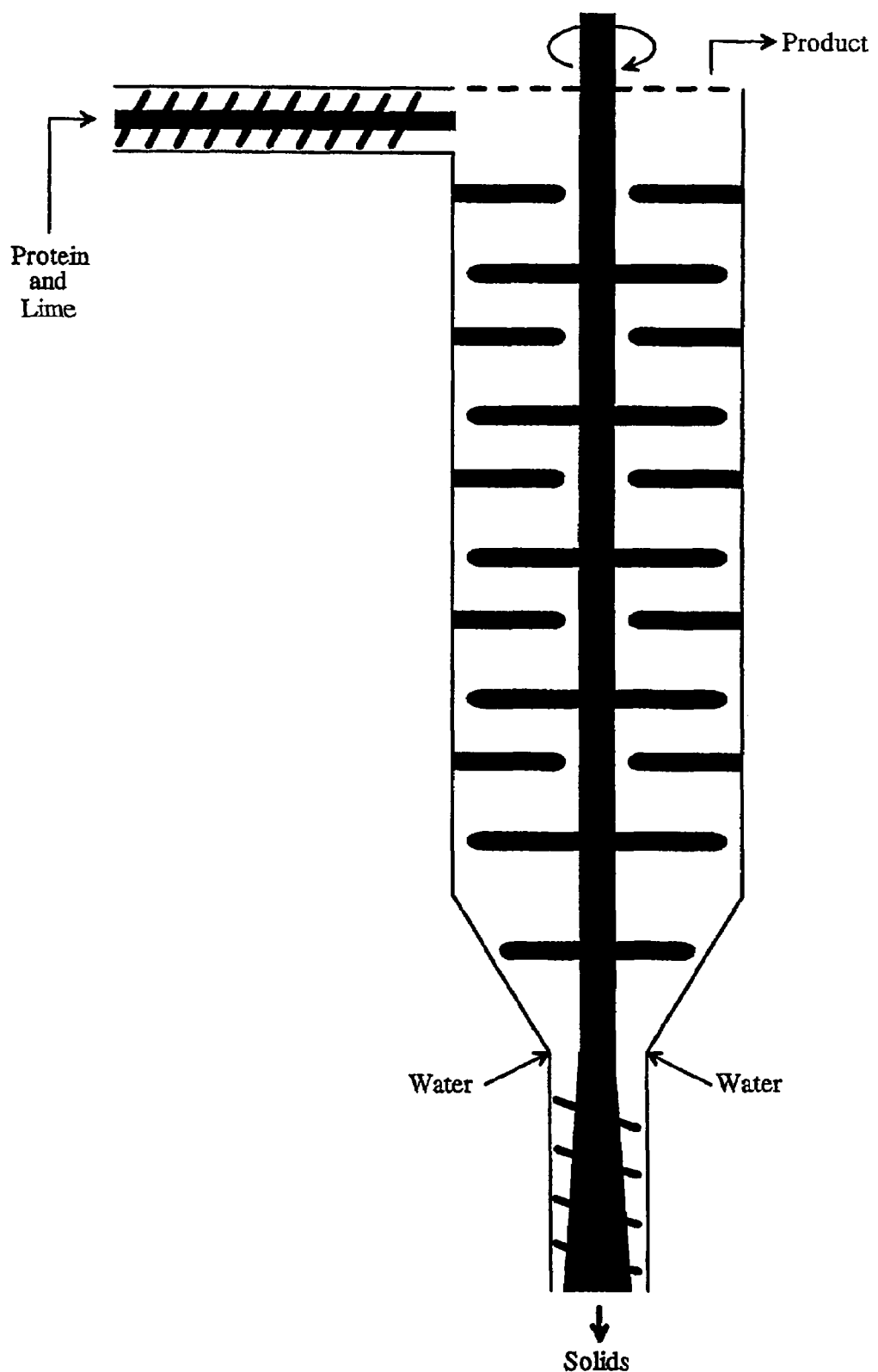
FIG. 14 illustrates a plug flow reactor with a unitized mixer and exit screw conveyor according to an embodiment of the present invention.

FIG. 14 shows a true plug flow reactor which is well suited for recalcitrant and plant protein sources. Protein is fed into the reactor using appropriate solids equipment, such as a screw conveyor as shown in FIG. 14 or a V-ram pump, not shown. The reactor contains a central shaft that rotates "fingers" that agitate the contents. Stationary "fingers" are attached to the reactor wall to prevent the reactor contents from spinning unproductively. Water is passed countercurrently to the flow of solids. The water exiting the top of the reactor contains solubilized protein product. It exits through a screen to block solids. The fibrous nature of some protein sources such as chicken feathers, hair, and plants make their filtration easy. The unreacted solids at the bottom of the reactor are removed using a screw conveyor that squeezes liquids from the solids. In this embodiment, the squeezed liquid flows back into the reactor rather than through screen on the side of the screw conveyor. The object of such an arrangement is to have the solids exit as a tight plug so that the water added to the bottom of the reactor preferentially flow upward, rather than downward. Because the exiting solids were contacted just prior to exit with water entering the reactor, there is no need to countercurrently wash these solids.

Figure 15:
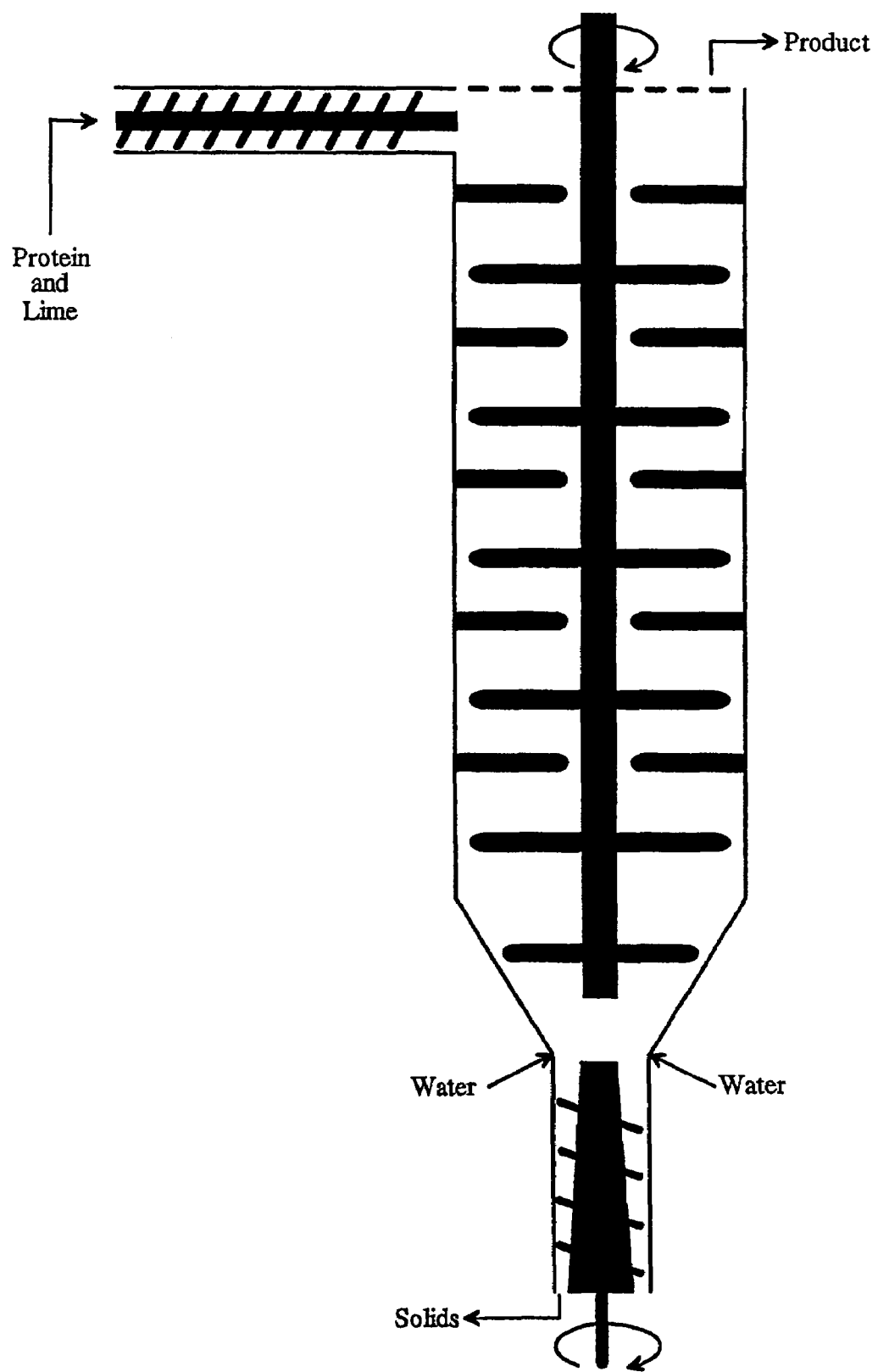
FIG. 15 illustrates a plug flow reactor with a separated mixer and exit screw conveyor according to an embodiment of the present invention.

FIG. 15 shows a plug flow reactor similar to the one shown in FIG. 14, except the exit screw conveyor is not connected to the center shaft of the reactor. This allows for mixing speed and conveyor speed to be independently controlled.

Figure 16:
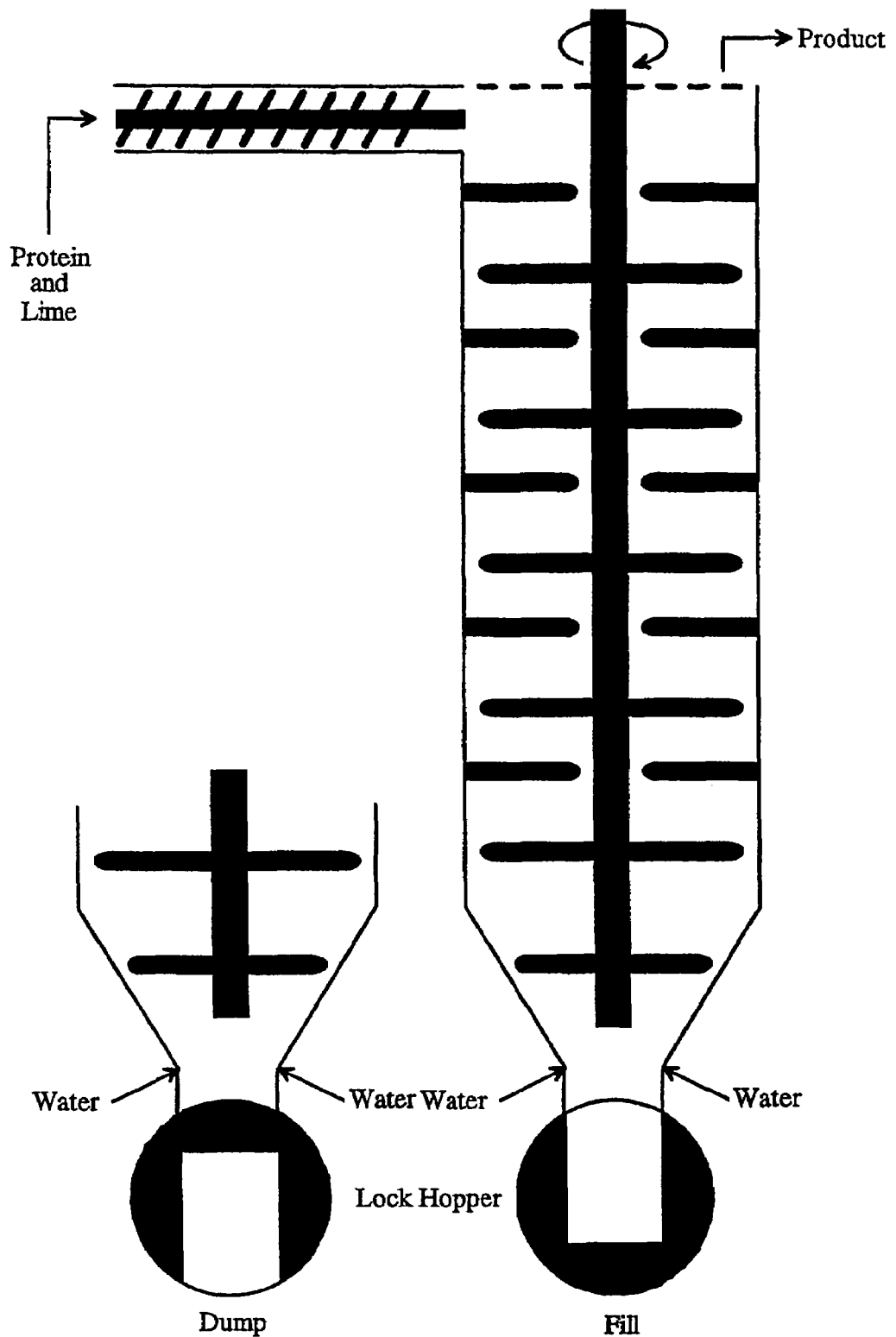
FIG. 16 illustrates a plug flow reactor with a lock hopper according to an embodiment of the present invention.

FIG. 16 shows a plug flow reactor similar to the one shown in FIG. 14, with the exception that solids exit through a lock hopper rather than a screw conveyor. To prevent air from entering the reactor, the lock hopper may be evacuated between cycles.

Figure 53:
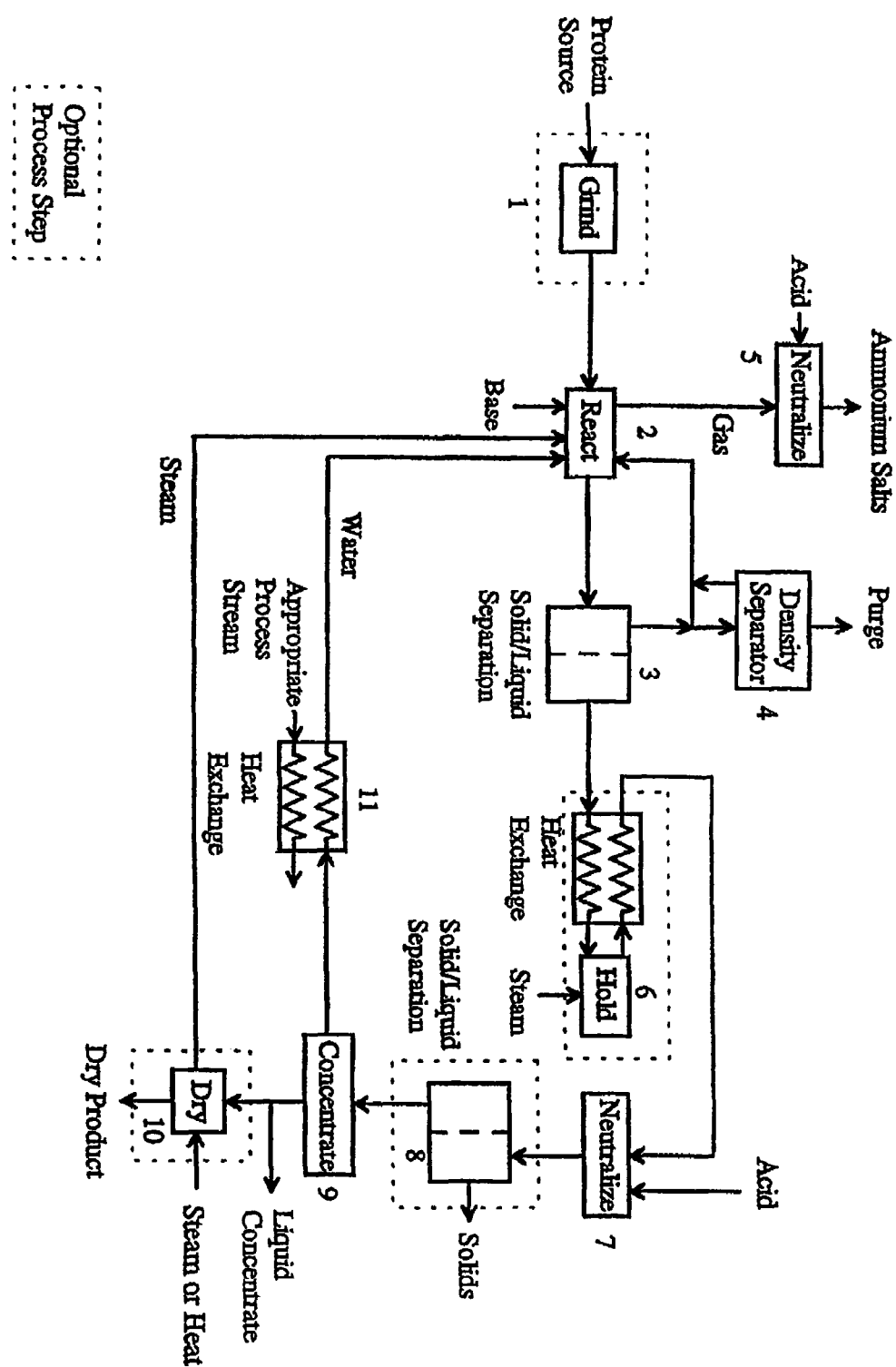
FIG. 53 illustrates a single-stage solubilization process according to an embodiment of the present invention.

FIG. 53 shows a process for solubilization of protein in protein-containing materials. First, in an optional grinding step, the protein source is ground to increase its surface area. This increases the reaction rate in the reacting step. Once the protein is solubilized in a reactor, it begins to degrade, thus a faster reacting step may reduce the amount of degradation. A faster reaction rate may also increase the reaction product concentration, making it cheaper to recover. If a grinding step is used, it may be achieved using hammer mills, in-line homogenizers, or other suitable equipment.

Next the protein is reacted with an alkali at an elevated temperature and pH. The pH may fall between around 10 and 13, for example, it may be approximately 12. Any base may be used in this reaction step, but in selected embodiments the base is calcium oxide, calcium hydroxide, magnesium oxide, magnesium hydroxide, sodium hydroxide, sodium carbonate, potassium hydroxide, or ammonia. Calcium oxide and calcium hydroxide are poorly soluble in water and thus may be recovered more easily. They also buffer pH to approximately 12. Further, calcium is a dietary nutrient and need to be removed from the final protein product. Other nutrient alkalis may also be left in the final protein product. General reaction conditions may be as described herein, for example, for different protein sources.

The reactor may be a stirred tank. It may be operated at 1 atm, although increased pressure may also be used, particularly with higher temperatures, to achieve faster reaction rates. Steam from other parts of the process may be used to maintain reactor temperature, for example by purging it directly into the reactor.

During the reaction, some amino acids decompose to ammonia. This ammonia will usually enter the gas phase. It may be neutralized with an appropriate acid, such as sulfuric acid, to form ammonia salts. These ammonia salts may then be used for fertilizer or other applications.

Next solids and liquids are separated in a stream exiting the reaction. This may be accomplished using a solid/liquid separator. The solids recovered may contain both reactive solids, such as unsolubilized protein, and inert solids, such as bones and rocks. Most inert solids have a higher density than reactive solids and that property may be exploited to aid separation. This step allows repetitive recycling of reactive solids, improving overall yield for the process. It also allows removal of inert solids whose presence can decrease the efficiency of the reaction step and the process overall.

Density separators that may be used to separate reactive and inert solids include settlers and hydroclones.

Next an optional hold step may occur. In this step, the liquid from the reaction step containing solubilized protein may be heated to an elevated temperature for a certain time period, then cooled. It is possible that the liquid may contain intact prions after the reaction step. These prions can present a health hazard to any animals that later consume the solubilized proteins and also to humans. However, the heating during the hold stem may be sufficient to destroy all or a significant portion of any prions present in liquid. This hold step may be similar to pasteurization. For different types of prions, appropriate temperatures and holding times may vary. In most cases there will be a variety of temperature and holding time combinations sufficient to achieve prion destruction. In specific embodiments, the holding step conditions may be selected so as to achieved a desired level of prion destruction, but also to simultaneously limit amino acid degradation. For example, the hold step temperature may be between 125-250° C. The holding time may be between 1 second and 5 hours. In order to select the most appropriate holding step conditions, prions likely to occur in the protein source may be previously identified.

The holding step may be heated by steam. The system may include a heat exchange element to allow heat from liquid leaving the holding step to be used to help warm liquid entering it.

The liquid may then be neutralized with an acid to reduce the pH to between 2 and 9. The acid used for this step may be nearly any acid or acid source. In specific embodiments, it may be carbon dioxide, phosphoric acid, carboxylic acids, such as acetic acid, propionic acid, and butyric acid, lactic acid, sulfuric acid, nitric acid, and hydrochloric acid.

Carbon dioxide may be used as an acid source particularly when the alkali contained calcium. Carbon dioxide is inexpensive and creates calcium carbonate or bicarbonate, depending on the pH, during neutralization of the calcium-containing reaction liquid. Both calcium carbonate and bicarbonate may be converted back to lime using a lime kiln. This lime may be reused in the reaction step.

Because carbon dioxide is a gas, it can cause the liquid to foam during neutralization. To avoid this problem, the carbon dioxide may be transferred into the liquid phase using a microporous, hydrophobic membrane, such as a membrane made by Celgard LLC (North Carolina).

Phosphoric acid is used in another particular embodiment when the reaction liquid contains calcium because the calcium phosphate formed is an important mineral in bone formation. Thus, it is a useful addition to the ultimate protein product.

In another embodiment, organic acids such as carboxylic acids and lactic acid may be used to neutralize liquid containing any alkali. Organic acids are a useful addition to the final protein product because they are an energy source for animals.

After neutralization, an optional solid/liquid separation may occur. This step may be most useful when the acid neutralization produces an insoluble salt, such as calcium carbonate, calcium bicarbonate, calcium sulfate or calcium phosphate. While some these materials may be desired in the final product, some may not, or it may be desirable to reduce their concentration in the final product. A solid/liquid separator may be used to remove all or part of the solids from the neutralized liquid. Suitable solid/liquid separators may include a filter press, a rotary drum filter and a hydroclone.

In one particular embodiment, neutralization of reaction liquid containing calcium via carbonation occurs at a pH of approximately 9. This allows substantial removal of calcium in the form of highly insoluble calcium carbonate via a solid/liquid separator. After a significant amount of calcium carbonate is removed, then carbonation or other neutralization may continue to reduce the pH further.

After neutralization and optional solid separation, the neutralized liquid may be concentrated. The reaction liquid typically has between 2-6% solubilized protein. This concentration is likely not significantly affected by the holding, neutralization and solid recovery steps. After concentration, the concentrated liquid may have between 35-65% solubilized protein.

Concentration may be achieved by evaporation. For example, multi-effect, mechanical vapor-compression, and jet ejector vapor compression evaporation may be used to removed water from the neutralized liquid. In general, dilute protein solutions tend to foam while concentrated ones do not. As a result, if the evaporators are operated using liquid containing at least 15% solubilized protein, foaming is reduced. Additionally, particularly for more dilute liquid, an antifoaming agent may be added to the liquid. Vegetable oils are effective antifoaming agents and add an energy component to the final protein product.

Filtration may also be used to concentrate the neutralized liquid. Specifically, a dilute solution may be concentrated by water permeation through an appropriate membrane, such as a reverse osmosis or tight nanofiltration membrane. To minimize concentration polarization, an oscillatory disk filter (e.g. VESP) may be used to achieve high permeation rates and high product concentrations.

The neutralized liquid may also be concentrated by freezing. As ice crystals form, protein is largely excluded, resulting in a separation of nearly pure frozen water and a concentration amino acid/polypeptide solution. The ice crystals may be washed, for example countercurrently, to remove concentrated product from their surface.

Water may also be extracted from the neutralized liquid using various immiscible amines, such as di-isopropyl amine, trimethyl amine, methyl diethyl amine, and other amines.

The water removed during the concentration step may be returned to the reaction step. It may be heated prior to its return via heat exchange with process steam or other warm fluid from other parts of the process. If the water from the concentration step is too hot for the reaction step, it may also be heat exchanged with a cooler fluid to bring it to an appropriate temperature before addition to the reaction.

The concentrated liquid may optionally be dried. Drying may be achieved using standard equipment such as spray driers or scraped drum driers. Scraped drum driers may produce a final solid with a high bulk density. Additionally, steam from these driers may be recovered and used for process heat, such as heating the reactor.

The process of FIG. 53 may thus be performed in a system having an optional grinder, a reactor, an ammonia collector, a solid/liquid separator, an optional density separator, an optional holding tank, a neutralization tank, another optional solid/liquid separator, a concentration tank, and an optional drier. These components may be connected to one another so as to allow processing of the protein source to liquid concentrate or dry product. Return loops may be included to allow further processing and/or reuse as needed. Heat exchangers to adjust temperature and allow reuse of process heat may also be included.

It will be readily understood that the conditions, machinery and other components of the systems and processes of the present invention may be interchanged with one another to produce variant protein solubilization processes and systems. For example, components described for one system or process may be used with another to digest a particular protein, achieve a desired product composition, aid in recycling and heat recovery, and to facilitate interchangeability between different systems.

EXAMPLES

The following examples are presented to illustrate and further describe selected embodiments of the present invention. They are not intended to literally represent the entire breadth of the invention. Variations upon these examples will be apparent to one skilled in the art and are also encompassed by the present invention.

In these Examples, equation and experiment numbers are intended to refer to equations and experiments within the indicated example only. Equations and experiments are not consecutively or similarly numbered among different examples.

Example 1

General Methods and Equipment

The following general methods and equations were used in the present examples:

The concentration of the different compounds in the liquid product and in raw materials was determined by two different procedures: Amino acid composition was determined by HPLC measurements (performed by the Laboratory of Protein Chemistry of Texas A&M University); total Kjeldhal nitrogen and mineral determinations were performed by the Extension Soil, Water and Forage Testing Laboratory of Texas A&M University using standard methodologies.

Measurement of digestibility of lignocellulosic material was done by the 3-d digestibility test using the DNS method. Biomass was ground to an adequate size if necessary. A Thomas-Wiley laboratory mill with several sieve sizes located in the Forest Science Research Center was used.

Lignin, cellulose, hemicellulose (holocellulose), ash, and moisture content of materials were determined using NREL methods.

Water baths and shaking air baths with thermocouples for temperature measurement and maintenance were used when required. Heating was also accomplished by tape and band heaters. Water and ice baths were used as cooling systems.

Figure 17:
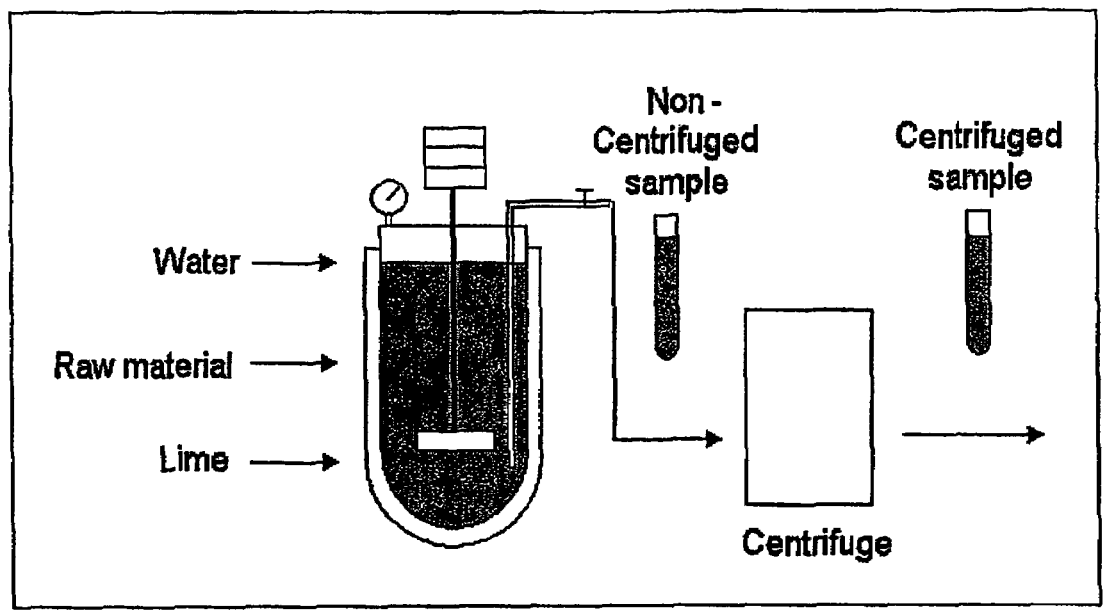
FIG. 17 illustrates an experimental setup for protein hydrolysis studies.

In general, the experiments in these examples were performed in a 1-L autoclave reactor with a temperature controller and a mixer powered by a variable-speed motor (FIG. 17). This reactor was pressurized with $N_2$ to obtain samples through the sampling port. A high mixing rate (~1000 rpm) was used to induce good contact between the suspended solids and the liquid.

Treatment conditions (for several organic materials) were systematically varied to explore the effect of the process variables—temperature, time, raw material concentration (g dry material/L), and calcium hydroxide loading (g $Ca(OH)_2$/g dry material)—on the protein hydrolysis. Samples were taken from the reactor at different times and centrifuged to separate the liquid phase from the residual solid material.

Equation 1 was used the conversion of the centrifuged sample, based on the initial Total Kjeldhal Nitrogen (TKN) of the organic material:

$$Conv_1 = \frac{V_{water} \times TKN_{centrifuged\ liquid}}{m_{dry\ sample} \times TKN_{dry\ sample}} \quad (1)$$

The liquid product was analyzed using two different methods to obtain the amino acid concentrations and the conversion of the reaction. The first method determined the total nitrogen content of the liquid sample using the modified micro-Kjeldhal method. Multiplication of nitrogen content (TKN) by 6.25 estimates the crude protein content. The second method used an HPLC to obtain the concentration of individual amino acids present in the sample. In this procedure, the sample was treated with hydrochloric acid (150° C., 1.5 h or 100° C., 24 h) to convert proteins and polypeptides into amino acids; this measurement is called Total Amino Acid Composition. The HPLC determination without the initial hydrolysis with HCl determines the Free Amino Acid composition.

Additional measurements included: final pH of liquid product, mass of soluble matter in the centrifuged liquid after evaporating water at 45° C., and mass of residual solid after drying at 105° C. This final measurement, the mass of residual solids, was determined by filtering the final mixture through a screen without further washing with water. The retained solids were dried at 105° C. The dry weight included not only the insoluble solids, but also soluble solids that were retained dissolved in residual solids.

Example 2

Protein Solubilization in Alfalfa Hay

Alfalfa hay is commonly used in ruminant nutrition. Higher feed digestibility ensures that animal requirements will be satisfied with less feed. Treatment of alfalfa hay generates two separate products: a highly digestible soluble fraction found in the liquid product, and a delignified residual solid.

Alfalfa hay was treated with calcium hydroxide, the least expensive base on the market. In Table 3, the composition of alfalfa in different states is summarized.

TABLE 3

Composition of alfalfa in its different states (McDonald et al., 1995)

| Alfalfa (% of dry mass) | Soluble | Crude protein | Lignin | Cellulose | Hemi-cellulose |
|---|---|---|---|---|---|
| Fresh early bloom | 60 | 19 | 7 | 23 | 2.9 |
| Mid bloom | 54 | 18.3 | 9 | 26 | 2.6 |
| Full bloom | 48 | 14 | 10 | 27 | 2.1 |
| Hay, sun-cured, early bloom | 58 | 18 | 8 | 24 | 2.7 |
| Mid bloom | 54 | 17 | 9 | 26 | 2.6 |
| Late bloom | 48 | 14 | 12 | 26 | 2.2 |
| Mature bloom | 42 | 12.9 | 14 | 29 | 2.2 |

Sun-cured alfalfa hay was obtained from the Producers Cooperative in Bryan, Tex.; then it was ground using a Thomas-Wiley laboratory mill (Arthur H. Thomas Company, Philadelphia, P A) and sieved through a 40-mesh screen. The moisture content, the total Kjeldhal nitrogen (estimate of the protein fraction), and the amino acid content were determined to characterize the starting material.

Raw alfalfa hay was 89.92% dry material and 10.08% moisture (Table 4). The TKN was 2.534% corresponding to a crude protein concentration in dry alfalfa of about 15.84% (Table 5). The remaining 84.16% corresponds to fiber, sugars, minerals and others. The amino acid composition for raw alfalfa hay is given in Table 6. The starting material contained a relatively well-balanced amino acid content (Table 6), with low levels of tyrosine.

TABLE 4

Moisture content of raw alfalfa hay

| Sample | Solid (g) | Dry solid (g) | Dry Solid (%) |
|---|---|---|---|
| 1 | 7.1436 | 6.4248 | 89.94 |
| 2 | 5.9935 | 5.3884 | 89.90 |
|  |  | Average | 89.92 |

TABLE 5

Protein and mineral content of raw alfalfa hay

| Sample | TKN (%) | P (%) | K (%) | Ca (%) | Mg (%) | Na (ppm) | Zn (ppm) | Fe (ppm) | Cu (ppm) | Mn (ppm) |
|---|---|---|---|---|---|---|---|---|---|---|
| 1 | 2.5492 | 0.2 | 2.27 | 1.8383 | 0.4591 | 6508 | 16 | 90 | 6 | 45 |
| 2 | 2.5181 | 0.2 | 2.16 | 17.865 | 0.4321 | 6176 | 16 | 94 | 5 | 42 |
| Mean | 2.5336 | 0.2 | 2.215 | 1.8124 | 0.4456 | 6342 | 16 | 92 | 5.5 | 43.5 |

TABLE 6

Amino acid composition of air-dried alfalfa hay

| Amino acid | Measured | Amino acid | Measured |
|---|---|---|---|
| ASP | 14.44 | TYR | 2.94 |
| GLU | 11.85 | VAL | 5.61 |
| SER | 6.13 | MET | 1.01 |
| HIS | 1.39 | PHE | 5.59 |
| GLY | 5.30 | ILE | 4.40 |
| THR | 4.95 | LEU | 10.06 |
| ALA | 5.63 | LYS | 5.77 |
| CYS | ND | TRP | ND |
| ARG | 5.58 | PRO | 9.35 |

ND: Not determined

Values in g AA/100 g total amino acids.

Experiment 1.

Temperature Effect

To determine the effect of temperature on solubilizing protein in alfalfa hay, experiments were run at different temperatures keeping the lime loading and alfalfa concentration constant (0.075 g lime/g alfalfa and 60 g dry alfalfa/L respectively). The experimental conditions studied and variables measured are summarized in Table 7.

TABLE 7

Experimental conditions and variables measured to determine the effect of temperature in protein solubilization of alfalfa hay

| | Temperature (° C.) | | | | |
|---|---|---|---|---|---|
| | 50 | 75 | 90 | 100 | 115 |
| Mass of alfalfa (g) | 56.7 | 53.4 | 56.7 | 56.7 | 56.7 |
| Volume of water (mL) | 850 | 800 | 850 | 850 | 850 |
| Mass of lime (g) | 4.3 | 4.0 | 4.3 | 4.3 | 4.3 |
| Initial temperature (° C.) | 50.3 | 73.2 | 94.1 | 93.1 | 105 |
| pH final | 11.1 | 11.3 | 10.7 | 9.9 | 9.85 |
| Residual solid (g) | 39.5 | 34.9 | 37 | 36.8 | 35 |
| Dissolved solids in 100 mL (g) | 2.6024 | 3.549 | 3.4995 | 3.6248 | 3.1551 |
| Protein in 100 mL (g) | 0.346 | 0.390 | 0.355 | 0.338 | 0.328 |
| Protein concentration (%) | 13.3 | 11.0 | 10.1 | 9.3 | 10.4 |

Table 8 shows the total nitrogen content in the centrifuged liquid samples as a function of time for the different temperatures. On the basis of the average TKN for dry alfalfa (2.53%), protein hydrolysis conversions were estimated (Table 9).

TABLE 8

Total Kjeldhal nitrogen content in the centrifuged liquid phase as a function of time for Experiment 1 (alfalfa hay)

| | Temperature | | | | |
|---|---|---|---|---|---|
| Time (min) | 50° C. | 75° C. | 90° C. | 100° C. | 115° C. |
| 0 | 0.0506 | 0.0503 | 0.0526 | 0.0576 | 0.0474 |
| 5 | 0.0520 | 0.0669 | 0.0609 | 0.0641 | 0.0620 |
| 10 | — | 0.0640 | — | — | — |
| 15 | 0.0609 | 0.0653 | 0.0637 | 0.0713 | 0.0756 |
| 30 | 0.0665 | 0.0655 | 0.0679 | 0.0813 | 0.0813 |
| 45 | 0.0692 | 0.0771 | 0.0719 | 0.0958 | 0.0955 |
| 60 | 0.0679 | 0.0771 | 0.0761 | 0.1039 | 0.0927 |
| 120 | — | 0.0778 | — | — | — |
| 150 | 0.0554 | — | 0.0568 | 0.0540 | 0.0525 |
| 180 | — | 0.0624 | — | — | — |

TKN in g nitrogen/100 g liquid sample.

TABLE 9

Percentage conversion of the total TKN to soluble TKN for Experiment 1 (alfalfa hay)

| | Temperature | | | | |
|---|---|---|---|---|---|
| Time (min) | 50° C. | 75° C. | 90° C. | 100° C. | 115° C. |
| 0 | 33.5 | 33.3 | 34.8 | 38.2 | 31.4 |
| 5 | 34.4 | 44.3 | 40.3 | 42.5 | 41.1 |
| 10 | — | 42.4 | — | — | — |
| 15 | 40.3 | 43.2 | 42.2 | 47.2 | 50.1 |
| 30 | 44.0 | 43.4 | 45.0 | 53.9 | 53.9 |
| 45 | 45.8 | 51.0 | 47.6 | 63.5 | 63.3 |
| 60 | 45.0 | 51.0 | 50.4 | 68.8 | 61.4 |
| 120 | — | 51.5 | — | — | — |
| 150 | 36.7 | — | 37.6 | 35.8 | 34.8 |
| 180 | — | 41.3 | — | — | — |

The final product of protein hydrolysis is individual amino acids, which react with the hydroxyl, consume lime, and decrease the pH. This explains the lower pH obtained for high protein conversions (Tables 7 and 9).

The similar initial conversion for all temperatures can be explained by the high fraction of soluble components in alfalfa (approximately 50%, see Table 3). The final conversion, lower than the rest, is explained by the different sampling method. All early samples were taken from the reactor through the sampling port at the internal temperature. For the final sample, the fluid was cooled down to 35° C., the nitrogen pressure was released and the solids were filtered before the sample was taken. The sampling procedure for the final sample was altered to measure more variables. This same procedure was followed for the other experiments.

Highly soluble alfalfa components are present in the dissolved solids. Table 7 shows that at 75° C., the protein concentration in the solid remaining after liquid evaporation is approximately 11%. Although, this is actually lower than the protein content in the raw alfalfa, the processing steps convert protein into highly digestible amino acids, and these amino acids are mixed with other highly digestible alfalfa components increasing the nutritional value of the final product.

Figure 18:
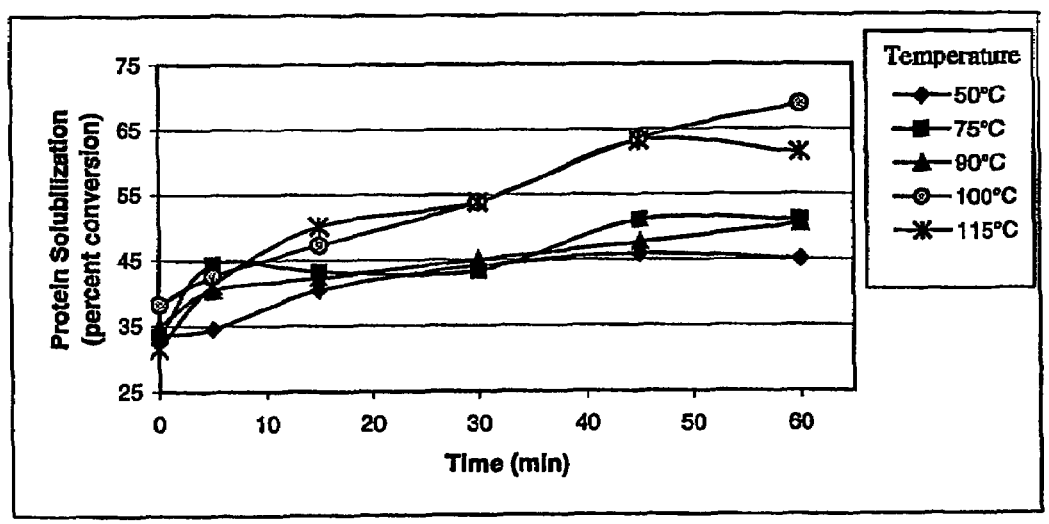
FIG. 18 is a graph illustrating the temperature effect on protein solubilization of alfalfa hay.

FIG. 18 presents the protein hydrolysis (percent conversion) as a function of time for the different temperatures studied. The conversion increases at higher temperatures. The conversion for 100° C. is similar to the one obtained at 115° C.; therefore, the lower temperature is favored because the amino acids should degrade less, the energy required is less, and the working pressure is lower.

Experiment 2.

Lime Loading Effect

To determine the effect of lime loading on protein solubilization of alfalfa hay, experiments were run at different lime/alfalfa ratios keeping the temperature and alfalfa concentration constant (75° C. and 40 g dry alfalfa/L respectively). The experimental conditions studied and variables measured are summarized in Table 10.

Again, the initial conversions are similar for all lime loadings because of the highly soluble components present in the alfalfa (approximately 50%, see Table 3). The final conversion (150 min) for the experiment at 0.2 g lime/g alfalfa differed from the others because it increased whereas the others decreased. In the case of 0.2 g lime/g alfalfa, the final sample was taken through the sampling port, whereas the final sample for the other loadings was taken by opening the reactor and removing the sample.

TABLE 10

Experimental conditions and variables measured to determine the lime loading effect in protein solubilization of alfalfa hay

| | Lime loading (g lime/g alfalfa) | | | | | |
|---|---|---|---|---|---|---|
| | 0 | 0.05 | 0.075 | 0.1 | 0.2 | 0.4 |
| Mass of alfalfa (g) | 37.8 | 37.8 | 37.8 | 37.8 | 37.8 | 37.8 |
| Volume of water (mL) | 850 | 850 | 850 | 850 | 850 | 850 |
| Mass of lime (g) | 0 | 1.9 | 2.9 | 3.8 | 7.6 | 15.2 |
| Temperature (° C.) | 75 | 75 | 75 | 75 | 75 | 75 |
| Initial Temperature (° C.) | 78.1 | 71.2 | 78.2 | 58.3 | 80.3 | 81.5 |
| pH final | 5.7 | 10 | 10.7 | — | 11.4 | 11.2 |
| Residual solid (g) | 23.5 | 24.1 | 22.8 | 20.3 | 23.7 | 29.5 |
| Dissolved solids in 100 mL (g) | 1.3489 | 1.8645 | 2.0201 | 1.9289 | 1.9215 | 2.1651 |
| Protein in 100 mL (g) | 0.286 | 0.249 | 0.231 | 0.267 | 0.264 | 0.251 |

Table 11 shows the total nitrogen content in the centrifuged liquid samples as a function of time for the different temperatures.

TABLE 11

Total Kjeldhal nitrogen content in the centrifuged liquid phase as a function of time for Experiment 2 (alfalfa hay)

| | Lime loading | | | | | |
|---|---|---|---|---|---|---|
| Time (min) | 0 g/g | 0.05 g/g | 0.075 g/g | 0.1 g/g | 0.2 g/g | 0.4 g/g |
| 0 | 0.0360 | 0.0364 | 0.0353 | 0.0370 | 0.0319 | 0.0345 |
| 5 | 0.0401 | 0.0394 | 0.0370 | 0.0392 | 0.0394 | 0.0373 |
| 15 | 0.0457 | 0.0423 | 0.0377 | 0.0427 | 0.0423 | 0.0401 |
| 30 | 0.0457 | 0.0452 | 0.0451 | 0.0441 | 0.0423 | 0.0450 |
| 45 | 0.0485 | 0.0466 | 0.0488 | 0.0462 | 0.0481 | 0.0457 |
| 60 | 0.0485 | 0.0511 | 0.0510 | 0.0478 | 0.0481 | 0.0498 |
| 150 | 0.0457 | 0.0394 | 0.0370 | 0.0427 | 0.0554 | 0.0401 |

TKN in g nitrogen/100 g liquid sample.

On the basis of the average TKN for dry alfalfa hay (2.53%), the protein hydrolysis conversions were estimated and are given in Table 12.

TABLE 12

Percentage conversion of the total TKN to soluble TKN for Experiment 2 (alfalfa hay)

| | Lime loading | | | | | |
|---|---|---|---|---|---|---|
| Time (min) | 0 g/g | 0.05 g/g | 0.075 g/g | 0.1 g/g | 0.2 g/g | 0.4 g/g |
| 0 | 35.7 | 36.1 | 35.0 | 36.7 | 31.6 | 34.2 |
| 5 | 39.8 | 39.1 | 36.7 | 38.9 | 39.1 | 37.0 |
| 15 | 45.3 | 41.9 | 37.4 | 42.3 | 41.9 | 39.8 |
| 30 | 45.3 | 44.8 | 44.7 | 43.7 | 41.9 | 44.6 |
| 45 | 48.1 | 46.2 | 48.4 | 45.8 | 47.7 | 45.3 |
| 60 | 48.1 | 50.7 | 50.6 | 47.4 | 47.7 | 49.4 |
| 150 | 45.3 | 39.1 | 36.7 | 42.3 | 54.9 | 39.8 |

Figure 19:
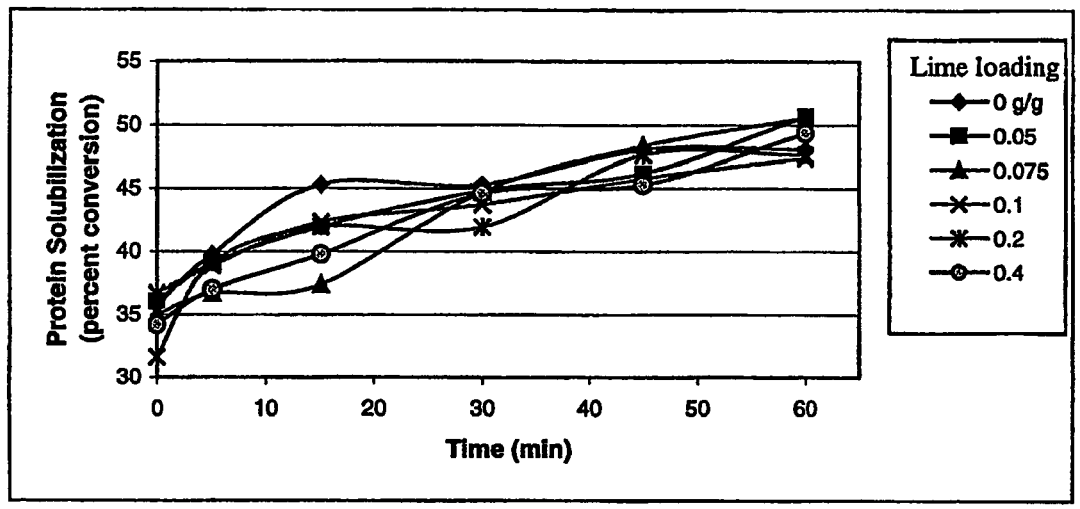
FIG. 19 is a graph illustrating the lime loading effect on protein solubilization in alfalfa hay.

FIG. 19 presents the protein solubilized (percent conversion) as a function of time for the different lime loadings studied. The conversion is similar for all lime loadings, even for the experiment with no lime. This behavior is related to the highly soluble contents in the alfalfa hay.

In the no-lime experiment, there is soluble protein present in the water phase; however, hydroxyl groups are dilute so no reaction occurred in the solid phase or the solid-liquid interface. A smaller amount of free amino acids were present because the hydrolysis reaction is likely to be slower under these conditions. The final pH was 5.7; likely, the pH became acidic because of acids (e.g., acetyl groups) released from the biomass and from amino acids released from the proteins. Because no lime was used, the concentration of dissolved solids was lower. In all the other cases, in Table 10, lime was a portion of the dissolved solids.

FIG. 19 shows that lime loading has no significant effect on the protein solubilization of alfalfa hay. A minimum lime loading might be recommended to avoid acid hydrolysis of protein, which tends to be more damaging than alkaline hydrolysis. This lime loading would result in a higher concentration of free amino acids in the liquid product.

Experiment 3.

Alfalfa Concentration Effect

To determine the effect of the initial alfalfa concentration on protein solubilization of alfalfa hay, experiments were run at different alfalfa concentrations keeping the temperature and lime loading constant (75° C. and 0.075 g lime/g alfalfa respectively). The experimental conditions studied and variables measured are summarized in Table 13.

TABLE 13

Experimental conditions and variables measured for determining the effect of initial alfalfa concentration in protein solubilization

| | Alfalfa concentration (g dry alfalfa/L) | | | |
|---|---|---|---|---|
| | 20 | 40 | 60 | 80 |
| Mass of alfalfa (g) | 18.9 | 37.8 | 53.4 | 75.6 |
| Volume of water (mL) | 850 | 850 | 800 | 850 |
| Mass of lime (g) | 1.5 | 2.9 | 4.0 | 5.7 |
| Temperature (° C.) | 75 | 75 | 75 | 75 |
| Initial temperature (° C.) | 78.1 | 78.2 | 73.2 | 82.1 |
| pH final | 10.7 | 10.7 | 11.3 | 11 |
| Residual solid (g) | 9.7 | 22.8 | 34.9 | 53.3 |
| Dissolved solids in 100 mL (g) | 1.0072 | 2.0201 | 3.549 | 4.1349 |
| Protein in 100 mL(g) | 0.154 | 0.231 | 0.390 | 0.450 |

Table 14 shows the total nitrogen content in the centrifuged liquid samples as a function of time for the different alfalfa concentrations. On the basis of the average TKN for dry alfalfa (2.53%), the protein hydrolysis conversions were estimated and are given in Table 15.

TABLE 14

Total Kjeldhal nitrogen content in the centrifuged liquid phase as a function of time for Experiment 3 (alfalfa hay)

| | Alfalfa concentration | | | |
|---|---|---|---|---|
| Time (min) | 20 g/L | 40 g/L | 60 g/L | 80 g/L |
| 0 | 0.0175 | 0.0353 | 0.0503 | 0.0514 |
| 5 | 0.0182 | 0.0370 | 0.0669 | 0.0571 |
| 10 | — | — | 0.0640 | — |
| 15 | 0.0204 | 0.0377 | 0.0653 | 0.0770 |
| 30 | 0.0211 | 0.0451 | 0.0655 | 0.0727 |
| 45 | 0.0218 | 0.0488 | 0.0771 | 0.0946 |
| 60 | 0.0218 | 0.0510 | 0.0771 | 0.0883 |
| 120 | — | — | 0.0778 | — |
| 150 | 0.0247 | 0.0370 | — | 0.0720 |
| 180 | — | — | 0.0624 | — |

TKN in g nitrogen/100 g liquid sample.

TABLE 15

Percentage conversion of the total TKN to soluble TKN for Experiment 3 (alfalfa hay)

| | Alfalfa concentration | | | |
|---|---|---|---|---|
| Time (min) | 20 g/L | 40 g/L | 60 g/L | 80 g/L |
| 0 | 34.6 | 35.0 | 33.3 | 25.6 |
| 5 | 36.0 | 36.7 | 44.3 | 28.4 |
| 10 | — | — | 42.4 | — |
| 15 | 40.4 | 37.4 | 43.2 | 38.3 |
| 30 | 41.8 | 44.7 | 43.4 | 36.2 |
| 45 | 43.1 | 48.4 | 51.0 | 47.1 |
| 60 | 43.1 | 50.6 | 51.0 | 44.0 |
| 120 | — | — | 51.5 | — |
| 150 | 48.9 | 36.7 | — | 35.8 |
| 180 | — | — | 41.3 | — |

The final conversion (150 min) for the experiment at 20 g alfalfa/L differed from the others because it increased whereas the others decreased. In the case of 20 g alfalfa/L, the final sample was taken through the sampling port, whereas the final sample for the other concentrations was taken by opening the reactor and removing the sample.

Figure 20:
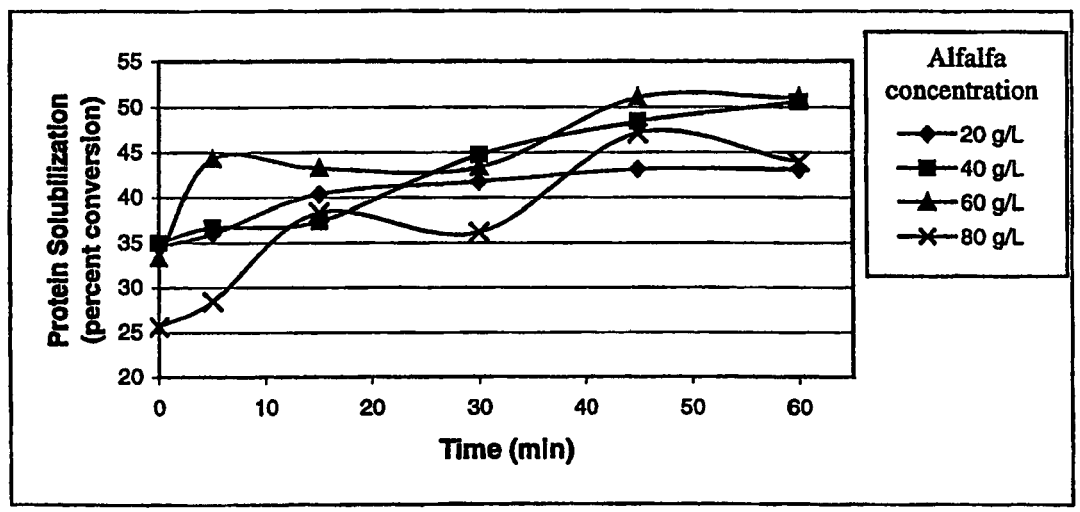
FIG. 20 is a graph illustrating the effect of alfalfa hay concentration on protein solubilization.

FIG. 20 presents the protein solubilization (percent conversion) as a function of time for the different alfalfa concentrations studied. The conversion increases as alfalfa concentration increases, until it reaches a maximum between 60 and 80 g/L; at this point, because the mass of lime and alfalfa is very high, it was difficult for the alfalfa to contact the liquid phase, which decreased the conversion. The conversions for 80 g/L are similar to the ones obtained for 20 g/L. Also, the conversions for 40 and 60 g/L are similar. As Table 13 shows, the dissolved solids are higher for the higher alfalfa concentration.

Experiment 4.

Statistical Analysis

To determine if relationships are present between the variables studied in the protein solubilization of alfalfa hay, an additional $2^3$ factorial experiment was run, using temperature, lime loading, and alfalfa loading as variables, and the TKN solubilization (conversion) at 60 minutes as the response variable. The conditions studied are summarized in Table 16, as well as the conversion obtained for each experiment.

TABLE 16

Experimental conditions studied in the $2^3$ factorial experimental design

| Condition | Var 1 Temperature (° C.) | Var 2 Lime loading (g lime/g solid) | Var 3 Alfalfa concentration (g/L) | Y Conversion (%) |
|---|---|---|---|---|
| 1 | 75 | 0.075 | 40 | 50.6 |
| 2 | 100 | 0.075 | 40 | 53.9 |
| 3 | 75 | 0.1 | 40 | 47.4 |
| 4 | 100 | 0.1 | 40 | 58.6 |
| 5 | 75 | 0.075 | 60 | 51.0 |
| 6 | 100 | 0.075 | 60 | 68.8 |
| 7 | 75 | 0.1 | 60 | 60.4 |
| 8 | 100 | 0.1 | 60 | 67.3 |

Using the response variable, a Yates algorithm was performed with the conversion values to obtain the mean, the variable effect, and the interaction between the studied variables. This information is summarized in Table 17. To determine the variability of the measurement, Conditions I and 5 were repeated in triplicate (Table 18).

TABLE 17

Yates algorithm results (Milton and Arnold, 1990)

| Column 1 | Column 2 | Column 3 | Yates Results | Interpretation of Yates Results |
|---|---|---|---|---|
| 104.49 | 210.48 | 458.00 | 57.25 | Mean |
| 105.98 | 247.52 | 39.32 | 9.83 | E1 (Effect of Variable 1) |
| 119.87 | 14.58 | 9.27 | 2.32 | E2 (Effect of Variable 2) |
| 127.65 | 24.74 | −3.00 | −0.75 | I12 (Interaction of Variables 1 and 2) |
| 3.37 | 1.49 | 37.04 | 9.26 | E3 (Effect of Variable 3) |
| 11.20 | 7.78 | 10.16 | 2.54 | I13 (Interaction of Variables 1 and 3) |
| 17.79 | 7.83 | 6.29 | 1.57 | I23 (Interaction of Variables 2 and 3) |
| 6.96 | −10.83 | −18.66 | −4.67 | I123 (Interaction of Variables 1, 2 and 3) |

TABLE 18

Standard deviation calculations and results

| Condition | First rep. | Second rep. | Third rep. | Mean |
|---|---|---|---|---|
| 5 | 54.68 | 47.66 | 51.04 | 51.13 |
| 1 | 51.95 | 50.56 | 55.12 | 52.55 |
|  | $S^2$ | 8.891 | $S_E$ | 1.491 |

In Table 18, the variance ($S^2$) was calculated as the mean variance of both conditions studied. Then $S_E$, standard deviation of variable effects, was estimated with the mean variance for four values (the effect and interactions in a $2^3$ factorial are the mean value of four calculations). Given four degrees of freedom and 99% confidence, the t-student value is 3.747. Then, multiplying this t-value by $S_E$ (1.491) gives the limits of non-significant effects in the Yates results column (−5.59 and 5.59).

From Table 17, the only significant effects are the ones from Variable 1 (temperature, E1=9.83>5.59) and Variable 3 (alfalfa concentration, E3=9.26>5.59). This is consistent with the observations made in Experiments 1 and 3. From the values obtained in the factorial design, the presence of non-significant variable interactions implies that the effect of temperature and alfalfa concentration are additive, giving the highest conversion when both variables are high. This analysis cannot be readily extrapolated to higher temperatures and concentrations (as seen from Experiment 3), because different phenomena can occur at other conditions.

There is no significant effect of lime loading on the solubilization of protein from alfalfa hay (E2=2.32<5.59), and this variable does not interact with the other variables (I12 and I23<5.59); therefore, the lime loading may be based solely on preventing acid hydrolysis of protein to amino acids, rather than protein solubilization. The conversion only represents the presence of nitrogen (protein) in the liquid product, not individual hydrolyzed amino acids.

A comparison between the compositions of the raw material and the residual solid gives information on the effectiveness of lime treating alfalfa for protein solubilization. The composition for both materials is shown in Table 19. These results were obtained for Condition 5 of the factorial design (75° C., 0.075 g lime/g alfalfa and 60 g alfalfa/L).

TABLE 19

Comparison of protein and minerals content present in the raw alfalfa hay and the residual solid after lime treatment

| Sample | TKN (%) | P (%) | K (%) | Ca (%) | Mg (%) | Na (%) | Zn (%) | Fe (%) | Cu (%) | Mn (%) |
|---|---|---|---|---|---|---|---|---|---|---|
| Dry Alfalfa | 2.5336 | 0.20 | 2.21 | 1.8124 | 0.4456 | 5342 | 16 | 92 | 5.5 | 43.5 |
| Residual Solid | 2.2383 | 0.18 | 1.42 | 3.3554 | 0.4166 | 3969 | 71 | 137 | 17 | 37 |

Table 19 shows that the calcium concentration of the residual solids is greater than in the raw alfalfa. This value increases due to the lime added for the treatment, which is not completely soluble in water. The values for potassium and sodium decrease during the lime treatment due to the high solubility of these salts. The nitrogen present in the residual solid is similar to the value obtained for the raw material before lime treatment. This implies that the concentration of nitrogen in the solubles is similar to the concentration in the raw material.

The fraction of alfalfa that was solubilized in Condition 5 was calculated as follows:

soluble fraction=1−{32.5 g residual solids−[(3.55 g dissolved solids/100 mL liquid)*200 mL moisture]}/53.4 g initial alfalfa=0.524 g solubilized/g of alfalfa.

This calculation corrects for the dissolved solids contained in the 200 mL of liquid. This value (0.524 g solubilized/g alfalfa) is reported in Table 20.

TABLE 20

Variables measured for Condition 5

| Mass of alfalfa (g) | 53.4 | pH final | 11.3 |
|---|---|---|---|
| Volume of water (mL) | 800 | Residual solid (g) | 32.5 |
| Mass of lime (g) | 4.0 | Dissolved solids in 100 mL (g) | 3.55 |
| Temperature (° C.) | 75 | Soluble fraction of alfalfa | 0.524 |

Experiment 5.

Amino Acid Analysis

Alfalfa hay was treated with lime for 60 min and 24 h with the recommended conditions: 100° C., 0.075 g lime/g alfalfa and 60 g alfalfa/L. The amino acid analysis was performed in three different ways:

1) Centrifuged liquid product-Free amino acid analysis. The analysis was made without extra HCl hydrolysis of the sample. No amino acids were destroyed by the analytical procedure, but soluble polypeptides are missed in the analysis.
2) Centrifuged liquid product-Total amino acid analysis. The analysis was made with 24-h HCl hydrolysis of the liquid sample. Some amino acids were destroyed by the analytical procedure or converted to other amino acids; soluble polypeptides are measured in the analysis.
3) Dry product after evaporating water from the centrifuged liquid. Because this sample was solid, HCL hydrolysis was required. Some amino acids (asparagine, glutamine, and tryptophan) were destroyed by the acid and could not be measured.

Tables 21 and 22 show the free amino acids and the total amino acids concentration for lime treated alfalfa at 60 min and 24 h, respectively. Table 23 shows the protein and mineral content for both samples.

TABLE 21

Free and total amino acid concentration for the centrifuged liquid product of lime-hydrolyzed alfalfa hay at 60 min

| Amino acid | Non hydrolyzed-free amino acids | | Hydrolyzed-total amino acids | |
|---|---|---|---|---|
| | Concentration (mg/L) | Percentage (%) | Concentration (mg/L) | Percentage (%) |
| ASN | 165.87 | 17.17 | 0.00 | 0.00 |
| GLN | 0.00 | 0.00 | 0.00 | 0.00 |
| ASP | 54.30 | 5.62 | 334.81 | 23.04 |
| GLU | 109.11 | 11.29 | 155.35 | 10.69 |
| SER | 44.87 | 4.64 | 78.72 | 5.42 |
| HIS | 0.00 | 0.00 | 0.00 | 0.00 |
| GLY | 44.50 | 4.61 | 86.83 | 5.98 |
| THR | 18.97 | 1.96 | 43.65 | 3.00 |
| ALA | 37.34 | 3.87 | 76.42 | 5.26 |
| ARG | 77.27 | 8.00 | 110.28 | 7.59 |
| TYR | 0.00 | 0.00 | 18.68 | 1.29 |
| CYS | 36.57 | 3.79 | ND | 0.00 |
| VAL | 39.31 | 4.07 | 71.03 | 4.89 |
| MET | 4.68 | 0.48 | 0.00 | 0.00 |
| PHE | 9.20 | 0.95 | 47.82 | 3.29 |
| ILE | 22.62 | 2.34 | 39.62 | 2.73 |
| LEU | 27.35 | 2.83 | 64.06 | 4.41 |
| LYS | 5.58 | 0.58 | 31.22 | 2.15 |

TABLE 21-continued

Free and total amino acid concentration for the centrifuged liquid product of lime-hydrolyzed alfalfa hay at 60 min

| Amino acid | Non hydrolyzed-free amino acids | | Hydrolyzed-total amino acids | |
|---|---|---|---|---|
| | Concentration (mg/L) | Percentage (%) | Concentration (mg/L) | Percentage (%) |
| TRP | 18.81 | 1.95 | ND | 0.00 |
| PRO | 249.78 | 25.85 | 294.47 | 20.27 |
| Total | 966.15 | 100 | 1452.95 | 100 |

TABLE 22

Free and total amino acid concentration for the centrifuged liquid product from lime-hydrolyzed alfalfa hay at 24 h

| Amino acid | Non hydrolyzed-free amino acids | | Hydrolyzed-total amino acids | |
|---|---|---|---|---|
| | Concentration (mg/L) | Percentage (%) | Concentration (mg/L) | Percentage (%) |
| ASN | 76.10 | 8.07 | 0.00 | 0.00 |
| GLN | 0.00 | 0.00 | 0.00 | 0.00 |

TABLE 22-continued

Free and total amino acid concentration for the centrifuged liquid product from lime-hydrolyzed alfalfa hay at 24 h

| Amino acid | Non hydrolyzed-free amino acids | | Hydrolyzed-total amino acids | |
|---|---|---|---|---|
| | Concentration (mg/L) | Percentage (%) | Concentration (mg/L) | Percentage (%) |
| ASP | 70.26 | 7.45 | 239.79 | 17.51 |
| GLU | 116.33 | 12.33 | 157.16 | 11.47 |
| SER | 38.93 | 4.13 | 76.64 | 5.59 |
| HIS | 0.00 | 0.00 | 0.00 | 0.00 |
| GLY | 96.01 | 10.18 | 141.65 | 10.34 |
| THR | 9.48 | 1.00 | 37.28 | 2.72 |
| ALA | 37.19 | 3.94 | 74.06 | 5.41 |
| ARG | 75.25 | 7.98 | 93.55 | 6.83 |
| TYR | 0.00 | 0.00 | 8.43 | 0.62 |
| CYS | 35.66 | 3.78 | ND | 0.00 |
| VAL | 38.89 | 4.12 | 66.17 | 4.83 |
| MET | 0.00 | 0.00 | 0.00 | 0.00 |
| PHE | 10.48 | 1.11 | 48.45 | 3.54 |
| ILE | 21.90 | 2.32 | 39.84 | 2.91 |
| LEU | 25.95 | 2.75 | 60.90 | 4.45 |
| LYS | 0.00 | 0.00 | 26.76 | 1.95 |
| TRP | 17.56 | 1.86 | ND | 0.00 |
| PRO | 273.28 | 28.97 | 299.16 | 21.84 |
| Total | 943.24 | 100.00 | 1369.82 | 100.00 |

TABLE 23

Comparison of protein and minerals content present in the centrifuged liquid of lime-treatment of alfalfa hay

| Sample | TKN (%) | P (%) | K (%) | Ca (%) | Mg (%) | Na (ppm) | Zn (ppm) | Fe (ppm) | Cu (ppm) | Mn (ppm) |
|---|---|---|---|---|---|---|---|---|---|---|
| 60 min | 0.0742 | 0.0062 | 0.149 | 0.2342 | 0.027 | 538 | 2 | 4 | 0 | 2 |
| 24 h | 0.0926 | 0.0082 | 0.155 | 0.2342 | 0.031 | 518 | 2 | 6 | 0 | 2 |

For all the experiments, the centrifuged liquid contained a very high concentration of suspended particulate matter that might be measured in the Kjeldhal determination but not in the amino acid analysis. This explains the difference between the amino acid determination and the estimated protein concentration using Kjeldhal analysis (1.45 vs. 4.64 and 1.37 vs. 5.79 g protein/L).

A comparison of Tables 21-23 shows that although the nitrogen concentration increases from 60 min to 24 h, the total amino concentration remains relatively constant, so there is no need for a long treatment in the hydrolysis of alfalfa hay.

Finally, the amino acid composition of the products was compared to the needed essential amino acids of various domestic animals.

Table 24 shows the amino acid composition of dry product and liquid product (both free amino acids and total amino acids—Table 21). The amino acid composition of lime-hydrolyzed alfalfa hay at 60 min is not well balanced with respect to the essential amino acid requirements of different monogastric domestic animals. There are particularly low values for histidine, threonine, methionine and lysine; some other amino acids are sufficient for the majority of animals, but not all (threonine, tyrosine). Lime hydrolysis of alfalfa hay generates a product that is very rich in proline and asparagine, but these are not essential amino acids in the diet of domestic animals.

TABLE 24

Amino acid analysis of product and essential amino acids requirements for various domestic animals (alfalfa hay)

| Amino Acid | Cat-fish | Dogs | Cats | Chick-ens | Pigs | Dry Product | Liquid (FAA) | Raw Alfalfa |
|---|---|---|---|---|---|---|---|---|
| ASN | | | | | | | 17.17 | |
| GLN | | | | | | | 0.00 | |
| ASP | | | | | | 7.52 | 5.62 | 14.44 |
| GLU | | | | | | 11.40 | 11.29 | 11.85 |
| SER | | | | | | 5.32 | 4.64 | 6.13 |
| HIS | 1.31 | 1.00 | 1.03 | 1.40 | 1.25 | 0.71 | 0.00 | 1.39 |
| GLY | | | | | | 6.50 | 4.61 | 5.30 |
| THR | 1.75 | 2.64 | 2.43 | 3.50 | 2.50 | 2.53 | 1.96 | 4.95 |
| ALA | | | | | | 4.55 | 3.87 | 5.63 |
| ARG | 3.75 | 2.82 | 4.17 | 5.50 | 0.00 | 6.36 | 8.00 | 5.58 |
| VAL | 2.63 | 2.18 | 2.07 | 4.15 | 2.67 | 9.00 | 4.07 | 5.61 |
| CYS | 2.00* | 2.41* | 3.67* | 4.00* | 1.92* | 6.36 | 3.79 | ND |
| MET | 2.00* | 2.41* | 2.07 | 2.25 | 1.92* | 0.95 | 0.48 | 1.01 |
| TYR | 4.38+ | 4.05+ | 2.93+ | 5.85+ | 3.75+ | 2.78 | 0.00 | 2.94 |
| PHE | 4.38+ | 4.05+ | 1.40 | 3.15 | 3.75+ | 5.53 | 0.95 | 5.59 |
| ILE | 2.28 | 2.05 | 1.73 | 3.65 | 2.50 | 5.54 | 2.34 | 4.40 |
| LEU | 3.06 | 3.27 | 4.17 | 5.25 | 2.50 | 10.77 | 2.83 | 10.06 |
| LYS | 4.47 | 3.50 | 4.00 | 5.75 | 3.58 | 1.49 | 0.58 | 5.77 |
| TRP | 0.44 | 0.91 | 0.83 | 1.05 | 0.75 | ND | 1.95 | ND |
| PRO | | | | | | 12.70 | 25.85 | 9.35 |

*Cysteine + Methionine
+Tyrosine + Phenylalanine
FAA Free Amino Acids
All values are in g amino acid/100 g protein.

Differences between the two liquid samples (free vs. total amino acids) can be explained by acid degradation of some amino acids (especially tryptophan, asparagine and glutamine) in the total amino acid determination. Also, some protein in the centrifuged liquid may not have been hydrolyzed by the lime and may have been present as soluble polypeptides that were not detected by the HPLC analysis. The difference between the total amino acid in the liquid sample and the dry product is explained by the high concentration of suspended matter present in the liquid sample (centrifugation at 3500 rpm for 5 min). This suspended matter was not determined during the total amino acid measurement because the first step before HCL hydrolysis is centrifugation at 15000 rpm. The suspended matter forms an important part of the dry product and this explains the very different result for the amino acid composition.

The highest protein solubilization for alfalfa (68%) was achieved using 60 minutes, 0.075 g $Ca(OH)_2$/g alfalfa, 100° C., and 60 g dry alfalfa/L. Protein solubilization increases with temperature; a higher initial concentration of alfalfa increases the conversion up to a limit between 60 and 80 g alfalfa/L.

Because of the high solubility of alfalfa components, protein solubilized was high and did not change dramatically for all the cases studied (43% to 68%). Lime loading has the least effect of the four variables studied, but some lime is required to prevent acids naturally present in the alfalfa from damaging the amino acids, and to obtain a higher ratio of free amino acids in the final product. Finally, the amino acid composition of the product compares poorly with the essential amino acid requirements for various monogastric domestic animals. The product is low in histidine (underestimated in the analysis), threonine, methionine, and lysine. It is especially rich in asparagine and proline, but these are not required in the animal diets. The protein product is most suited for ruminants.

Lime treatment increases the digestibility of the holocellulose fraction (Chang et al., 1998), providing added value to the residual solid from the thermo-chemical treatment. The use of both products as a ruminant feed ensures a more efficient digestion when compared to the initial material.

Example 3

Protein Solubilization in Soybean Hay

Soybeans are normally harvested for the generation of several food products. During the harvesting process, an unused waste product is generated in large quantities.

Additionally, some special weather conditions (e.g. long dry season, long rainy season) hamper soybean growth. A low crop yield directs the soybean harvest to the generation of animal feed (soybean hay), instead of the food industry.

Treatment of soybean hay will generate two separate products: a highly digestible soluble fraction and a delignified residual solid. The higher feed digestibility ensures that animal requirements will be satisfied with less feed.

Sun-cured soybean hay (i.e., leaves, stems, and beans of mowed soybean plants) was obtained from Terrabon Company; then it was ground using a Thomas-Wiley laboratory mill (Arthur H. Thomas Company, Philadelphia, P A) and sieved through a 40-mesh screen. The moisture content, the total nitrogen (estimate of the protein fraction), and the amino acid content were determined to characterize the starting material.

In Table 25, the composition of the soybeans in its different states is summarized.

TABLE 25

Composition of soybeans in its different states (McDonald et al., 1995)

| Soybeans | Crude Fiber (g/kg) | Crude Protein (g/kg) | Digestible Crude Protein (g/kg) | Starch and Sugar |
|---|---|---|---|---|
| Soybean meal | 58 | 503 | — | 124 |
| Soybean meal, full fat | 48 | 415 | — | 91 |
| Hay, sun-cured | 366 | 156 | 101 | — |

Soybean hay was 91.31% dry material and 8.69% moisture (Table 26). The TKN was 3.02% corresponding to a crude protein concentration in dry soybean hay of about 19% (Table 27). The remaining 81% corresponds to fiber, sugars, minerals, and others. The amino acid composition for raw alfalfa hay is given in Table 28.

TABLE 26

Moisture content of air-dried soybean hay

| Sample | Solid (g) | Dry Solid (g) | Dry solid (%) |
|---|---|---|---|
| 1 | 5.1781 | 4.7297 | 91.34 |
| 2 | 5.5824 | 5.0967 | 91.30 |
| 3 | 5.4826 | 5.0048 | 91.29 |
| | | Average | 91.31 |

TABLE 27

Protein and mineral content of air-dried soybean hay

| Sample | TKN (%) | P (%) | K (%) | Ca (%) | Mg (%) | Na (ppm) | Zn (ppm) | Fe (ppm) | Cu (ppm) | Mn (ppm) |
|---|---|---|---|---|---|---|---|---|---|---|
| Raw Soy | 3.0183 | 0.37 | 2.24 | 1.6477 | 0.3606 | 1399 | 34 | 280 | 13 | 53 |

TABLE 28

Amino acid composition of air-dried soybean hay

| Amino acid | Measured | Amino acid | Measured |
|---|---|---|---|
| ASP | 16.79 | TYR | 2.82 |
| GLU | 15.10 | VAL | 4.85 |
| SER | 5.65 | MET | 0.88 |
| HIS | 2.55 | PHE | 5.36 |
| GLY | 4.46 | ILE | 4.27 |
| THR | 4.23 | LEU | 9.32 |
| ALA | 4.82 | LYS | 5.93 |
| CYS | ND | TRP | ND |
| ARG | 7.75 | PRO | 5.21 |

ND: Not determined
Values in g AA/100 g total amino acids.

Experiment 1.

Repeatability of the Results

To determine the repeatability of the results on solubilizing protein in soybean hay, experiments were run at the same conditions: temperature, lime loading, and soybean hay concentration (100° C., 0.05 g lime/g soybean hay and 60 g dry soybean hay/L respectively). The experimental conditions studied and variables measured are summarized in Table 29.

TABLE 29

Experimental conditions and variables measured to determine the repeatability of results in protein solubilization of soybean hay

| Experiment | B | E | J | K |
|---|---|---|---|---|
| Mass of soybean hay (g) | 55.9 | 55.9 | 55.9 | 55.9 |
| Volume of water (mL) | 850 | 850 | 850 | 850 |
| Mass of lime (g) | 2.8 | 2.8 | 2.8 | 2.8 |
| Initial temperature (° C.) | 93 | 93.5 | 105 | 98.1 |
| pH final | 8.6 | 8.9 | 8.6 | 8.9 |
| Residual solid (g) | 35.3 | 36.8 | 37 | 35.4 |
| Dissolved solids in 100 mL (g) | 2.5706 | 2.3927 | 2.7449 | 2.7116 |
| Protein in 100 mL (g) | 0.770 | 0.799 | 0.837 | 0.779 |

Table 30 shows the total nitrogen content in the centrifuged liquid samples as a function of time for the same conditions of temperature, lime loading, and soybean hay concentration. On the basis of the average TKN for dry soybean hay (3.02%), protein hydrolysis conversions were estimated (Table 31).

TABLE 30

Total Kjeldhal nitrogen content in the centrifuged liquid phase as a function of time for Experiment 1 (soybean hay)

| Time (min) | B | E | J | K |
|---|---|---|---|---|
| 0 | 0.0808 | 0.0741 | 0.0799 | 0.0831 |
| 5 | 0.0768 | 0.0837 | 0.0837 | 0.0876 |
| 15 | 0.0916 | 0.0876 | 0.0965 | 0.0996 |
| 30 | 0.1002 | 0.0939 | 0.1028 | 0.1078 |
| 45 | 0.1068 | 0.0977 | 0.1084 | 0.1203 |
| 60 | 0.1008 | 0.1009 | 0.1239 | 0.1222 |
| 150 | 0.1231 | 0.1277 | 0.1338 | 0.1246 |

TKN in g nitrogen/100 g liquid sample.

TABLE 31

Percentage conversion of the total TKN to soluble TKN for Experiment 1 (soybean hay)

| Time (min) | B | E | J | K | Average |
|---|---|---|---|---|---|
| 0 | 44.6 | 40.9 | 44.1 | 45.8 | 43.8 |
| 5 | 42.4 | 46.2 | 46.2 | 48.3 | 45.8 |
| 15 | 50.5 | 48.3 | 53.2 | 55.0 | 51.8 |
| 30 | 55.3 | 51.8 | 56.7 | 59.5 | 55.8 |
| 45 | 58.9 | 53.9 | 59.8 | 66.4 | 59.8 |
| 60 | 55.6 | 55.7 | 68.4 | 67.4 | 61.8 |
| 150 | 67.9 | 70.5 | 73.8 | 68.7 | 70.2 |

Figure 21:
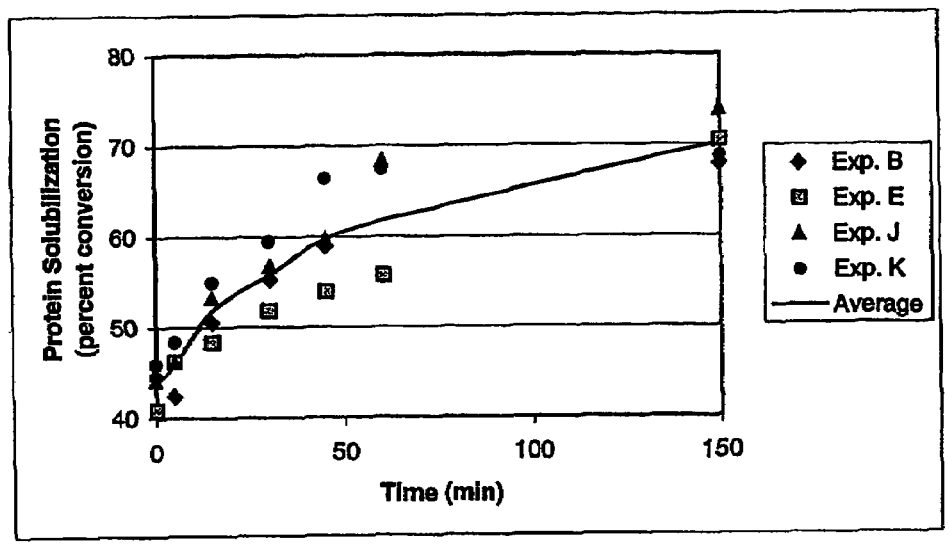
FIG. 21 is a graph illustrating an examination of the repeatability of results for protein solubilization of soybean hay using lime.

FIG. 21 presents the protein hydrolysis of soybean hay as a function of time for four different runs at the same experimental conditions. There is relatively small variability from one case to the other; the variance tends to increase at medium values and it is smaller at the extremes. From the time behavior, the values at 150 min are near the maximum conversion because the rate of change is relatively small for all the cases.

Experiment 2.

Temperature Effect

To determine the effect of temperature on solubilizing protein in soybean hay, experiments were run at different temperatures keeping the lime loading and soybean hay concentration constant (0.05 g lime/g soybean hay and 60 g dry soybean hay/L, respectively). The experimental conditions studied and variables measured are summarized in Table 32.

TABLE 32

Experimental conditions and variables measured to determine the effect of temperature in protein solubilization of soybean hay

| | Temperature (° C.) | | |
|---|---|---|---|
| | 75 | 100 | 115 |
| Mass of soybean hay (g) | 55.9 | 55.9 | 55.9 |
| Volume of water (mL) | 850 | 850 | 850 |
| Mass of lime (g) | 2.8 | 2.8 | 2.8 |

TABLE 32-continued

Experimental conditions and variables measured to determine
the effect of temperature in protein solubilization of soybean hay

| | Temperature (° C.) | | |
|---|---|---|---|
| | 75 | 100 | 115 |
| Initial temperature (° C.) | 75.3 | 93 | 100.2 |
| PH final | 9.5 | 8.6 | 8 |
| Residual solid (g) | 36.2 | 35.3 | 34.6 |
| Dissolved solids in 100 mL (g) | 2.7593 | 2.5706 | 2.6568 |
| Protein in 100 mL (g) | 0.647 | 0.770 | 0.823 |

Table 33 shows the total nitrogen content in the centrifuged liquid samples as a function of time for the different temperatures. On the basis of the average TKN for dry soybean hay (3.02%), protein hydrolysis conversions were estimated (Table 34).

TABLE 33

Total Kjeldhal nitrogen content in the centrifuged liquid phase
as a function of time for Experiment 2 (soybean hay)

| | Temperature | | |
|---|---|---|---|
| Time (min) | 75° C. | 100° C.* | 115° C. |
| 0 | 0.0822 | 0.0795 | 0.0781 |
| 5 | 0.0869 | 0.0830 | 0.0856 |
| 15 | 0.0889 | 0.0938 | 0.093 |
| 30 | 0.0916 | 0.1012 | 0.1008 |
| 45 | 0.0969 | 0.1083 | 0.1094 |
| 60 | 0.0982 | 0.1120 | 0.1140 |
| 150 | 0.1035 | 0.1273 | 0.1315 |

*Average of the four experimental runs.
TKN in g nitrogen/100 g liquid sample.

TABLE 34

Percentage conversion of the total TKN to soluble
TKN for Experiment 2 (soybean hay)

| | Temperature | | |
|---|---|---|---|
| Time (min) | 75° C. | 100° C.* | 115° C. |
| 0 | 45.4 | 43.8 | 43.1 |
| 5 | 47.9 | 45.8 | 47.2 |
| 15 | 49.0 | 51.8 | 51.3 |
| 30 | 50.5 | 55.8 | 55.6 |
| 45 | 53.5 | 59.8 | 60.4 |
| 60 | 54.2 | 61.8 | 62.9 |
| 150 | 57.1 | 70.2 | 72.6 |

*Average of the four experimental runs.

FIG. 22 presents the protein hydrolysis (percent conversion) as a function of time for the different temperatures studied. The conversion increases at higher temperatures. The conversion for 100° C. is similar to the one obtained at 115° C.; therefore, the lower temperature is favored because the amino acids should degrade less, the energy required is less, and the working pressure is lower.

An analysis of Table 32 shows again that pH decreased as protein solubilization increased because more lime reacts with amino acid products, and because the protein percentage of the product increases as conversion increases.

The conversions at 75° C. are statistically different from the ones at 100 and 115° C. In all the cases, the reaction rates tend to decrease at 150 min.

Experiment 3.

Lime Loading Effect

To determine the effect of lime loading on protein solubilization of soybean hay, experiments were run at different lime/soybean hay ratios keeping the temperature and soybean hay concentration constant (100° C. and 60 g dry soybean hay/L, respectively). The experimental conditions studied and variables measured are summarized in Table 35.

TABLE 35

Experimental conditions and variables measured to determine the lime
loading effect in protein solubilization of soybean hay

| | Lime loading (g lime/g soybean hay) | | |
|---|---|---|---|
| | 0 | 0.05 | 0.1 |
| Mass of soybean hay (g) | 55.9 | 55.9 | 55.9 |
| Volume of water (mL) | 850 | 850 | 850 |
| Mass of lime (g) | 0 | 2.8 | 5.6 |
| Temperature (° C.) | 100 | 100 | 100 |
| Initial Temperature (° C.) | 93.5 | 98.1 | 90.5 |
| pH final | 5.9 | 8.9 | 10.8 |
| Residual solid (g) | 36.1 | 35.4 | 34.4 |
| Dissolved solids in 100 mL (g) | 2.1803 | 2.7116 | 3.4937 |
| Protein in 100 mL (g) | 0.560 | 0.779 | 0.906 |

Table 36 shows the total nitrogen content in the centrifuged liquid samples as a function of time for different lime loadings. On the basis of the average TKN for dry soybean hay (3.02%), the protein hydrolysis conversions were estimated and are given in Table 37. The initial conversions are similar for all lime loadings because of the soluble components present in the soybean hay.

TABLE 36

Total Kjeldhal nitrogen content in the centrifuged liquid phase
as a function of time for Experiment 3 (soybean hay)

| | Lime loading | | |
|---|---|---|---|
| Time (min) | 0 (g/g) | 0.05 (g/g)* | 0.1 (g/g) |
| 0 | 0.0787 | 0.0795 | 0.0761 |
| 5 | 0.0850 | 0.0830 | 0.0811 |
| 15 | 0.0908 | 0.0938 | 0.1147 |
| 30 | 0.0895 | 0.1012 | 0.0965 |
| 45 | 0.0914 | 0.1083 | 0.1128 |
| 60 | 0.0888 | 0.1120 | 0.1178 |
| 150 | 0.0895 | 0.1273 | 0.1448 |

*Average of the four experimental runs.
TKN in g nitrogen/100 g liquid sample.

TABLE 37

Percentage conversion of the total TKN to soluble
TKN for Experiment 3 (soybean hay)

| | Lime loading | | |
|---|---|---|---|
| Time (min) | 0 (g/g) | 0.05 (g/g)* | 0.1 (g/g) |
| 0 | 43.4 | 43.8 | 42.0 |
| 5 | 46.9 | 45.8 | 44.7 |
| 15 | 50.1 | 51.8 | 63.3 |

TABLE 37-continued

Percentage conversion of the total TKN to soluble
TKN for Experiment 3 (soybean hay)

| Time (min) | Lime loading | | |
|---|---|---|---|
| | 0 (g/g) | 0.05 (g/g)* | 0.1 (g/g) |
| 30 | 49.4 | 55.8 | 53.2 |
| 45 | 50.4 | 59.8 | 62.2 |
| 60 | 49.0 | 61.8 | 65.0 |
| 150 | 49.4 | 70.2 | 79.9 |

*Average of the four experimental runs.

Figure 23:
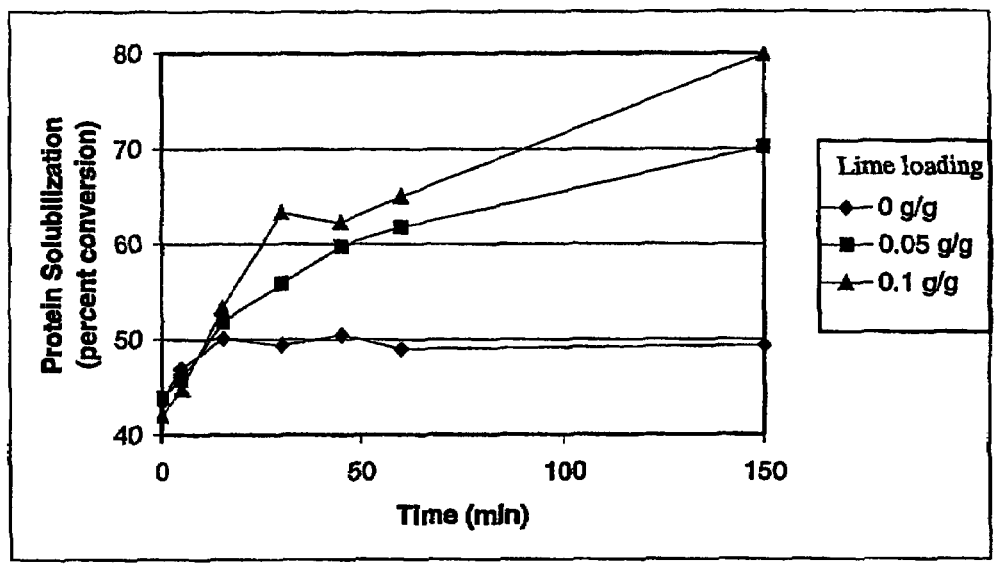
FIG. 23 is a graph illustrating lime loading effect of protein solubilization of soybean hay.

FIG. 23 presents the protein solubilized (percentage conversion) as a function of time for the different lime loadings studied. The conversion increases as the lime loading increases, giving the maximum effect when changing from the no-lime experiment to the 0.05 g/g lime loading. "Equilibrium" is achieved in the no-lime case at 15 min and further treatment at 100° C. generates no additional protein solubilization. Hence, a minimum lime loading is required for efficient protein solubilization in soybean hay. The difference between 0.05 and 0.1 g/g of lime loading is statistically significant only for 150 min.

In the no-lime experiment, the final pH was 5.9. Likely, the pH went acidic because of acids (e.g., acetyl groups) released from the biomass and amino acids released from the proteins. Because no lime was used, the concentration of dissolved solids was lower. In all the other cases reported in Table 35, lime was a portion of the dissolved solids.

Experiment 4.

Soybean Hay Concentration Effect

To determine the effect of the initial soybean hay concentration on protein solubilization, experiments were run at different soybean hay concentrations keeping the temperature and lime loading constant (100° C. and 0.05 g lime/g soybean hay, respectively). The experimental conditions studied and variables measured are summarized in Table 38.

TABLE 38

Experimental conditions and variables measured for determining
the effect of initial soybean hay concentration in protein solubilization

| | Soybean hay concentration (g dry soybean hay/L) | | |
|---|---|---|---|
| | 40 | 60 | 80 |
| Mass of soybean hay (g) | 37.8 | 53.4 | 75.6 |
| Volume of water (mL) | 850 | 800 | 850 |
| Mass of lime (g) | 2.9 | 4.0 | 5.7 |
| Temperature (° C.) | 75 | 75 | 75 |
| Initial temperature (° C.) | 78.2 | 73.2 | 82.1 |
| pH final | 10.7 | 11.3 | 11 |
| Residual solid (g) | 22.8 | 34.9 | 53.3 |
| Dissolved solids in 100 mL (g) | 2.0201 | 3.549 | 4.1349 |
| Protein in 100 mL (g) | 0.231 | 0.390 | 0.450 |

Table 39 shows the total nitrogen content in the centrifuged liquid samples as a function of time for the different soybean hay concentrations. On the basis of the average TKN for dry soybean hay (3.02%), the protein hydrolysis conversions were estimated and are given in Table 40.

TABLE 39

Total Kjeldhal nitrogen content in the centrifuged liquid phase
as a function of time for Experiment 4 (soybean hay)

| | Soybean hay concentration | | |
|---|---|---|---|
| Time (min) | 40 g/L | 60 g/L | 80 g/L |
| 0 | 0.0531 | 0.0741 | 0.1065 |
| 5 | 0.0503 | 0.0837 | 0.1215 |
| 15 | 0.0592 | 0.0876 | 0.1264 |
| 30 | 0.0639 | 0.0939 | 0.1399 |
| 45 | 0.0681 | 0.0977 | 0.1514 |
| 60 | 0.0701 | 0.1009 | 0.1472 |
| 150 | 0.1028 | 0.1277 | 0.1221 |

TKN in g nitrogen/100 g liquid sample.

TABLE 40

Percentage conversion of the total TKN to soluble
TKN for Experiment 4 (soybean hay)

| | Soybean hay concentration | | |
|---|---|---|---|
| Time (min) | 40 g/L | 60 g/L | 80 g/L |
| 0 | 44.0 | 43.8 | 44.1 |
| 5 | 41.7 | 45.8 | 50.3 |
| 15 | 49.1 | 51.8 | 52.3 |
| 30 | 53.0 | 55.8 | 57.9 |
| 45 | 56.5 | 59.8 | 62.7 |
| 60 | 58.1 | 61.8 | 60.9 |
| 150 | 85.2 | 70.2 | 50.5 |

Figure 24:
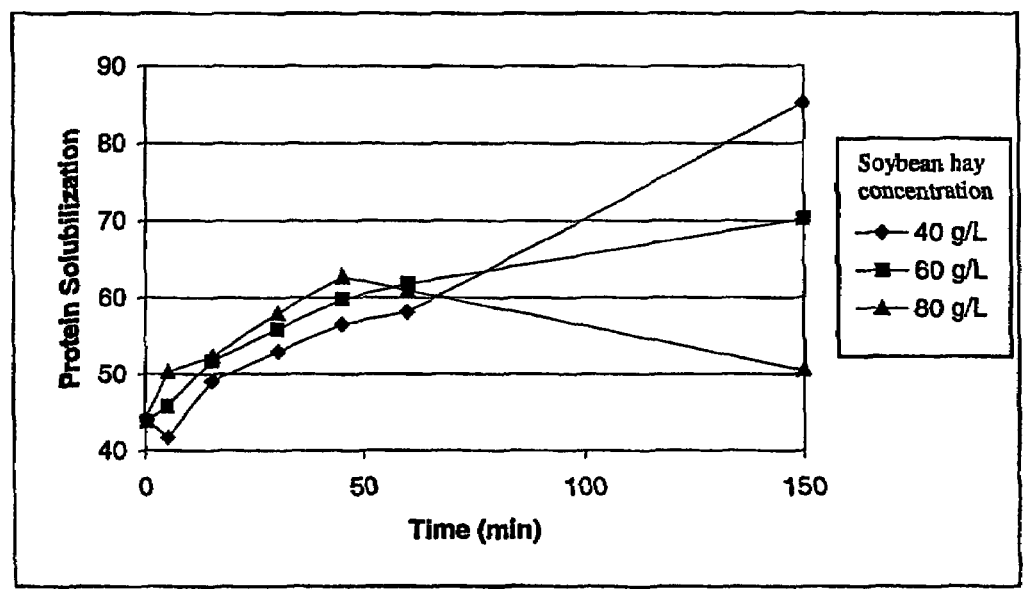
FIG. 24 is a graph illustrating the effect of soybean-hay concentration on protein solubilization.

FIG. 24 presents the protein solubilization (percentage conversion) as a function of time for the different soybean hay concentrations studied. It shows that protein solubilization does not vary with soybean hay concentration for times smaller than 60 min. The values at 150 min probably have some sampling problems because the results are not comparable with previous values. From Table 38, the dissolved solids and the protein present in the final product increase as the concentration of soybean hay increases.

A comparison between the compositions of the raw material and the residual solid gives information on the effectiveness of lime-treating soybean hay for protein solubilization. The composition for both materials is shown in Table 41. These results were obtained for 100° C., 0.05 g lime/g soybean hay and 60 g soybean hay/L.

TABLE 41

Comparison of protein and minerals content present in the raw soybean hay with the residual solid and the centrifuged liquid after lime treatment

| Sample | TKN (%) | P (%) | K (%) | Ca (%) | Mg (%) | Na (ppm) | Zn (ppm) | Fe (ppm) | Cu (ppm) | Mn (ppm) |
|---|---|---|---|---|---|---|---|---|---|---|
| Raw Soy | 3.0183 | 0.37 | 2.24 | 1.6477 | 0.3606 | 1399 | 34 | 280 | 13 | 53 |
| Residual solid | 1.9824 | 0.33 | 0.78 | 3.1171 | 0.1845 | 1326 | 19 | 158 | 9 | 35 |
| Centrifuged liquid | 0.1176 | 0.0104 | 0.155 | 0.2114 | 0.0146 | 104 | 2 | 10 | 0 | 2 |

*For 150 min.

Table 41 shows that the calcium concentration of the residual solid is greater than in the raw soybean hay. This value increases due to the lime added for the treatment, which is not completely soluble in water. The values for other minerals decrease during the lime treatment due to the high solubility of these salts. The nitrogen present in the residual solid is 33% smaller than the value obtained for the raw material before lime treatment.

The centrifuged liquid has a very high concentration of calcium, due to lime, and this implies that the calcium concentration in the final product (after water evaporation of centrifuged liquid) will be higher than the nitrogen content. The ratio of protein to calcium in the final product is:

ratio=(0.1176×6.25)/0.2114=3.48 g protein/g Ca.

The fraction of soybean hay that was solubilized is calculated as follows:

soluble fraction=1−{26.2 g residual solids−[(15.6 g dissolved solids/572 mL liquid)*200 mL moisture]}/55.9 g initial soybean hay=0.450 g solubilized/g of soybean hay.

This calculation corrects for the dissolved solids contained in the 200 mL of liquid. The solids were not washed, so the retained liquid includes dissolved solids. This value (0.450 g solubilized/g soybean hay) is reported in Table 42.

TABLE 42

Variables measured for 100° C., 0.05 g lime/g soybean hay, and 60 g soybean hay/L

| | | | |
|---|---|---|---|
| Mass of soybean hay (g) | 55.9 | pH final | 9.7 |
| Volume of water (mL) | 850 | Residual solid (g) | 36.2 |
| Mass of lime (g) | 2.8 | Dissolved solids in 572 mL (g) | 15.6 |
| Temperature (° C.) | 100 | Soluble fraction of soybean hay | 0.45 |

Experiment 5.

Amino Acid Analysis

Soybean hay was treated with lime at 150 mm and 24 h with the recommended conditions: 100° C., 0.05 g lime/g soybean hay, and 60 g soybean hay/L. The amino acid analysis was performed in three different ways:

1) Centrifuged liquid product-Free amino acid analysis. The analysis was made without extra HCL hydrolysis of the sample. No amino acids were destroyed by the analytical procedure, but soluble polypeptides might be missed in the analysis.
2) Centrifuged liquid product-Total amino acid analysis. The analysis was made with 24-h HCL hydrolysis of the sample. Some amino acids were destroyed by the analytical procedure or converted to other amino acids; soluble polypeptides are measured in the analysis.
3) Dry product after evaporating water from the centrifuged liquid. Because this sample was solid, HCL hydrolysis was required. Some amino acids (asparagine, glutamine, and tryptophan) were destroyed by the acid and could not be measured.

Table 43 and Table 44 show the free amino acids and the total amino acids concentration for lime treated soybean hay at 150 min and 24 h, respectively. Table 45 shows the protein and mineral content for both samples.

TABLE 43

Free and total amino acid concentration for the centrifuged liquid product of lime-hydrolyzed soybean hay at 150 min

| Amino acid | Non hydrolyzed-free amino acids | | Hydrolyzed-total amino acids | |
|---|---|---|---|---|
| | Concentration (mg/L) | Percentage (%) | Concentration (mg/L) | Percentage (%) |
| ASN | 213.48 | 30.64 | 0.00 | 0.00 |
| GLN | 0.00 | 0.00 | 0.00 | 0.00 |
| ASP | 69.49 | 9.97 | 447.76 | 33.01 |
| GLU | 46.46 | 6.67 | 172.72 | 12.73 |
| SER | 9.12 | 1.31 | 52.72 | 3.89 |
| HIS | 14.51 | 2.08 | 35.29 | 2.60 |
| GLY | 61.58 | 8.84 | 106.68 | 7.87 |
| THR | 6.36 | 0.91 | 37.01 | 2.73 |
| ALA | 20.63 | 2.96 | 58.07 | 4.28 |
| ARG | 97.44 | 13.98 | 142.70 | 10.52 |
| TYR | 0.00 | 0.00 | 16.78 | 1.24 |
| CYS | 36.45 | 5.23 | 0.00 | 0.00 |
| VAL | 20.71 | 2.97 | 48.20 | 3.55 |
| MET | 0.00 | 0.00 | 0.00 | 0.00 |
| PHE | 25.63 | 3.68 | 55.38 | 4.08 |
| ILE | 10.35 | 1.48 | 34.89 | 2.57 |
| LEU | 13.21 | 1.90 | 54.62 | 4.03 |
| LYS | 0.00 | 0.00 | 37.77 | 2.78 |
| TRP | 25.86 | 3.71 | 0.00 | 0.00 |
| PRO | 25.58 | 3.67 | 55.72 | 4.11 |
| Total | 696.85 | 100 | 1356.33 | 100 |

TABLE 44

Free and total amino acid concentration for the centrifuged liquid product of lime-hydrolyzed soybean hay at 24 h

| Amino acid | Non hydrolyzed-free amino acids | | Hydrolyzed-total amino acids | |
|---|---|---|---|---|
| | Concentration (mg/L) | Percentage (%) | Concentration (mg/L) | Percentage (%) |
| ASN | 98.37 | 17.04 | 0.00 | 0.00 |
| GLN | 0.00 | 0.00 | 0.00 | 0.00 |

TABLE 44-continued

Free and total amino acid concentration for the centrifuged
liquid product of lime-hydrolyzed soybean hay at 24 h

| Amino acid | Non hydrolyzed-free amino acids | | Hydrolyzed-total amino acids | |
|---|---|---|---|---|
| | Concentration (mg/L) | Percentage (%) | Concentration (mg/L) | Percentage (%) |
| ASP | 82.54 | 14.30 | 336.84 | 25.65 |
| GLU | 45.62 | 7.90 | 196.13 | 14.93 |
| SER | 6.44 | 1.12 | 52.93 | 4.03 |
| HIS | 0.00 | 0.00 | 25.71 | 1.96 |
| GLY | 97.90 | 16.96 | 150.13 | 11.43 |
| THR | 0.00 | 0.00 | 33.85 | 2.58 |
| ALA | 26.50 | 4.59 | 69.22 | 5.27 |
| ARG | 81.84 | 14.18 | 122.09 | 9.30 |
| TYR | 0.00 | 0.00 | 20.91 | 1.59 |
| CYS | 34.26 | 5.94 | 0.00 | 0.00 |
| VAL | 19.19 | 3.33 | 50.05 | 3.81 |
| MET | 0.00 | 0.00 | 0.00 | 0.00 |
| PHE | 21.72 | 3.76 | 54.20 | 4.13 |
| ILE | 10.79 | 1.87 | 37.79 | 2.88 |
| LEU | 7.83 | 1.36 | 60.64 | 4.62 |
| LYS | 0.00 | 0.00 | 35.50 | 2.70 |
| TRP | 23.27 | 4.03 | 0.00 | 0.00 |
| PRO | 20.88 | 3.62 | 67.49 | 5.14 |
| Total | 577.16 | 100 | 1313.48 | 100 |

TABLE 45

Comparison of protein and minerals content present in the centrifuged liquid of lime-treatment of soybean hay

| Sample | TKN (%) | P (%) | K (%) | Ca (%) | Mg (%) | Na (ppm) | Zn (ppm) | Fe (ppm) | Cu (ppm) | Mn (ppm) |
|---|---|---|---|---|---|---|---|---|---|---|
| 150 min | 0.1176 | 0.0104 | 0.155 | 0.2114 | 0.0146 | 104 | 2 | 10 | 0 | 2 |
| 24 h | 0.1562 | 0.0146 | 0.149 | 0.2716 | 0.0186 | 104 | 2 | 16 | 0 | 2 |

For both cases, the total amino acid concentration is approximately twice the free amino acid concentration. This shows that 50% of the amino acids are present in the form of small peptides.

For all the experiments, the centrifuged liquid contained a very high concentration of suspended particulate matter that might be measured in the Kjeldhal determination but not in the amino acid analysis. This explains the difference between the amino acid determination and the estimated protein concentration from Kjeldhal analysis (1.36 vs. 7.35 and 1.31 vs. 9.76 g protein/L).

A comparison of Tables 43-35 show that although the nitrogen concentration increases from 150 min to 24 h, the total amino concentration remains relatively constant, so, there is no need for a long treatment in the hydrolysis of soybean hay.

Finally, the amino acid composition of the protein product is compared to the essential amino acid needs of various domestic animals.

Table 46 shows that the amino acid product from the hydrolysis of soybean hay is not well balanced with respect to the requirements of different monogastric domestic animals. There are especially low values for histidine, threonine, methionine, and lysine; some other amino acids (tyrosine, valine) are sufficient for the majority of the animals, but not all. The lime hydrolysis of soybean hay generates a product that is very rich in asparagine, which is not essential in the diet of domestic animals. The protein product is best suited for ruminants.

TABLE 46

Amino acid analysis of product and essential amino acids requirements for various domestic animals (soybean hay)

| Amino Acid | Catfish | Dogs | Cats | Chickens | Pigs | Dry Product | Liquid (FAA) | Raw material |
|---|---|---|---|---|---|---|---|---|
| ASN | | | | | | | 30.64 | |
| GLN | | | | | | | 0.00 | |
| ASP | | | | | | 6.68 | 9.97 | 16.79 |
| GLU | | | | | | 9.56 | 6.67 | 15.10 |
| SER | | | | | | 7.11 | 1.31 | 7.84 |
| HIS | 1.31 | 1.00 | 1.03 | 1.40 | 1.25 | 0.00 | 2.08 | 2.55 |
| GLY | | | | | | 10.69 | 8.84 | 4.46 |
| THR | 1.75 | 2.64 | 2.43 | 3.50 | 2.50 | 1.80 | 0.91 | 4.23 |
| ALA | | | | | | 5.05 | 2.96 | 4.82 |
| ARG | 3.75 | 2.82 | 4.17 | 5.50 | 0.00 | 6.19 | 13.98 | 7.75 |
| VAL | 2.63 | 2.18 | 2.07 | 4.15 | 2.67 | 7.08 | 2.97 | 4.85 |
| CYS | 2.00* | 2.41* | 3.67* | 4.00* | 1.92* | 9.22 | 5.23 | ND |
| MET | 2.00* | 2.41* | 2.07 | 2.25 | 1.92* | 0.87 | 0.00 | 0.88 |
| TYR | 4.38+ | 4.05+ | 2.93+ | 5.85+ | 3.75+ | 2.71 | 0.00 | 2.82 |
| PHE | 4.38+ | 4.05+ | 1.40 | 3.15 | 3.75+ | 5.26 | 3.68 | 5.90 |
| ILE | 2.28 | 2.05 | 1.73 | 3.65 | 2.50 | 5.15 | 1.48 | 4.27 |
| LEU | 3.06 | 3.27 | 4.17 | 5.25 | 2.50 | 9.81 | 1.90 | 9.32 |

TABLE 46-continued

Amino acid analysis of product and essential amino acids requirements for various domestic animals (soybean hay)

| Amino Acid | Catfish | Dogs | Cats | Chickens | Pigs | Dry Product | Liquid (FAA) | Raw material |
|---|---|---|---|---|---|---|---|---|
| LYS | 4.47 | 3.50 | 4.00 | 5.75 | 3.58 | 1.10 | 0.00 | 5.93 |
| TRP | 0.44 | 0.91 | 0.83 | 1.05 | 0.75 | ND | 3.71 | ND |
| PRO |  |  |  |  |  | 11.70 | 3.67 | 5.21 |

*Cysteine + Methionine
+Tyrosine + Phenylalanine
FAA Free Amino Acids
All values are in g amino acid/100 g protein.

Differences between the two liquid samples (free vs. total amino acids—Table 43 and Table 45) can be explained by acid degradation of some amino acids (especially tryptophan, asparagine, and glutamine) in the total amino acid determination. Also, some protein in the centrifuged liquid may not have been hydrolyzed by the lime and may have been present as soluble polypeptides that were not detected by the HPLC analysis. The difference between the total amino acid in the liquid sample and the dry product is explained by the high concentration of suspended matter present in the liquid sample (centrifugation at 3500 rpm for 5 min). This suspended matter was not determined during the total amino acid measurement because the first step before HCL hydrolysis is centrifugation at 15000 rpm. The suspended matter forms an important part of the dry product and this explains the very different result for the amino acid composition.

The highest protein solubilization (85%) was achieved using 0.05 g Ca(OH)$_2$/g soybean hay, 150 minutes, 100° C., and 40 g dry soybean hay/L. The effect of the variables studied in this experiments can be summarized as:

Protein solubilization increases with temperature, with 100° C. giving the same results as 115° C. The recommended temperature is 100° C. because the energy requirements are smaller and no pressure vessel is required. The initial concentration of soybean hay has no important effect in the protein solubilization at times less than 60 min. A minimum lime loading (at least 0.05 g Ca(OH)$_2$/g soybean hay) is required to efficiently solubilize protein. For all cases, protein solubilization increases with time and the maximum values obtained are for 150 min. Soybean hay concentration has the least significant effect of the four variables studied.

A comparison of the amino acid analysis for the hydrolysis product and the essential amino acids requirements for various monogastric domestic animals shows it is not a well-balanced product. It has a high concentration of asparagine, a nonessential amino acid.

As in the alfalfa hay case, the protein product is most suited for ruminants. The lime treatment increases the digestibility of the holocellulose fraction (Chang et al., 1998), providing an added value to the residual solid from the thermo-chemical treatment. The used of both products as a ruminant feed ensures a more efficient digestion when compared to the initial material.

Example 4

Protein Solubilization in Chicken Offal

Chicken offal was obtained from the Texas A&M Poultry Science Department. Although in general, offal may contain bones, heads, beaks, and feet, in this case, it had only internal organs (e.g., heart, lungs, intestine, liver). The offal was blended for 10 min in an industrial blender, collected in plastic bottles, and finally frozen at −4° C. for later use. Samples of this blended material were used to obtain the moisture content, the total nitrogen (estimate of the protein fraction), the ash (mineral fraction), and the amino acid content to characterize the starting material.

Equation 1 defines the conversion of the centrifuged sample based on the initial total Kjeldhal nitrogen (TKN) of offal:

$$Conv_1 = \frac{V_{water} \times TKN_{centrifuged\ liquid}}{m_{dry\ offal} \times TKN_{dry\ offal}}. \quad (1)$$

Equation 2 defines the conversion of the non-centrifuged sample based on the initial total Kjeldhal nitrogen (TKN) of offal:

$$Conv_2 = \frac{V_{water} \times TKN_{non-centrifuged\ liquid}}{m_{dry\ offal} \times TKN_{dry\ offal}}. \quad (2)$$

Equation 3 estimates the fractional loss TKN of the initial offal nitrogen, using a mass balance:

$$L_{TKN} = 1 - \frac{V_{water} \times TKN_{non-centrifuged\ liquid}}{m_{dry\ offal} \times TKN_{dry\ offal}}. \quad (3)$$

The raw offal was 33.3% dry material and 66.7% moisture (see Table 47). The crude protein concentration of the dry offal was about 45% and the ash content was about 1%; the remaining 54% was fiber and fat.

TABLE 47

Water content of the raw offal

| Crucible | Offal (g) | Dry matter (g) | % Dry Weight |
|---|---|---|---|
| J | 32.2197 | 10.6402 | 33.024 |
| A | 30.8807 | 10.4548 | 33.855 |
| 4 | 28.6961 | 9.512 | 33.147 |
|  |  | Average | 33.342 |

Dry matter (oven at 105° C.).

Experiment 1.

Effect of Process Variables

Experiment 1 included eight runs labeled A through H. Runs A, B, and C were tested at 100° C., with 20 g dry offal/L and 0.1 g Ca(OH)$_2$/g dry offal. These conditions were obtained from the optimum results of a previous experiment that studied the same type of reaction for chicken feathers (Chang and Holtzapple, 1999). The remaining runs (D through H) were performed at different operating conditions, as shown in Table 48.

TABLE 48

Experimental conditions used in Experiment 1 (chicken offal)

| Run | Temperature (° C.) | Mass of Ca(OH)$_2$ (g) | Mass of wet Offal (g) | Volume of water (mL) | Ca(OH)$_2$ Loading (g/g dry offal) | Conc. of dry Offal (g/L) | Final pH |
|---|---|---|---|---|---|---|---|
| A | 100 | 1.70 | 51.5 | 850 | 0.099 | 20.20 | 9.50 |
| B | 100 | 1.70 | 51.2 | 850 | 0.100 | 20.08 | 9.65 |
| C | 100 | 1.70 | 51.5 | 850 | 0.099 | 20.20 | 9.50 |
| D | 100 | 3.40 | 102.3 | 850 | 0.100 | 40.13 | 9.55 |
| E | 100 | 5.10 | 153.3 | 850 | 0.100 | 60.13 | 9.50 |
| F | 100 | 2.55 | 102.5 | 850 | 0.075 | 40.21 | 8.90 |
| G | 100 | 1.70 | 102.4 | 850 | 0.050 | 40.17 | 9.10 |
| H | 75 | 3.40 | 102.4 | 850 | 0.100 | 40.17 | 10.10 |

Table 49 shows the total nitrogen content in the centrifuged liquid samples as a function of time for the eight runs. On the basis of the average TKN for dry offal (7.132%), the protein hydrolysis conversions were estimated and are given in Table 50. The conversions in Table 50 are presented graphically in FIGS. 25-28 V.4.

TABLE 49

Total Kjeldhal nitrogen content in centrifuged liquid phase as a function of time for Experiment 1 (chicken offal)

| | Experiment | | | | | | | |
|---|---|---|---|---|---|---|---|---|
| Time (min) | A | B | C | D | E | F | G | H |
| 5 | 0.0698 | 0.0520 | 0.0635 | 0.1332 | 0.2112 | 0.1438 | 0.0862 | 0.1191 |
| 10 | 0.0721 | 0.0543 | 0.0658 | 0.1354 | 0.2112 | 0.1461 | 0.0851 | 0.1191 |
| 15 | 0.0721 | 0.0543 | 0.0647 | 0.1366 | 0.2134 | 0.1473 | 0.0851 | 0.1213 |
| 25 | 0.0721 | 0.0554 | 0.0658 | 0.1388 | 0.2156 | 0.1495 | 0.0874 | 0.1179 |
| 35 | 0.0721 | 0.0566 | 0.0647 | 0.1388 | 0.2145 | 0.1517 | 0.0874 | 0.1191 |
| 45 | 0.0721 | 0.0554 | 0.0635 | 0.1388 | 0.2168 | 0.1495 | 0.0874 | 0.1179 |
| 60 | 0.0721 | 0.0600 | 0.0658 | 0.1399 | 0.2156 | — | — | — |
| 90 | 0.0721 | 0.0600 | 0.0669 | 0.1445 | 0.2156 | — | — | — |
| 120 | 0.0721 | 0.0589 | 0.0669 | 0.1433 | 0.2168 | 0.1507 | 0.0918 | 0.1202 |
| 180 | 0.0765 | 0.0623 | 0.0681 | 0.1433 | 0.2179 | — | — | — |

TKN in g nitrogen/100 g liquid sample.

TABLE 50

Fractional conversion of the total TKN to soluble TKN for Experiment 1 (chicken offal - Equation 1)

| | Experiment | | | | | | | |
|---|---|---|---|---|---|---|---|---|
| Time (min) | A | B | C | D | E | F | G | H |
| 5 | 0.467 | 0.350 | 0.425 | 0.466 | 0.511 | 0.502 | 0.301 | 0.416 |
| 10 | 0.482 | 0.365 | 0.440 | 0.473 | 0.511 | 0.510 | 0.297 | 0.416 |
| 15 | 0.482 | 0.365 | 0.433 | 0.478 | 0.516 | 0.514 | 0.297 | 0.424 |
| 25 | 0.482 | 0.373 | 0.440 | 0.485 | 0.522 | 0.522 | 0.305 | 0.412 |
| 35 | 0.482 | 0.381 | 0.433 | 0.485 | 0.519 | 0.529 | 0.305 | 0.416 |

TABLE 50-continued

Fractional conversion of the total TKN to soluble TKN
for Experiment 1 (chicken offal - Equation 1)

| Time (min) | Experiment | | | | | | | |
|---|---|---|---|---|---|---|---|---|
| | A | B | C | D | E | F | G | H |
| 45 | 0.482 | 0.373 | 0.425 | 0.485 | 0.525 | 0.522 | 0.305 | 0.412 |
| 60 | 0.482 | 0.404 | 0.440 | 0.489 | 0.522 | — | — | — |
| 90 | 0.482 | 0.404 | 0.447 | 0.505 | 0.522 | — | — | — |
| 120 | 0.482 | 0.396 | 0.447 | 0.501 | 0.525 | 0.526 | 0.321 | 0.420 |
| 180 | 0.512 | 0.419 | 0.456 | 0.501 | 0.527 | — | — | — |

FIG. 25-28 show that at these conditions, the conversion of nitrogen in the solid phase to the liquid phase was not efficient (between 45 and 55%). This implies that much of the protein of the solid phase does not react with the hydroxide or that the amino acids formed precipitate back to the solid phase. Another consideration is the presence of fats in the raw material that consume hydroxide and therefore slows the protein hydrolysis.

FIG. 25-28 show that the reaction occurs during the first 10 or 15 min of contact time and then the conversion (concentration) stays constant.

Figure 25:
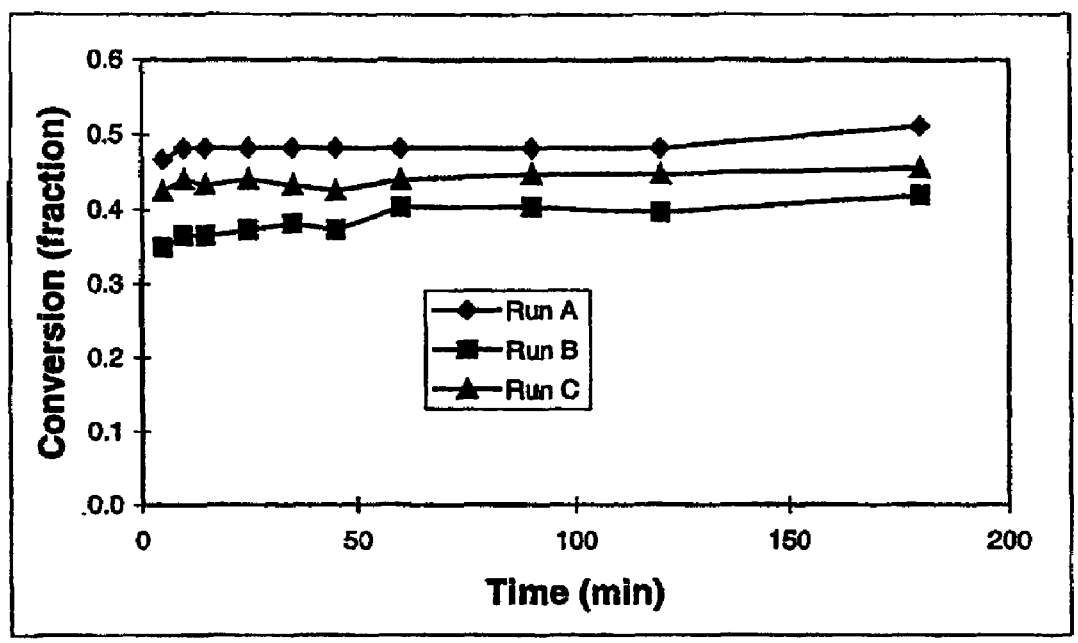
FIG. 25 is a graph illustrating the reproducibility of off offal studies. Three runs were performed at identical operating conditions.
Figure 26:
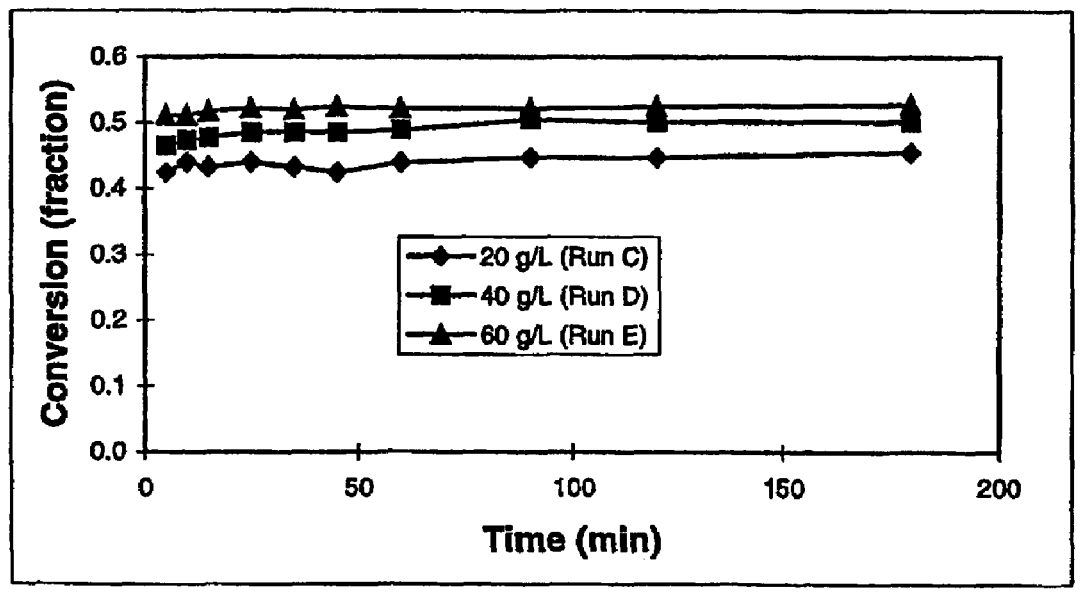
FIG. 26 is a graph illustrating a comparison of conversion at three different offal concentrations.

FIG. 25 shows that the results from different runs employing the same experimental conditions give comparable conversions. FIG. 26 shows that the conversions are similar for different initial concentrations of raw material. This means that the amino acid concentration in the liquid phase will be higher for a higher starting concentration of offal.

Figure 27:
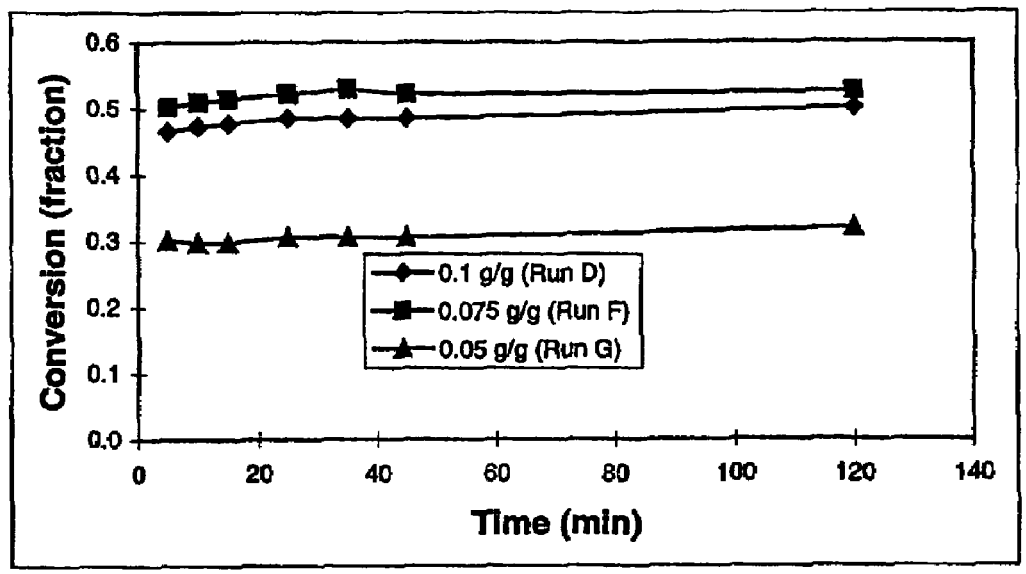
FIG. 27 is a graph illustrating a comparison of conversion for three different lime loadings.
Figure 28:
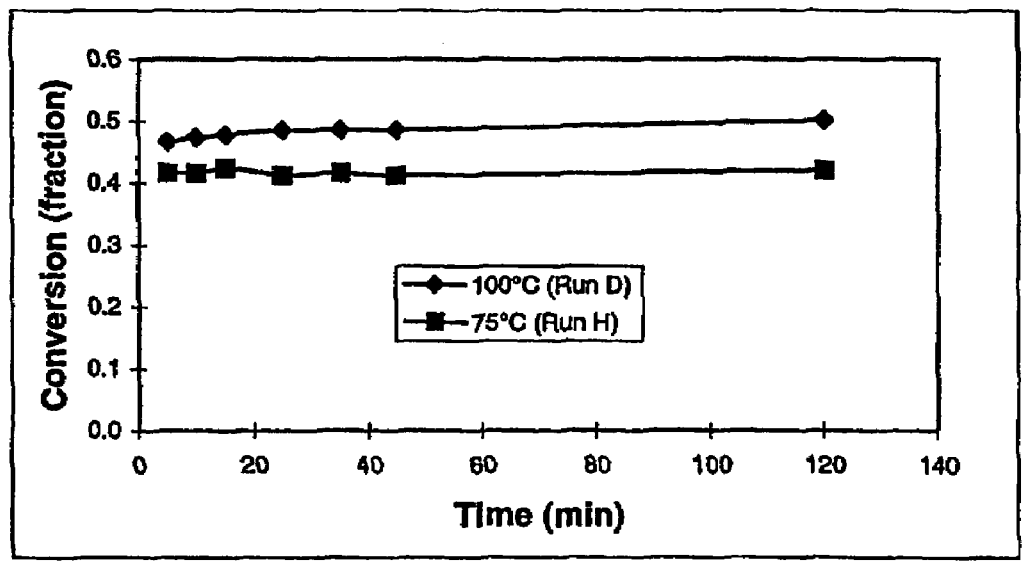
FIG. 28 is a graph illustrating a comparison of conversion for two different temperatures.

FIG. 27 shows that low lime loadings have low conversions; therefore, the reaction needs a minimum loading. Because similar results are obtained for 0.075 and 0.1 lime loading, the minimum 0.075 g Ca(OH)$_2$/g dry offal will be used. FIG. 28 shows that at 75° C., the reaction is almost as fast as it is at 100° C. The lower temperature is favored because the amino acids should degrade less.

Experiment 2.

Process Optimization

In Experiment 2, the objective was to find conditions in which the conversion is higher (more efficient). Experiment 2 included a total of eight runs labeled I through P. Because the reaction is fast and the conversion is constant after 15 min, only one sample is needed to obtain a representative condition of the reaction. Table 51 shows the experimental conditions and the TKN concentration in liquid samples.

TABLE 51

Experimental conditions and results for Experiment 2
(chicken offal - two samples for each run)

| Run | Temperature (° C.) | Conc. of Ca(OH)$_2$ (g/g dry offal) | Conc. of dry Offal (g/L) | Final pH | Time Sample | TKN | TKN |
|---|---|---|---|---|---|---|---|
| I | 50 | 0.100 | 40 | 8.35 | 1.5 h | 0.2067 | 0.2067 |
| J | 100 | 0.075 | 40 | 8.45 | 30 min | 0.169 | 0.2209(a) |
| K | 100 | 0.075 | 40 | 8.45 | 2 h | 0.1722 | 0.2296(a) |
| L | 75 | 0.075 | 40 | — | 30 min | 0.2046 | 0.234(a) |
| M | 75 | 0.075 | 40 | | 2 h | 0.2231 | 0.2318(a) |
| N | 100 | 0.400 | 40 | 12.05 | 1 h | 0.1116 | 0.1094 |
| O | 100 | 0.300 | 40 | 12.0 | 1-2 h | 0.1203 | 0.1289 |
| P | 75 | 0.300 | 40 | 12.0 | 1-2 h | 0.143 | 0.1463 |

(a)Non-centrifuged liquid sample.
TKN in g nitrogen/100 g liquid sample.

Table 52 shows that for Runs I through M, the conversion ranges from 63% to 84% using Equation 1 (i.e., liquid TKN per TKN added in solids). For runs J through M, the conversion ranges from 83% to 87% using Equation 2 (i.e., liquid TKN in non-centrifuged sample per TKN added in solids). Equation 3, for runs J to M, shows a loss of 13% of the initial offal nitrogen at 75° C. and a loss of 15% of the initial offal nitrogen at 100° C. It is unclear where the lost nitrogen goes. Perhaps it is lost into the gas phase, or perhaps it attaches to metal surfaces in the reactor. Table 51 and Table 52 show that for the runs with the highest conversions, the final pHs are lower than all those obtained for Experiment 1 and for the other runs in Experiment 2. From Experiment 2, one may recommend a temperature of 75° C., with a lime loading of 0.075 g Ca(OH)$_2$/g dry offal.

TABLE 52

Fractional conversion of the total TKN to soluble
TKN for Experiment 2 (chicken offal)

| Run | Conversion Sample 1 | Conversion Sample 2 | Fractional loss of TKN |
|---|---|---|---|
| I | 0.781(1) | 0.781(1) | |
| J | 0.634(1) | 0.829(2) | 0.171(3) |
| K | 0.646(1) | 0.861(2) | 0.139(3) |
| L | 0.768(1) | 0.879(2) | 0.121(3) |
| M | 0.838(1) | 0.870(2) | 0.130(3) |
| N | 0.436(1) | 0.411(1) | |
| O | 0.452(1) | 0.484(1) | |
| P | 0.536(1) | 0.548(1) | |

(1)Conversion calculated using Equation 1.
(2)Conversion calculated using Equation 2.
(3)Lost nitrogen calculated using Equation 3.

Experiment 3.

Analysis of Final Product

Figure 29:
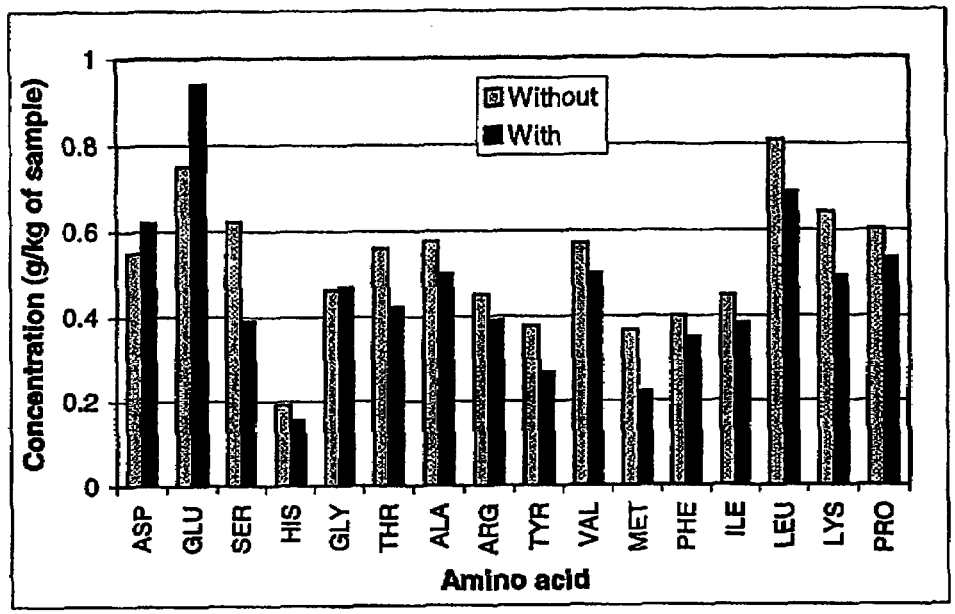
FIG. 29 is a graph illustrating amino acid content of liquid product without additional treatment, and with treatment by 6N HCl.

FIG. 29 shows the amino acid spectrum for two centrifuged liquid samples obtained under conditions of Experiment 2 (lime loading 0.075 g Ca(OH)$_2$/g dry offal, temperature 75° C., offal concentration 40 g dry offal/L, and time 1 h). First, the amino acid composition in the raw centrifuged liquid sample without further treatment was determined by HPLC analysis. Second, the centrifuged liquid sample was treated with 6-N HCL for 1 h, which hydrolyzed protein to its corresponding amino acids. By comparing both results, one may conclude that lime hydrolyzes the chicken offal into individual amino acids; the results of the two cases are essentially identical.

Figure 30:
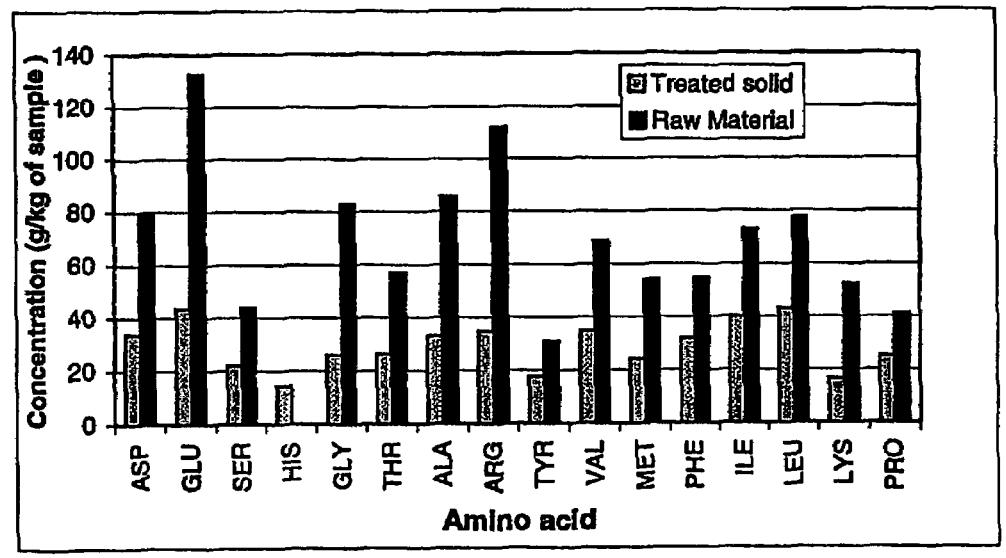
FIG. 30 is a graph illustrating a comparison of amino acids present in raw material and dry treated solids. Because the treated solid was very wet (80% moisture) when removed from the reactor, some of the amino acids shows are derived from residual liquid product.

FIG. 30 compares the amino acid spectrum for the raw offal and for the solid residue that remains after lime treatment. To do this, the residual solids were dried at 105° C. for 24 h, a sample was taken for protein measurement. Because the water content of this solid residue was about 80%, the measured protein came from both the liquid and solid phases. The amino acid content in the residual solids is much less than in the raw offal because amino acids have dissolved into the liquid phase.

Using mass balances and the data shown in Figure V.6, the amount of each amino acid "extracted" from the raw material ranges from 50% to 75%. However, this includes the protein in the liquid adhering to the solids. If one subtracts the protein dissolved in the adhered liquid, the extraction for each amino acid ranges from 52% to 76% of the crude protein, which is similar to the results obtained in Experiment 2.

Figure 31:
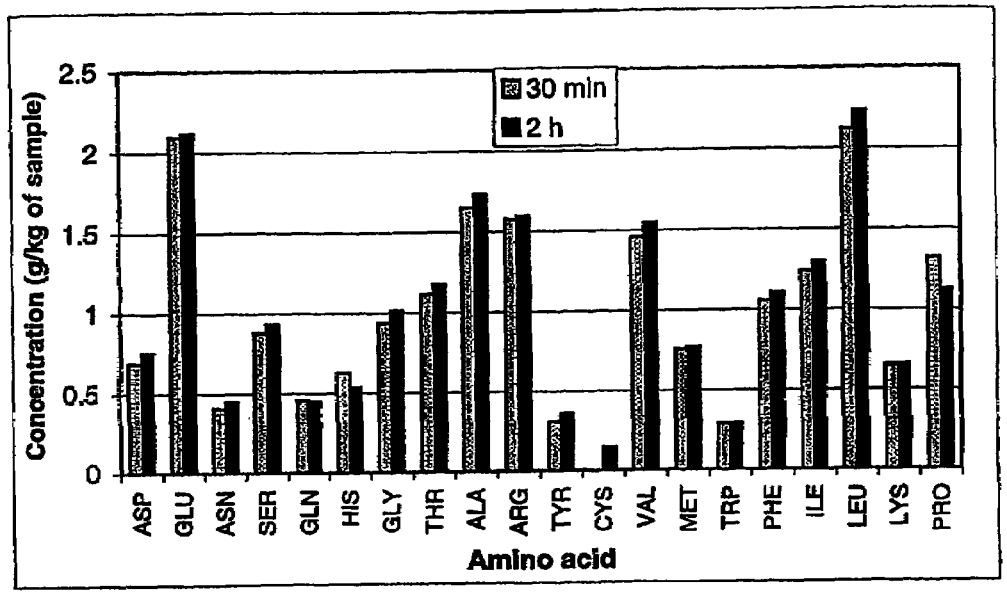
FIG. 31 is a graph illustrating a comparison of the amino acids present in the liquid phase after 30 minutes and after 2 hours in an experiment at 75° C., 0.075 g lime/g dry offal, and 60 g dry offal/L slurry.
Figure 32:
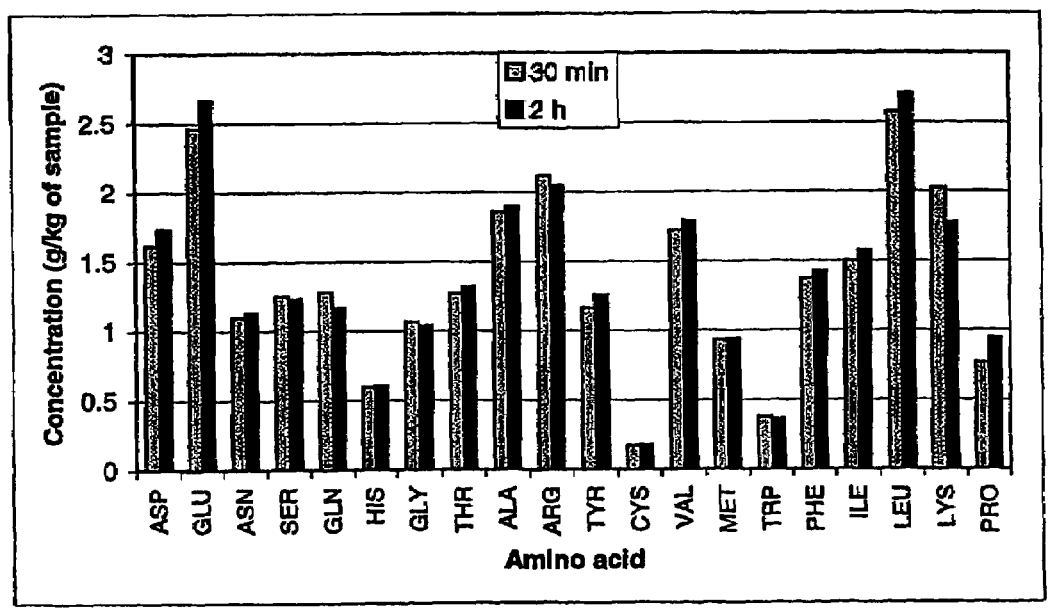
FIG. 32 is a graph illustrating a comparison of the amino acids present in the liquid phase after 30 minutes and after 2 hours in an experiment at 75° C., 0.075 g lime/g dry offal, and 80 g dry offal/L slurry.

Another important issue is to determine the degradation of individual amino acids at the reactor operating conditions. To determine this, one needs to obtain the amino acid concentration at two different times. FIG. 31 shows that the amino acids present in the centrifuged liquid phase at 30 min are nearly identical to those at 2 h; implying that the amino acids are stable at the operating conditions. FIG. 32 shows that with a different starting concentration of offal; again, the amino acids have the same concentration at 30 min and 2 h.

Figure 33:
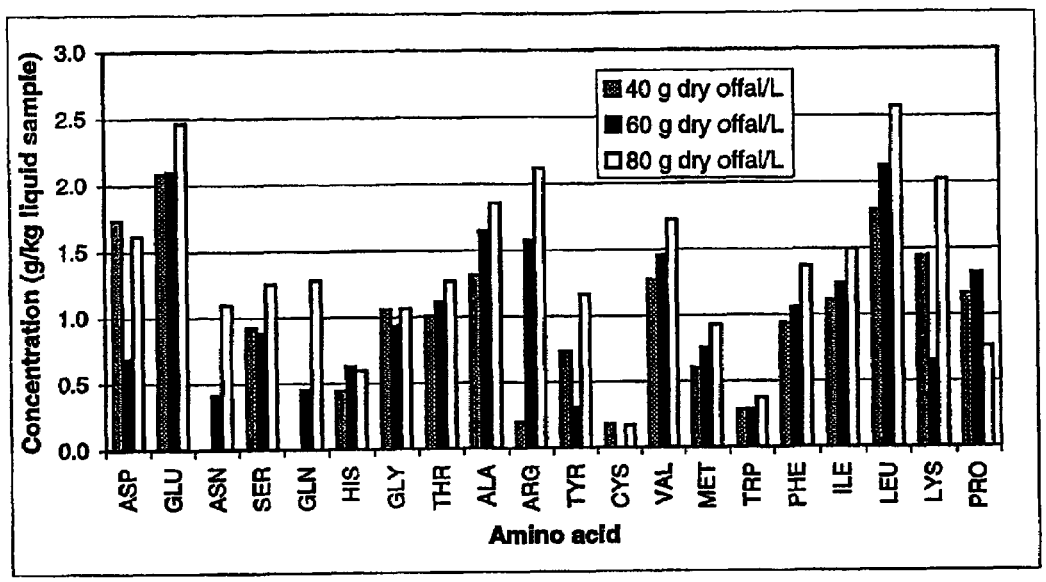
FIG. 33 is a graph illustrating a comparison of the amino acids in the centrifuged liquid phase after 30 minutes for three different initial offal concentrations (g dry offal/L slurry) at 75° C. and 0.075 g lime/g dry offal.

FIG. 33 compares the results of three different initial offal concentrations, for the same time, temperature, and lime loading. These results show that the amino acid concentration in the centrifuged liquid phase is higher for a higher initial concentration of raw material, as expected.

Figure 34:
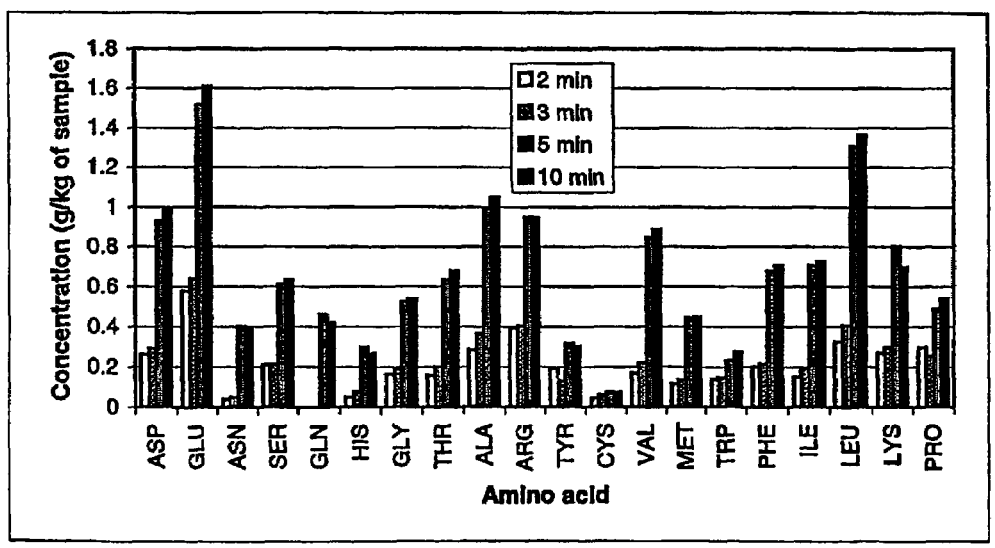
FIG. 34 is a graph illustrating a comparison of the amino acids present in the centrifuged liquid phase at different times as 75° C., 0.075 g lime/g dry offal, and 40 g dry offal/L slurry.

FIG. 34 examines the amino acid concentration as a function of time for the first 10 min of reaction. The concentration stabilizes for all amino acids after 10 min, and the 30-min values are also comparable. This implies that the reaction occurs during the first 10 to 30 min of contact, as concluded in Experiment 1.

From the experiments performed using HPLC and Kjeldhal methods, the nitrogen content was comparable in both the cases (see Table 53). These results imply that the main contribution to the total nitrogen content is from the amino acids (i.e., the protein content of the chicken offal).

TABLE 53

Comparison of results for nitrogen content
(g nitrogen/100 g liquid sample) with HPLC and
Kjeldhal methods for experiments in FIG. V.10

|  | 2 min | 3 min | 5 min | 10 min |
|---|---|---|---|---|
| HPLC | 0.065 | 0.072 | 0.211 | 0.216 |
| Kjeldhal | 0.11 | 0.11 | 0.18 | 0.17 |

Table 54 compares the various requirements for essential amino acids to the needs of various domestic animals, which are presented in Table 55. Table 56 indicates the compositions of various common animal fees and may also be compared to Table 54.

TABLE 54

Comparison of the amino acid present in the liquid phase of two
experiments: (a) at 75°, 0.075 g Ca(OH)$_2$/g dry offal,
60 g dry offal/L, and 30 min; and (b) at 50° C., 0.100 g
Ca(OH)$_2$/g dry offal, 40 g dry offal/L, and 90 min with the
dietary requirement of different animals

| Amino Acid | Catfish | Dogs | Cats | Chickens | Pigs | Solubilized Offal (a) | Solubilized Offal (b) |
|---|---|---|---|---|---|---|---|
| ASN |  |  |  |  |  | 2.14 | 0.82 |
| ASP |  |  |  |  |  | 3.62 | 6.36 |
| GLU |  |  |  |  |  | 10.56 | 8.70 |
| SER |  |  |  |  |  | 4.54 | 7.21 |
| HIS | 1.31 | 1.00 | 1.03 | 1.40 | 1.25 | 2.92 | 2.23 |
| GLY |  |  |  |  |  | 4.89 | 5.35 |
| THR | 1.75 | 2.64 | 2.43 | 3.50 | 2.50 | 5.74 | 6.47 |
| ALA |  |  |  |  |  | 8.47 | 6.66 |
| ARG | 3.75 | 2.82 | 4.17 | 5.50 | 0.00 | 7.95 | 5.22 |
| VAL | 2.63 | 2.18 | 2.07 | 4.15 | 2.67 | 7.53 | 6.60 |
| CYS | 2.00* | 2.41* | 3.67* | 4.00* | 1.92* | 0.7 | ND |
| MET | 2.00* | 2.41* | 2.07 | 2.25 | 1.92* | 3.83 | 4.23 |
| TYR | 4.38+ | 4.05+ | 2.93+ | 5.85+ | 3.75+ | 1.68 | 4.36 |
| PHE | 4.38+ | 4.05+ | 1.40 | 3.15 | 3.75+ | 5.42 | 4.65 |
| ILE | 2.28 | 2.05 | 1.73 | 3.65 | 2.50 | 6.36 | 5.19 |
| LEU | 3.06 | 3.27 | 4.17 | 5.25 | 2.50 | 10.91 | 9.37 |
| LYS | 4.47 | 3.50 | 4.00 | 5.75 | 3.58 | 3.27 | 7.42 |
| TRP | 0.44 | 0.91 | 0.83 | 1.05 | 0.75 | 2.26 | ND |
| PRO |  |  |  |  |  | 6.11 | 6.98 |

*Cysteine + Methionine
+Tyrosine + Phenylalanine
ND Not determined
Values expressed as g individual amino acid per 100 g total amino acids.

TABLE 55

Nutritional requirement for domestic animals during growth phase
(Pond et al., 1995)

|  | Catfish | Dogs | Cats | Chicken Broiler | Pigs |
|---|---|---|---|---|---|
| Crude protein (%) | 32.0 | 22.0 | 30.0 | 20.0 | 12.0 |
| Arginine (%) | 1.20 | 0.62 | 1.25 | 1.10 | 0.00 |
| Methionine (%) | 0.64* | 0.53* | 0.62 | 0.45 | 0.23* |
| Cysteine (%) | 0.64* | 0.53* | 1.10* | 0.80* | 0.23* |
| Histidine (%) | 0.42 | 0.22 | 0.31 | 0.28 | 0.15 |
| Isoleucine (%) | 0.73 | 0.45 | 0.52 | 0.73 | 0.30 |
| Leucine (%) | 0.98 | 0.72 | 1.25 | 1.05 | 0.30 |
| Lysine (%) | 1.43 | 0.77 | 1.20 | 1.15 | 0.43 |
| Tyrosine (%) | 1.40** | 0.89** | 0.88** | 1.17** | 0.45** |
| Phenylalanine (%) | 1.40** | 0.89** | 0.42 | 0.63 | 0.45** |
| Threonine (%) | 0.56 | 0.58 | 0.73 | 0.70 | 0.30 |
| Tryptophan (%) | 0.14 | 0.20 | 0.25 | 0.21 | 0.09 |
| Valine (%) | 0.84 | 0.48 | 0.62 | 0.83 | 0.32 |

Notes:
1) *Cysteine + Methionine
2) **Tyrosine + Phenylalanine
3) All values are expressed as percentage of the total diet (g/100 g feed).

TABLE 56

Composition of different feed used in the diet of domestic animals (Pond et al., 1995)

|  | Blood meal | Fish meal** | Soybean meal | Gluten meal | Corn meal | Milo | Meat and bone meal | Feather meal |
|---|---|---|---|---|---|---|---|---|
| Dry matter (%) | 91.0 | 92.0 | 89 | 91.0 | 93.0 | 89.0 | 94 | 91.0 |
| Crude fiber (%) | 1.0 | 0.9 | 6.0 | 4.0 | 12.0 | 2.0 | 2.4 | 4.7 |
| Crude protein (%) | 79.9 | 61.2 | 45.8 | 42.9 | 18.0 | 11.0 | 50.9 | 85.4 |
| Digestibility (%)* | 62.3 | 56.4 | 41.7 | 35.7 | 14.8 | 7.8 | 45.0 | 60.2 |
| Arginine (%) | 3.50 | 3.74 | 3.20 | 1.40 | 1.20 | 0.36 | 3.05 | 5.33 |
| Cysteine (%) | 1.40 | 0.58 | 0.67 | 0.60 | 0.32 | 0.18 | 0.46 | 3.21 |
| Glycine (%) | 3.40 | — | 2.10 | 1.50 | — | 0.40 | — | — |
| Histidine (%) | 4.20 | 1.44 | 1.10 | 1.00 | — | 0.27 | 0.96 | 0.47 |
| Isoleucine (%) | 1.00 | 2.85 | 2.50 | 2.30 | — | 0.53 | 1.47 | 3.51 |
| Leucine (%) | 10.30 | 4.48 | 3.40 | 7.60 | 1.70 | 1.42 | 3.02 | 0.42 |
| Lysine (%) | 6.90 | 4.74 | 2.90 | 0.80 | 0.90 | 0.27 | 2.89 | 1.67 |
| Methionine (%) | 0.90 | 1.75 | 0.60 | 1.00 | 0.35 | 0.09 | 0.08 | 0.54 |
| Phenylalanine (%) | 6.10 | 2.46 | 2.20 | 2.90 | 0.80 | 0.45 | 1.65 | 3.59 |
| Threonine (%) | 3.70 | 2.51 | 1.70 | 1.40 | 0.90 | 0.27 | 1.60 | 3.63 |
| Tryptophan (%) | 1.10 | 0.65 | 0.60 | 0.20 | 0.30 | 0.09 | 0.28 | 0.52 |
| Tyrosine (%) | 1.80 | 1.93 | 1.40 | 1.00 | 1.50 | 0.36 | 0.79 | 2.35 |
| Valine (%) | 6.50 | 3.19 | 2.40 | 2.20 | 1.30 | 0.53 | 2.14 | 5.85 |

Notes:
1) *As-fed basis for ruminants.
2) **There are three types of fish meal: anchovy, menhaden and herring. The values given are for menhaden.
3) The values of the amino acids are in percentage as-fed basis (g amino acid/100 g feed).

The tabulated results imply that the solubilized protein meets, or exceeds, the essential amino acids requirements of the animals during their growth phase for the run at 50° C. On the other hand, at 75° C. (optimum conversion conditions), the values for tyrosine and lysine are lower than the requirements.

Chicken offal, containing 15% protein (wet basis) or 45% protein (dry basis), can be used to obtain an amino acid-rich product by treating with $Ca(OH)_2$ at temperatures less than 100° C. A simple non-pressurizing vessel can be used for the above process due to the low temperature requirements.

For all conditions of temperature, lime loading, and offal concentration that were studied, no significant change in the conversion occurred after 30 minutes of reaction.

The optimal conditions to maximize the protein conversion (up to 80%) are 0.075 g $Ca(OH)_2$/g dry offal processed at 75° C. for at least 15 min. Initial offal concentration had no significant effect either on the conversion or the amino acid spectrum of the product.

However, a high offal concentration is recommended to obtain a highly concentrated product, thus reducing the energy requirements for concentrating the final product.

Little amino acid degradation was observed for all experiments performed below 100° C. and up to 2 hours. Thus, little degradation should occur by evaporating the liquid product at temperatures around 100° C.

At 50° C., the spectrum of essential amino acids obtained meets or exceeds the requirements for many domestic animals during their growth period. Thus, the amino acid-rich solid product obtained by lime treating chicken offal could serve as a protein supplement for these animals. The product obtained at 75° C. has a smaller amount of lysine and tyrosine than required and therefore will not be as efficient.

Example 5

Protein Solubilization in Chicken Offal and Feathers

Disposal of animal organs by the slaughter industry is an important environmental issue. The poultry industry generates a large amount of wastes (offal, feathers, and blood) centralized in the slaughterhouses in volumes that are large enough to develop techniques for processing these wastes. If the wastes are collected separately, they can be processed into blood meal (heat-dried blood used as a feed supplement), hydrolyzed feather meal, poultry meal, and fat.

Five percent of the body weight of poultry is feathers. Because of their high protein content (89.7% of dry weight, Table 57), feathers are a potential protein source for food, but complete destruction of the rigid keratin structure is necessary (Dalev, 1994).

TABLE 57

Composition of poultry offal and chicken feathers (Wisman et al., 1957, and Dalev, 1994)

| % total weight | Fresh offal | Dry matter | Feathers (dry matter) |
|---|---|---|---|
| Moisture | 69.5 | — | — |
| Crude protein | 17.2 | 56.5 | 89.7 |
| Ether extract (fat) | 8.0 | 26.2 | 1.4 |
| Crude fiber | 0.1 | 0.4 | ND |
| Ash | 3.7 | 12.1 | 6.3 |
| Nitrogen free extract | 1.5 | 4.8 | ND |
| Calcium (Ca) | 0.5 | 1.7 | 0.35 |
| Phosphorus (P) | 0.6 | 2.0 | 0.13 |
| Sodium (Na) | ND | — | 0.4 |
| Potassium (K) | ND | — | 0.9 |

Poultry offal contains much more histidine, isoleucine, lysine, and methionine than chicken feathers (characteristics of chicken offal and feathers are shown in Table 57s to 59.). Hence, poultry offal and feathers meal together would have a better balance of amino acids (E I Boushy and Van der Poel, 1994). A feathers/offal process may accommodate the fact that feathers are harder to decompose or hydrolyze than offal.

TABLE 58

Amount of viable microorganisms in poultry offal (Acker et al., 1959)

| | Unwashed | Washed | Agar used |
|---|---|---|---|
| Total aerobes | 280000 | 90000 | Trypticase soy |
| Total anaerobes | 98000 | 28000 | Linden thioglycollate |
| Spore forming anaerobes (*Clostridium botulinum*) | 4500 | 2000 | Linden thioglycollate |
| Coliforms (*Salmonella*) | 20000 | 9000 | Violet red bile |
| Lactobacilli | 270000 | 97000 | Tomato juice |
| Yeasts | 28000 | 26000 | Littman oxgall |
| Cottony molds | <100 | <100 | Littman oxgall |

Count/g wet weight.

TABLE 59

Composition of poultry offal (Acker et al., 1959)

| | Unwashed | Washed | Units |
|---|---|---|---|
| Crude protein | 20.5 | 17.7 | g/100 g wet matter |
| Digestible protein | 91.2 | 91.5 | g/100 g protein |
| Ether extract | 8.4 | 7.6 | g/100 g wet matter |
| Crude fiber | 1.1 | 1.0 | g/100 g wet matter |
| Moisture | 68.5 | 72.1 | g/100 g wet matter |
| Ash | 4.0 | 4.3 | g/100 g wet matter |
| Loss on ignition | 27.5 | 23.5 | g/100 g dry matter |
| Calcium | 1.4 | 1.8 | g/100 g wet matter |
| Phosphorus | 1.1 | 1.3 | g/100 g wet matter |
| Riboflavin | 3.8 | 3.1 | mg/100 g dry matter |
| Niacin | 4.8 | 6.3 | mg/100 g dry matter |
| Ca pantothenate | 2.3 | 1.1 | mg/100 g dry matter |
| Pyroxidine | 0.11 | 0.09 | mg/100 g dry matter |
| $B_{12}$ | 52.6 | 9.5 | µg/100 g dry matter |
| Vitamin A | 806.8 | 1163.9 | USP units/100 g dry matter |
| Carotene | 356.2 | 656.8 | Int'l units/100 g dry matter |
| Total Vit. A | 1163.0 | 1820.7 | Int'l units/100 g dry matter |
| Total Vit. C | 47.9 | 26.9 | mg/100 g dry matter |
| Vitamin E | 3.4 | 7.7 | Int'l units/100 g dry matter |
| Inositol | 218.1 | 131.5 | mg/100 g dry matter |
| Thiamine | 0.13 | 0.07 | mg/100 g dry matter |
| Folic acid | 0.11 | 0.04 | mg/100 g dry matter |
| Arginine | 6.6 | 7.1 | g/100 g protein |
| Histidine | 1.2 | 1.4 | g/100 g protein |
| Isoleucine | 10.5 | 11.0 | g/100 g protein |
| Leucine | 8.9 | 10.0 | g/100 g protein |
| Lysine | 13.3 | 13.6 | g/100 g protein |
| Methionine | 2.7 | 2.8 | g/100 g protein |
| Phenylalanine | 5.5 | 5.0 | g/100 g protein |
| Threonine | 2.5 | 3.2 | g/100 g protein |
| Tryptophan | 0.9 | 0.7 | g/100 g protein |
| Valine | 2.9 | 3.4 | g/100 g protein |

Because the addition of feces to an animal diet may adversely affect growth (Acker et al., 1959), and because of public health considerations, offal used for feeding purposes may be treated to reduce the bacterial load (Table 58). There are high levels of ash content (calcium and phosphorus) and vitamins present in offal (Table 59). It appears that poultry offal is a significant source of vitamins, minerals, and possibly unidentified growth factors (Acker et al., 1959).

One way to treat poultry by-products is by rendering, which includes five phases:

Storage of raw materials
Cooking and drying (sterilization)
Condensation
Fat extraction
Meal handling.

Poultry blood, feathers and offal, hatchery wastes, and dead birds reach the reactor (cooker) in different ways. Hydrolysis and sterilization occur in the cooker where the materials are heated to an established temperature and pressure for a given time. Then, the material is dried at the lowest possible temperature to preserve the quality of the product. Condensation of the vapors is required according to environmental regulations. The end product after drying is ground and sieved. Finally, the product prepared this way can have a fat content higher than 16%; therefore, fat extraction (e.g., the lard drains through the perforated false bottom to an adjacent tank) is required to ensure a lower fat content of 10-12%. The extracted fat can be used as an addition for feed and for other purposes (El Boushy and Van der Poel, 1994).

Sterilization occurs during cooking. Drying is accomplished in a separate drier. Two different types of driers have been used: the disc drier and the flash drier. The flash drier is the most common with benefits such as lower floor space, heating made by oil or gas, and a high-quality end-product (El Boushy and Van der Poel, 1994).

The rendering process can be used to treat different wastes or generate different products such as:

Feather meal (FM), using chicken feathers only.
Poultry by-product meal or offal meal, from offal (viscera, heads, feet, and blood).
Mixed poultry by-product meal (PBM), from the mixture of poultry offal and chicken feathers.

The composition and nutritional value for feather meals and poultry by-product meals using different processing conditions are shown in Tables 60-63.

TABLE 60

Composition of poultry by-product meal

| % Total weight | Fresh | Dry matter |
|---|---|---|
| Moisture | 6.1 | — |
| Crude protein | 54.6 | 58.1 |
| Ether extract | 14.9 | 15.9 |
| Crude fiber | 0.8 | 0.9 |
| Ash | 17.0 | 18.1 |
| Nitrogen free extract | 6.6 | 7.0 |
| Calcium | 8.0 | 8.5 |
| Phosphorus | 3.0 | 3.2 |

TABLE 61

Offal meals composition using rendering process in different industrial plants (McNaughton et al., 1977)

| | Plant 1 | Plant 2 | Plant 3 |
|---|---|---|---|
| Crude protein | 53.99 | 53.10 | 54.01 |
| Crude fat | 25.34 | 25.20 | 24.70 |
| Ash | 5.52 | 5.96 | 6.06 |
| Moisture | 11.15 | 11.01 | 9.98 |
| Crude fiber | 4.00 | 4.73 | 5.25 |
| Calcium | 1.46 | 1.65 | 1.78 |
| Phosphorus | 1.00 | 1.08 | 1.10 |

Values in percentage of total weight

TABLE 62

Amino acid content of feed from different poultry waste processes (El Boushy and Van der Poel, 1994)

| Amino acid | FM (batch) | FM (continuous) | PBM (batch) | PBM (continuous) |
|---|---|---|---|---|
| ASP | 5.90 | 5.75 | 5.20 | 5.17 |
| THR | 4.05 | 4.35 | 2.40 | 2.33 |
| SER | 7.50 | 9.25 | 2.70 | 2.70 |
| GLU | 10.10 | 10.35 | 9.83 | 9.70 |
| PRO | 9.55 | 8.85 | 6.43 | 6.50 |
| GLY | 6.75 | 6.85 | 7.87 | 7.40 |
| ALA | 5.35 | 4.75 | 4.43 | 4.93 |
| VAL | 5.40 | 5.80 | 2.87 | 3.03 |
| CYS | 2.60 | 3.00 | 0.63 | 0.60 |
| MET | 0.50 | 0.40 | 1.07 | 1.43 |
| ILE | 4.15 | 4.25 | 2.23 | 2.30 |
| LEU | 7.00 | 7.25 | 4.20 | 4.37 |
| TYR | 2.35 | 2.40 | 1.80 | 2.00 |
| PHE | 4.30 | 4.10 | 2.40 | 2.53 |
| LYS | 1.80 | 1.90 | 3.70 | 3.80 |
| HIS | 0.60 | 0.55 | 1.10 | 1.20 |
| ARG | 6.65 | 6.60 | 4.77 | 4.77 |
| Crude protein | 84.55 | 86.40 | 63.63 | 64.76 |

FM Feather meal (batch) 30-60 min, 207-690 kPa, ~150° C.
(continuous) 6-15 min, 483-690 kPa, ~150° C.
PBM Poultry by-product meal (blood, feathers and offal), batch or continuous, 30-40 min, 380 kPa, 142° C.

TABLE 63

Amino acid content and availability of different poultry wastes (El Boushy and Van der Poel, 1994)

|  | FM | Availability | PBM | Availability |
|---|---|---|---|---|
| ASP | 5.02 | 56 | 5.46 | 67 |
| GLU | 7.96 | 62 | 8.00 | 77 |
| SER | 6.73 | 64 | 6.09 | 81 |
| HIS | 0.55 | 59 | 1.08 | 72 |
| GLY | 4.47 | — | 6.59 | — |
| THR | 3.36 | 62 | 3.22 | 76 |
| ALA | 4.85 | 78 | 4.35 | 78 |
| ARG | 5.44 | 77 | 5.45 | 84 |
| TYR | 2.23 | 65 | 2.52 | 77 |
| VAL | 6.41 | 75 | 4.81 | 77 |
| MET | 0.79 | 65 | 1.14 | 77 |
| PHE | 3.89 | 77 | 3.63 | 79 |
| ILE | 4.15 | 78 | 3.25 | 79 |
| LEU | 6.19 | 73 | 5.78 | 78 |
| LYS | 1.57 | 64 | 2.81 | 77 |
| PRO | 9.39 | 71 | 6.13 | 77 |
| CYS | 4.26 | 65 | 2.43 | 62 |

Feather meal contains about 85% of crude protein; it is rich in cysteine, threonine and arginine, but deficient in methionine, lysine, histidine, and tryptophan (El Boushy and Roodbeen, 1980). Adding synthetic amino acids or other materials rich in the latter amino acids would improve the quality of the product. At high pressures, the chicken feathers tend to "gum" giving a non free-flowing meal.

Offal and feathers were obtained from the Texas A&M Poultry Science Department. The offal used contains bones, heads, beaks, feet, and internal organs (e.g., heart, lungs, intestine, liver). The offal was blended for 10 min in an industrial blender, collected in plastic bottles and finally frozen at −4° C. for later use. Samples of this blended material were used to obtain the moisture content, the total nitrogen (estimate of the protein fraction), and the amino acid content to characterize the starting material. Feathers were washed several times with water, air-dried at ambient temperature, dried at 105° C. and finally ground using a Thomas-Wiley laboratory mill (Arthur H. Thomas Company, Philadelphia, Pa.), and sieved through a 40-mesh screen.

The experiments were performed in two autoclave reactors (12-L, and 1-L) with a temperature controller and a mixer powered by a variable-speed motor. The conditions studied were established from previous experiments with both chicken feathers and chicken offal. The treatment conditions include temperature, raw material concentration (dry offal+feathers/L), calcium hydroxide loading (g $Ca(OH)_2$/g dry offal+feathers), and time. Samples were taken from the reactor at different times and then they were centrifuged to separate the liquid phase from the residual solid material.

Figure 35:
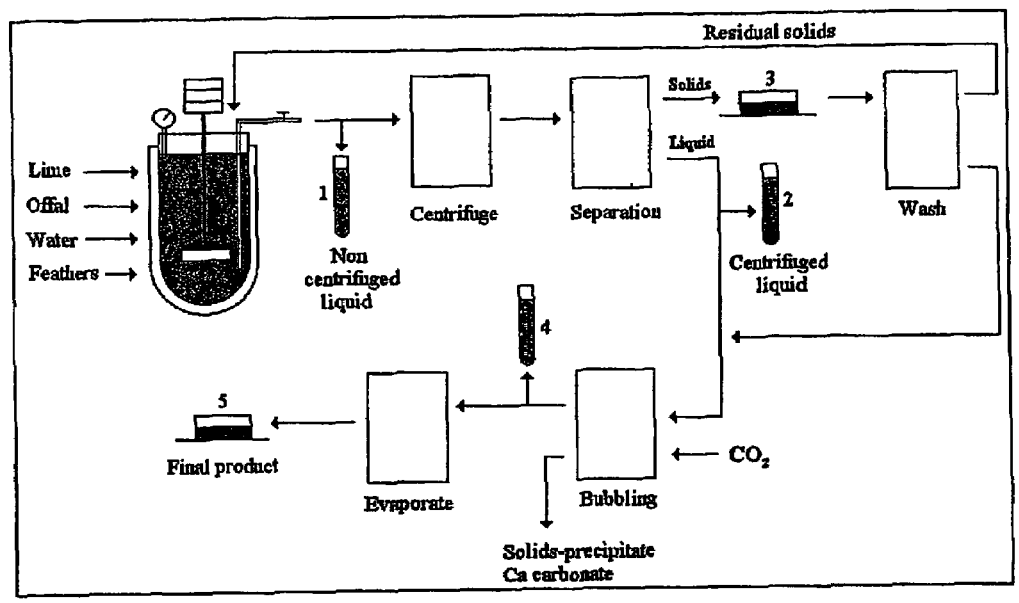
FIG. 35 illustrates a setup for generating amino acid-rich feather products using feathers and offal as raw materials. 1 is a non-centrifuges liquid. 2 is the centrifuged liquid after lime treatment. 3 is the residual solids after lime treatment. 4 is the centrifuged liquid after carbon dioxide bubbling. 5 is the final product.

A group of steps were followed such that data were collected for the different intermediate products for the process shown in FIG. 35.

The raw offal was 33.4% dry material and 66.6% moisture. The crude protein concentration of the dry offal was ~34% (offal TKN 5.40%) and the ash content was ~10%; the remaining 56% was fiber and fat. Amino acid analysis (Table 64) of the solid raw offal shows a good balance for all amino acids. The total protein content from the amino acid analysis is 26 g protein/100 g dry offal (Table 65). Considering that some amino acids were destroyed during the acid hydrolysis used in the HPLC determination and that Kjeldhal (TKN) values approximate the protein content, these two values are similar.

TABLE 64

Amino acid analysis for the dry raw offal

| Amino acid | Concentration (mg/L) | Percentage (g amino acid/100 g protein) |
|---|---|---|
| ASP | 29.565 | 9.900 |
| GLU | 50.559 | 16.930 |
| SER | 12.453 | 4.170 |
| HIS | 5.826 | 1.951 |
| GLY | 22.557 | 7.553 |
| THR | 12.409 | 4.155 |
| ALA | 20.943 | 7.013 |
| ARG | 22.753 | 7.619 |
| TYR | 10.015 | 3.354 |
| VAL | 15.172 | 5.080 |
| MET | 6.894 | 2.309 |
| PHE | 13.456 | 4.506 |
| ILE | 13.100 | 4.387 |
| LEU | 28.257 | 9.462 |
| LYS | 20.266 | 6.786 |
| PRO | 14.409 | 4.825 |

TABLE 65

Determination of amino acid content for dry raw offal sample

| Variable | Value |
|---|---|
| Total amino acid concentration (mg/L) | 298.63 |
| Total mass of amino acid in solid sample (mg) | 23.89 |
| Mass of solid sample for analysis (mg) | 92 |
| Percent of amino acid in dry sample | 26 |

The chicken feathers were 92% dry material and 8% moisture. The crude protein concentration of the dry feathers was about 95.7% (feathers TKN 15.3%); the remaining 4.3% was fiber and ash.

Experiment 1.

Whole Offal Hydrolysis

Experiment 1 compares the protein solubilization of the complete offal sample (bones, heads, beaks, feet, and internal organs) with a sample that only used internal organs, which was conducted previously (Chapter V). The conditions used in Experiment I were 75° C., 0.10 g lime/g offal, and 40 g dry offal/L. The experimental conditions studied and variables measured are summarized in Table 66.

TABLE 66

Experimental conditions and variables measured to determine the protein solubilization of the offal sample with bones, heads, beaks, feet, and internal organs

| Variable | Value |
|---|---|
| Temperature (° C.) | 75 |
| Mass of Ca(OH)$_2$ (g) | 3.5 |
| Mass of Offal (g) | 102.1 |
| Volume of water (mL) | 850 |
| Lime loading (g Ca(OH)$_2$/g dry offal) | 0.103 |
| Dry offal concentration (g dry offal/L) | 40.05 |
| Residual solid (g) | 14.2 |

Table 67 shows the total nitrogen content in the centrifuged liquid samples as a fraction of time for this experiment. On the basis of the average TKN for dry offal (5.40%), the protein hydrolysis conversions were estimated and given in Table 68.

TABLE 67

Protein and mineral content of raw offal and products after lime hydrolysis

| Condition | TKN (%) | P (%) | K (%) | Ca (%) | Mg (%) | Na (ppm) | Zn (ppm) | Fe (ppm) | Cu (ppm) | Mn (ppm) |
|---|---|---|---|---|---|---|---|---|---|---|
| Dry Offal | 5.3995 | 0.6269 | 0.9181 | 0.3845 | 0.0622 | 3150 | 59 | 493 | 46 | 10 |
| Liquid 30 min | 0.1189 | 0.0041 | 0.0311 | 0.0539 | 0.001 | 104 | 0 | 11 | 0 | 0 |
| Liquid 90 min (*) | 0.1925 | 0.0187 | 0.0321 | 0.2 | 0.0031 | 104 | 2 | 9 | 2 | 0 |
| Liquid 90 min | 0.1145 | 0.0041 | 0.0311 | 0.0487 | 0.001 | 104 | 0 | 3 | 0 | 0 |
| Dry residual solid | 2.5867 | 0.5606 | 0.1005 | 4.1793 | 0.1078 | 560 | 97 | 187 | 58 | 15 |

(*) Non-centrifuged sample.

TABLE 68

Percentage conversion of the total TKN to soluble TKN

| Sample | Conversion |
|---|---|
| Centrifuged liquid 30 min | 59.4 |
| Non-centrifuged liquid 90 min | 96.2 |
| Centrifuged liquid 90 min | 57.2 |

At the condition studied, the conversion of nitrogen in the solid phase to the liquid phase was 60% efficient. This value is lower than the one obtained for the same conditions in the previous example but it can be explained by the presence of bones, heads, beaks, and feet, which were not present before. These parts contain higher percentage of ash, minerals, and non-soluble components that reduce the efficiency of the hydrolysis process. The protein hydrolysis did not change between 30 min and 90 min (Table 68), similar to previous results; 30 min is the recommended time to avoid possible degradation of the heat-sensitive amino acids. No important loss of nitrogen occurred during the hydrolysis (96.2% is accounted for in the non-centrifuged sample).

An important reduction (approximately 50%) of protein in the solid is achieved, going from 33.7% in the raw offal to 16.2% (similar to the 13.3% value obtained from the amino acid analysis, Table 69) in the residual solid after lime treatment. There is also a 58% weight reduction of dry solid due to solubilization of amino acids and other soluble components present in the raw offal. This residual solid is stable, with no strong odors, and it has a well-balanced amino acid content (Table 70) that meets, or exceeds, the essential amino acids requirements of the animals during their growth phase.

TABLE 69

Determination of amino acid content for residual solid after lime treatment

| Variable | Value |
|---|---|
| Total amino acid concentration (mg/L) | 180.50 |
| Total mass of amino acid in solid sample (mg) | 13.54 |
| Mass of solid sample for analysis (mg) | 102 |
| Percent of amino acid in dry sample | 13.27 |

TABLE 70

Amino acid analysis for the residual solid after lime treatment

| Amino acid | Concentration (mg/L) | Percentage (g amino acid/100 g protein) |
|---|---|---|
| ASP | 19.289 | 10.686 |
| GLU | 25.776 | 14.280 |
| SER | 8.512 | 4.716 |
| HIS | 4.314 | 2.390 |
| GLY | 9.178 | 5.085 |
| THR | 8.314 | 4.606 |
| ALA | 10.392 | 5.757 |
| ARG | 12.771 | 7.075 |
| TYR | 7.805 | 4.324 |
| VAL | 10.546 | 5.843 |

TABLE 70-continued

Amino acid analysis for the residual solid after lime treatment

| Amino acid | Concentration (mg/L) | Percentage (g amino acid/100 g protein) |
|---|---|---|
| MET | 4.967 | 2.752 |
| PHE | 10.376 | 5.749 |
| ILE | 9.545 | 5.288 |
| LEU | 20.762 | 11.502 |
| LYS | 9.858 | 5.462 |
| PRO | 8.096 | 4.485 |

The treatment of chicken offal with lime hydrolyzes the protein present into small peptides and free amino acids, which are soluble in water. Therefore, the 60% TKN conversion from the solid phase to the liquid phase represents the efficiency of recovering protein in the liquid phase. Table 71 shows the amino acid balance for this centrifuged liquid.

TABLE 71

Amino acid analysis for the centrifuged liquid sample (30 min)

| Amino acid | Concentration (mg/L) | Percentage (g amino acid/100 g protein) |
|---|---|---|
| ASP | 69.983 | 3.530 |
| GLU | 129.448 | 6.529 |
| ASN | 3.937 | 0.199 |
| SER | 98.378 | 4.962 |
| GLN | 26.346 | 1.329 |
| HIS | 25.379 | 1.280 |
| GLY | 69.551 | 3.508 |
| THR | 73.033 | 3.684 |
| CIT | 54.309 | 2.739 |
| B-ALA | 4.170 | 0.210 |
| ALA | 147.275 | 7.428 |
| TAU | 200.813 | 10.129 |
| ARG | 162.465 | 8.195 |
| TYR | 93.992 | 4.741 |
| CYS-CYS | 102.601 | 5.175 |
| VAL | 80.385 | 4.055 |
| MET | 51.049 | 2.575 |
| TRP | 36.910 | 1.862 |
| PHE | 86.256 | 4.351 |
| ILE | 74.689 | 3.767 |
| LEU | 179.141 | 9.036 |
| LYS | 136.399 | 6.880 |
| PRO | 76.073 | 3.837 |

Total amino acid concentration 1982.6 mg/L.

A comparison of the amino acid content of the raw offal, the centrifuged liquid product, and the residual solid (Table 72) shows that the amino acid contents in the centrifuged liquid and the residual solid are comparable to the raw offal. This implies that the solubilization of all amino acids occurs at a similar rate and that there is little destruction of specific amino acids for the conditions studied.

TABLE 72

Comparison of amino acid content for the different materials during lime treatment of chicken offal

| Amino acid | Offal | Residual solid | Centrifuged Liquid* |
|---|---|---|---|
| ASP | 9.90 | 10.69 | 4.50 |
| GLU | 16.93 | 14.28 | 8.33 |
| SER | 4.17 | 4.72 | 6.33 |
| HIS | 1.95 | 2.39 | 1.63 |
| GLY | 7.55 | 5.08 | 4.48 |
| THR | 4.16 | 4.61 | 4.70 |
| ALA | 7.01 | 5.76 | 9.48 |
| ARG | 7.62 | 7.08 | 10.46 |
| TYR | 3.35 | 4.32 | 6.05 |
| VAL | 5.08 | 5.84 | 5.17 |
| MET | 2.31 | 2.75 | 3.29 |
| PHE | 4.51 | 5.75 | 5.55 |
| ILE | 4.39 | 5.29 | 4.81 |
| LEU | 9.46 | 11.50 | 11.53 |
| LYS | 6.79 | 5.46 | 8.78 |
| PRO | 4.83 | 4.49 | 4.90 |

*Considering only the amino acids present in the solid analysis.

The treatment of chicken offal with lime at medium temperature and time reduces the amount of microorganisms present in the liquid phase. Rapid evaporation of the liquid is essential because the liquid medium contains all the nutritional requirements for bacterial growth.

The amino acid analysis of the samples (Table 73) shows again a very well balanced product that meets, or exceeds, the essential amino acids requirements of the animals during their growth phase. A slightly low value is obtained for histidine.

TABLE 73

Amino acid analysis of raw material and products, compared with the essential amino acids requirements for various domestic animals (whole offal)

| Amino acid | Catfish | Dogs | Cats | Chickens | Pigs | Centrifuged liquid | Solid offal | Residual Solid |
|---|---|---|---|---|---|---|---|---|
| ASN | | | | | | 0.20 | | |
| GLN | | | | | | 1.33 | | |
| ASP | | | | | | 3.53 | 9.90 | 10.69 |
| GLU | | | | | | 6.53 | 16.93 | 14.28 |
| SER | | | | | | 4.96 | 4.17 | 4.72 |
| HIS | 1.31 | 1.00 | 1.03 | 1.40 | 1.25 | 1.28 | 1.95 | 2.39 |
| GLY | | | | | | 3.51 | 7.55 | 5.08 |
| THR | 1.75 | 2.64 | 2.43 | 3.50 | 2.50 | 3.68 | 4.16 | 4.61 |

TABLE 73-continued

Amino acid analysis of raw material and products, compared with the essential amino acids requirements for various domestic animals (whole offal)

| Amino acid | Catfish | Dogs | Cats | Chickens | Pigs | Centrifuged liquid | Solid offal | Residual Solid |
|---|---|---|---|---|---|---|---|---|
| ALA |  |  |  |  |  | 7.43 | 7.01 | 5.76 |
| ARG | 3.75 | 2.82 | 4.17 | 5.50 | 0.00 | 8.19 | 7.62 | 7.08 |
| VAL | 2.63 | 2.18 | 2.07 | 4.15 | 2.67 | 4.05 | 5.08 | 5.84 |
| CYS | 2.00+ | 2.41+ | 3.67+ | 4.00+ | 1.92+ | 5.18 | ND | ND |
| MET | 2.00+ | 2.41+ | 2.07 | 2.25 | 1.92+ | 2.57 | 2.31 | 2.75 |
| TYR | 4.38* | 4.05* | 2.93* | 5.85* | 3.75* | 4.74 | 3.35 | 4.32 |
| PHE | 4.38* | 4.05* | 1.40 | 3.15 | 3.75* | 4.35 | 4.51 | 5.75 |
| ILE | 2.28 | 2.05 | 1.73 | 3.65 | 2.50 | 3.77 | 4.39 | 5.29 |
| LEU | 3.06 | 3.27 | 4.17 | 5.25 | 2.50 | 9.04 | 9.46 | 11.50 |
| LYS | 4.47 | 3.50 | 4.00 | 5.75 | 3.58 | 6.88 | 6.79 | 5.46 |
| TRIP | 0.44 | 0.91 | 0.83 | 1.05 | 0.75 | 1.86 | ND | ND |
| PRO |  |  |  |  |  | 3.84 | 4.83 | 4.49 |

*Cysteine + Methionine
+Tyrosine + Phenylalanine
ND Not determined
Values expressed as g individual amino acid per 100 g total amino acids.

Experiment 2.

Offal and Feather Processing

Chicken feathers and offal have different compositions and their main components behave differently during protein hydrolysis with lime. Keratin protein is harder to hydrolyze than the proteins in offal, requiring longer times or higher temperatures and lime concentrations. The residual wastes from slaughterhouses often contain mixtures of offal and feathers making the treatment of this mixture a possibility for obtaining a protein-rich product. Two products could be generated: one with a well-balanced amino acid content that could meet the amino acid requirements for various monogastric domestic animals (from the offal), and a second one for ruminants (from the feathers).

Hydrolysis of a chicken feather/offal mixture was studied using the process shown in FIG. 35. The initial treatment of the mixture was done to hydrolyze mainly the protein present in offal to obtain a liquid product and a residual solid. Bubbling the liquid product with $CO_2$ precipitated $CaCO_3$ (that can be converted back to lime) and reduced the concentration of Ca in the liquid phase. The final evaporation of this liquid yields the first solid amino acid-rich product.

The residual solid of Phase 1 was returned to the reactor to further treat with lime at longer times (different conditions) to promote the hydrolysis of the chicken feather protein. Steps similar to the Phase 1 will be followed to obtain the second product.

Experiments AI, B1, and C1 used Condition 1 whereas Experiments A2, B2, and C2 used Condition 2.

The experimental conditions studied and variables measured during Experiment 2 are summarized in Table 74. A ratio of 17.5 g wet offal/7 g wet feathers was used because it is a normal value in the waste generation of a slaughterhouse.

TABLE 74

Experimental conditions and variables measured to determine the protein solubilization of the offal/feather mixture

| Variable | Exp. A1 | Exp. A2 | Exp. B1 | Exp. B2 | Exp. C1 | Exp. C2 |
|---|---|---|---|---|---|---|
| Temperature (° C.) | 50 | 75 | 75 | 75 | 75 | 100 |
| Mass of Ca(OH)$_2$ (g) | 36 | 41.4 | 20.7 | 20.7 | 4.8 | 2.7 |
| Mass of offal (g) | 685 |  | 343 |  | 91.3 |  |
| Mass of feathers (g) | 274 | 410 | 137 | 211.8 | 36.5 | 48.7 |
| Volume of water (mL) | 6000 | 3000 | 3000 | 2000 | 800 | 800 |
| Ca(OH)$_2$ (g/d dry offal) | 0.075 | 0.101 | 0.086 | 0.098 | 0.075 | 0.055 |
| Dry matter (g/L) | 80.08 | 136.53 | 80.13 | 105.79 | 80.02 | 60.81 |
| Dry Offal (g/L) | 38.06 |  | 38.12 |  | 38.05 |  |
| Total TKN (g) | 50.94 |  | 25.48 |  | 6.79 |  |
| TKN (%) | 10.60 |  | 10.60 |  | 10.60 |  |

Table 75 shows the total nitrogen content in the centrifuged liquid samples as a function of time for this experiment. The average TKN for dry offal (5.40%) and chicken feathers (15.3%) gave a mixture initial TKN of 10.6%. Protein hydrolysis conversions were estimated and are given in Table 76 and Table 77. Table 76 considers the conversion with respect to the offal first (Condition 1) and feathers second (Condition 2), whereas Table 77 gives the conversion with respect to the initial TKN of the mixture. At the conditions studied, the highest conversion of nitrogen in the solid phase to the liquid phase was 60%.

TABLE 75

Total Kjeldhal nitrogen content in the centrifuged liquid phase as a function of time for Experiment 2 (offal/feathers mixture)

| Time (min) | Exp. A1 | Exp. A2 | Exp. B1 | Exp. B2 | Exp. C1 | Exp. C2 |
|---|---|---|---|---|---|---|
| 5 | 0.1126 | 0.1015 | — | 0.1183 | — | — |
| 10 | 0.1210 | — | 0.1109 | — | — | — |
| 15 | 0.1154 | 0.0973 | 0.1238 | 0.1262 | — | — |
| 30 | 0.1182 | 0.1126 | 0.1182 | 0.1431 | — | — |
| 60 | — | 0.1514 | 0.1349 | 0.1723 | 0.2300 | — |
| 120 | — | 0.2188 | — | 0.2299 | — | 0.2600 |

TKN in g nitrogen/100 g liquid sample.

TABLE 76

Percentage conversion of the total TKN to soluble TKN for Experiment 2, with respect to offal (A1, B1 and C1) and feathers (A2, B2 and C2) TKN respectively

| Time (min) | Exp. A1 | Exp. A2 | Exp. B1 | Exp. B2 | Exp. C1 | Exp. C2 |
|---|---|---|---|---|---|---|
| 5 | 59.2 | 7.9 | — | 12.3 | — | — |
| 10 | 63.6 | — | 58.2 | — | — | — |
| 15 | 60.6 | 7.6 | 64.9 | 13.1 | — | — |
| 30 | 62.1 | 8.7 | 62.0 | 14.8 | — | — |
| 60 | — | 11.8 | 70.8 | 17.9 | 120.9 | — |
| 120 | — | 17.0 | — | 23.8 | — | 26.9 |

TABLE 77

Percentage conversion of the total TKN to soluble TKN for Experiment 2 (offal/feathers mixture)

| Time (min) | Exp. A1 | Exp. A2 | Exp. B1 | Exp. B2 | Exp. C1 | Exp. C2 |
|---|---|---|---|---|---|---|
| 5 | 14.3 | 6.0 | — | 9.3 | — | — |
| 10 | 15.4 | — | 14.1 | — | — | — |
| 15 | 14.7 | 5.7 | 15.7 | 9.9 | — | — |
| 30 | 15.0 | 6.6 | 15.0 | 11.2 | — | — |
| 60 | — | 8.9 | 17.2 | 13.5 | 29.3 | — |
| 120 | — | 12.9 | — | 18.0 | — | 30.7 |
| Total | | 27.9 | | 35.2 | | 60 |

Based on the data in Table 76, no significant effect on conversion occurs when changing the temperature from 50 to 75° C. Results from Experiments A1 and B1 show a higher conversion at 60 min compared to 30 min; this is expected because keratin protein hydrolyzes slower and continues to react while contacting the lime. Also, comparing Table 68 and Table 76, similar results are obtained for the conversion of the offal/chicken feather mixture as for offal alone; hence, the offal present in the mixture hydrolyzes at the same rate as the offal alone. At the temperatures studied in Experiments A1 and B1, the hydrolysis of chicken feathers is relatively slow compare to offal. The protein hydrolysis increases significantly by changing the temperature from 75 to 100° C. (Experiment C1) for Condition 1. This result is explained by the higher conversion expected for the chicken feathers at this condition, 60% for chicken feathers hydrolysis at 2 h (Chang and Holtzapple, 1999).

Results from Experiments A2 and B2 show that the initial "pretreatment" of the chicken feathers in a mixture with chicken offal slightly increases the hydrolysis conversion for the feathers (17% to 23.8%), and that higher temperatures or longer times might be required to completely hydrolyze the chicken feathers. Results from Experiment C2 show a higher conversion at 100° C. compared to 75° C. From the Chang and Holtzapple study, an even higher temperature or a longer reaction time could be used to further increase the protein hydrolysis.

Tables 78-80 show the total nitrogen and mineral content of the samples from the different steps of the lime treatment process of the offal/feather mixture. A slight reduction of calcium content (8%) is obtained after bubbling the liquid with $CO_2$ until a pH of ~6 is achieved. This reduction is accompanied by a similar reduction of nitrogen content (Table 78). These results show that calcium precipitation with $CO_2$ is a very inefficient process for the conditions studied.

TABLE 78

Protein and mineral content of products after lime hydrolysis for Experiments A1 & A2

| | TKN (%) | P (%) | K (%) | Ca (%) | Mg (%) | Na (ppm) | Zn (ppm) | Fe (ppm) | Cu (ppm) | Mn (ppm) |
|---|---|---|---|---|---|---|---|---|---|---|
| With solids (30 min) | 0.4257 | | | | | | | | | |
| Liquid 1 (30 min) | 0.1182 | 0.0093 | 0.0404 | 0.0746 | 0.001 | 259 | 0 | 3 | 1 | 0 |
| After bubbling | 0.1098 | 0.0083 | 0.0352 | 0.0684 | 0 | 207 | 0 | 2 | 1 | 0 |
| With solids (2 h) | 0.5420 | | | | | | | | | |
| Liquid 2 (2 h) | 0.2188 | 0.0041 | 0.0197 | 0.1523 | 0 | 155 | 1 | 6 | 1 | 0 |
| After bubbling | 0.2108 | 0.0031 | 0.0176 | 0.1503 | 0 | 145 | 1 | 2 | 1 | 0 |
| Residual Solid 1 | 9.0254 | 0.571 | 0.3119 | 4.0974 | 0.0756 | 3264 | 104 | 210 | 35 | 13 |
| Residual Solid 2 | 7.9002 | 0.2974 | 0.1492 | 5.6684 | 0.1109 | 2694 | 104 | 301 | 31 | 16 |

TABLE 79

Protein and mineral content of products after lime hydrolysis for Experiments B1 & B2

| | TKN (%) | P (%) | K (%) | Ca (%) | Mg (%) | Na (ppm) | Zn (ppm) | Fe (ppm) | Cu (ppm) | Mn (ppm) |
|---|---|---|---|---|---|---|---|---|---|---|
| With solids (60 min) | 0.4257 | | | | | | | | | |
| Liquid 1 (60 min) | 0.1349 | 0.0104 | 0.0383 | 0.0984 | 0.001 | 259 | 1 | 5 | 1 | 0 |

TABLE 79-continued

Protein and mineral content of products after lime hydrolysis for Experiments B1 & B2

| | TKN (%) | P (%) | K (%) | Ca (%) | Mg (%) | Na (ppm) | Zn (ppm) | Fe (ppm) | Cu (ppm) | Mn (ppm) |
|---|---|---|---|---|---|---|---|---|---|---|
| With solids (2 h) | 0.5926 | | | | | | | | | |
| Liquid 2 (2 h) | 0.2299 | 0.0031 | 0.0166 | 0.1668 | 0 | 135 | 1 | 2 | 1 | 0 |
| Residual Solid 1 | 8.7163 | | | | | | | | | |
| Residual Solid 2 | 8.0355 | 0.313 | 0.0705 | 5.9482 | 0.0839 | 2518 | 77 | 166 | 20 | 9 |

TABLE 80

Protein and mineral content of products after lime hydrolysis for Experiments C1 & C2

| | TKN (%) | P (%) | K (%) | Ca (%) | Mg (%) | Na (ppm) | Zn (ppm) | Fe (ppm) | Cu (ppm) | Mn (ppm) |
|---|---|---|---|---|---|---|---|---|---|---|
| Liquid 1 (60 min) | 0.23 | 0 | 0.04 | 0.1 | 0 | 228 | 2 | 1 | 0 | 0 |
| Liquid 2 (2 h) | 0.26 | 0 | 0.01 | 0.14 | 0 | 83 | 1 | 1 | 0 | 0 |
| Residual Solid 1 | 12.79 | 0.3 | 0.32 | 2.92 | 0.05 | 1617 | 73 | 152 | 19 | 5 |
| Residual Solid 2 | 9.77 | 0.53 | 0.09 | 4.29 | 0.09 | 819 | 95 | 269 | 24 | 9 |
| Final product | 11.71 | 0.12 | 0.55 | 5.17 | 0.01 | 2912 | 38 | 21 | 11 | 8 |

Table 79 shows that after the second lime treatment, the protein content in the solid goes from 10.6% (TKN) in the raw mixture to 7.9% (TKN) in the final residual solid, about a 25% reduction. Also, there is approximately 35% reduction in total dry weight (soluble matter). This residual solid is stable, with no strong odors, a relatively high concentration of calcium (~6% for all cases), and an amino acid content poor in several amino acids that are required for animal growth; similar to the residual obtained for chicken feathers only.

Because the concentration of calcium is high in Residual Solid #1, for all the cases, a lower amount of lime might be added to the second lime treatment with a similar result for the protein hydrolysis conversion.

The concentrations of all the minerals are compared for all the cases studied (Tables 78-80). The nitrogen content in the Centrifuged Liquid #1 and #2 increases with the highest temperature. The mineral content (phosphorus, potassium, and sodium) decreases from Liquid #1 to Liquid #2 as more salts are solubilized with temperature and time.

Tables 81-83 show the amino acid content for the different liquid products obtained at the conditions studied. For Experiments A2 and B2 the samples were hydrolyzed with HCL for 24 h before the amino acid analysis to determine the total amino acids concentration from the chicken feather hydrolysis. In Experiment C2 no hydrolysis was performed for comparison purposes.

TABLE 81

Amino acid analysis for the centrifuged liquid sample in Experiments A1 and A2

| | Experiment A1 | | Experiment A2 | |
|---|---|---|---|---|
| Amino acid | Concentration (mg/L) | Percentage (g amino acid/100 g protein) | Concentration (mg/L) | Percentage (g amino acid/100 g protein) |
| ASP | 205.70 | 5.12 | 412.20 | 7.50 |
| GLU | 454.38 | 11.30 | 649.67 | 11.81 |
| ASN | 9.92 | 0.25 | 40.51 | 0.74 |
| SER | 235.14 | 5.85 | 351.29 | 6.39 |
| GLN | 0.00 | 0.00 | 0.00 | 0.00 |
| HIS | 50.93 | 1.27 | 0.00 | 0.00 |
| GLY | 170.00 | 4.23 | 365.21 | 6.64 |
| THR | 149.34 | 3.72 | 131.27 | 2.39 |
| CIT | 53.03 | 1.32 | 99.38 | 1.81 |
| B-ALA | 6.44 | 0.16 | 4.72 | 0.09 |
| ALA | 276.72 | 6.88 | 443.72 | 8.07 |
| TAU | 389.12 | 9.68 | 106.69 | 1.94 |
| ARG | 298.98 | 7.44 | 256.01 | 4.66 |
| TYR | 178.99 | 4.45 | 378.28 | 6.88 |
| CYS-CYS | 109.61 | 2.73 | 127.71 | 2.32 |
| VAL | 164.71 | 4.10 | 490.55 | 8.92 |
| MET | 110.56 | 2.75 | 99.93 | 1.82 |
| TRP | 68.81 | 1.71 | 46.19 | 0.84 |
| PHE | 162.55 | 4.04 | 236.89 | 4.31 |
| ILE | 141.70 | 3.52 | 334.24 | 6.08 |
| LEU | 351.04 | 8.73 | 578.80 | 10.53 |
| LYS | 305.46 | 7.60 | 283.56 | 5.16 |
| PRO | 126.91 | 3.16 | 62.32 | 1.13 |
| Total Conc. | 4020.04 | | 5499.14 | |

TABLE 82

Amino acid analysis for the centrifuged liquid sample in Experiments B1 and B2

| | Experiment B1 | | Experiment B2 | |
|---|---|---|---|---|
| Amino acid | Concentration (mg/L) | Percentage (g amino acid/100 g protein) | Concentration (mg/L) | Percentage (g amino acid/100 g protein) |
| ASP | 208.38 | 4.88 | 606.53 | 8.23 |
| GLU | 455.89 | 10.69 | 788.25 | 10.70 |
| ASN | 9.39 | 0.22 | 0.00 | 0.00 |
| SER | 245.38 | 5.75 | 943.75 | 12.81 |
| GLN | 20.55 | 0.48 | 0.00 | 0.00 |
| HIS | 51.98 | 1.22 | 0.00 | 0.00 |
| GLY | 194.49 | 4.56 | 956.65 | 12.98 |
| THR | 161.33 | 3.78 | 166.24 | 2.26 |
| CIT | 67.51 | 1.58 | 0.00 | 0.00 |
| B-ALA | 9.57 | 0.22 | 0.00 | 0.00 |
| ALA | 300.78 | 7.05 | 387.08 | 5.25 |
| TAU | 391.07 | 9.17 | 0.00 | 0.00 |
| ARG | 329.20 | 7.72 | 546.22 | 7.41 |
| TYR | 204.69 | 4.80 | 274.13 | 3.72 |
| CYS-CYS | 74.44 | 1.74 | 0.00 | 0.00 |
| VAL | 171.31 | 4.02 | 401.03 | 5.44 |
| MET | 118.50 | 2.78 | 102.84 | 1.40 |
| TRP | 41.72 | 0.98 | 0.00 | 0.00 |
| PHE | 161.73 | 3.79 | 370.28 | 5.03 |
| ILE | 138.92 | 3.26 | 330.31 | 4.48 |
| LEU | 363.99 | 8.53 | 684.05 | 9.28 |
| LYS | 345.67 | 8.10 | 106.63 | 1.45 |
| PRO | 199.60 | 4.68 | 704.17 | 9.56 |
| Total Conc. | 4266.10 | | 7368.15 | |

TABLE 83

Amino acid analysis for the centrifuged liquid sample in Experiments C1 and C2

| | Experiment C1 | | Experiment C2 | |
|---|---|---|---|---|
| Amino acid | Concentration m/L | Percentage (g amino acid/100 g protein) | Concentration m/L | Percentage (g amino acid/100 g protein) |
| ASP | 280.42 | 4.81 | 73.39 | 6.95 |
| GLU | 675.71 | 11.59 | 148.71 | 14.08 |
| ASN | 14.89 | 0.26 | 0.88 | 0.08 |
| SER | 244.52 | 4.20 | 99.68 | 9.44 |
| GLN | 0.00 | 0.00 | 0.00 | 0.00 |
| HIS | 80.50 | 1.38 | 0.00 | 0.00 |
| GLY | 249.11 | 4.27 | 91.98 | 8.71 |
| THR | 227.13 | 3.90 | 6.41 | 0.61 |
| CIT | 238.91 | 4.10 | 75.04 | 7.10 |
| B-ALA | 6.61 | 0.11 | 0.00 | 0.00 |
| ALA | 438.12 | 7.52 | 106.95 | 10.12 |
| TAU | 199.22 | 3.42 | 22.59 | 2.14 |
| ARG | 262.88 | 4.51 | 39.32 | 3.72 |
| TYR | 97.79 | 1.68 | 13.70 | 1.30 |
| CYS—CYS | 181.57 | 3.12 | 47.73 | 4.52 |
| VAL | 293.99 | 5.04 | 56.11 | 5.31 |
| MET | 148.91 | 2.55 | 14.41 | 1.36 |
| TRP | 113.75 | 1.95 | 0.00 | 0.00 |
| PHE | 258.51 | 4.44 | 48.00 | 4.54 |
| ILE | 270.12 | 4.63 | 54.45 | 5.15 |
| LEU | 599.13 | 10.28 | 107.36 | 10.16 |
| LYS | 408.43 | 7.01 | 25.54 | 2.42 |
| PRO | 537.85 | 9.23 | 24.20 | 2.29 |
| Total Conc. | 5828.07 | | 1056.46 | |

From Tables 81-83, a comparison of results from Experiments A1, B1, and C1 show similar amino acid contents for all cases; hence, the effect of temperature on the hydrolysis rate is similar for the different individual amino acids. The temperature increases the hydrolysis conversion (100° C. vs. 75° C., Table 76 and Table 77) but does not affect the amino acid content in the lime treatment of the chicken feather/offal mixture.

By comparing Experiments A1, B1, and C1 with the amino acid content for chicken offal only (Table 71), similar results are obtained in all cases. The amino acid content and protein hydrolysis of the chicken offal are not affected by the presence of chicken feathers in the mixture and the hydrolysis of these feathers is relatively small at the conditions studied. The increase in proline for the higher temperature can be explained by the hydrolysis of connecting tissue and bones (in offal) that probably requires higher temperature.

A comparison of results from Experiments A2, B2, and C2 show greater differences in the amino acid content than experiments AI, B1, and C1. The different amounts of non-hydrolyzed offal that remained in Residual Solid #1 for the different temperatures studied can explain these differences.

Table 84 and Table 85 compare the requirements for essential amino acids of various domestic animals with the different products.

TABLE 84

Amino acid analysis of raw material and products, compare with the essential amino acids requirements for various domestic animals (offal/feathers mixture Condition 1)

| Amino acid | Catfish | Dogs | Cats | Chickens | Pigs | Exp A1 | Exp B1 | Exp C1 |
|---|---|---|---|---|---|---|---|---|
| ASN | | | | | | 0.25 | 0.22 | 0.26 |
| GLN | | | | | | 0.00 | 0.48 | 0.00 |
| ASP | | | | | | 5.12 | 4.88 | 4.81 |
| GLU | | | | | | 11.30 | 10.69 | 11.59 |
| SER | | | | | | 5.85 | 5.75 | 4.20 |
| HIS | 1.31 | 1.00 | 1.03 | 1.40 | 1.25 | 1.27 | 1.22 | 1.38 |
| GLY | | | | | | 4.23 | 4.56 | 4.27 |
| THR | 1.75 | 2.64 | 2.43 | 3.50 | 2.50 | 3.72 | 3.78 | 3.90 |

TABLE 84-continued

Amino acid analysis of raw material and products, compare with the essential amino acids requirements for various domestic animals (offal/feathers mixture Condition 1)

| Amino acid | Catfish | Dogs | Cats | Chickens | Pigs | Exp A1 | Exp B1 | Exp C1 |
|---|---|---|---|---|---|---|---|---|
| ALA | | | | | | 6.88 | 7.05 | 7.52 |
| ARG | 3.75 | 2.82 | 4.17 | 5.50 | 0.00 | 7.44 | 7.72 | 4.51 |
| VAL | 2.63 | 2.18 | 2.07 | 4.15 | 2.67 | 4.10 | 4.02 | 5.04 |
| CYS | 2.00+ | 2.41+ | 3.67+ | 4.00+ | 1.92+ | 2.73 | 1.74 | 3.12 |
| MET | 2.00+ | 2.41+ | 2.07 | 2.25 | 1.92+ | 2.75 | 2.78 | 2.55 |
| TYR | 4.38* | 4.05* | 2.93* | 5.85* | 3.75* | 4.45 | 4.80 | 1.68 |
| PHE | 4.38* | 4.05* | 1.40 | 3.15 | 3.75* | 4.04 | 3.79 | 4.44 |
| ILE | 2.28 | 2.05 | 1.73 | 3.65 | 2.50 | 3.52 | 3.26 | 4.63 |
| LEU | 3.06 | 3.27 | 4.17 | 5.25 | 2.50 | 8.73 | 8.53 | 10.28 |
| LYS | 4.47 | 3.50 | 4.00 | 5.75 | 3.58 | 7.60 | 8.10 | 7.01 |
| TRP | 0.44 | 0.91 | 0.83 | 1.05 | 0.75 | 1.71 | 0.98 | 1.95 |
| PRO | | | | | | 3.16 | 4.68 | 9.23 |

*Phenylalanine + Tyrosine
+Cysteine + Methionine
All values are in g amino acid/100 g protein.

TABLE 85

Amino acid analysis of raw material and products, compare with the essential amino acids requirements for various domestic animals (offal/feathers mixture Condition 2)

| Amino acid | Catfish | Dogs | Cats | Chickens | Pigs | Exp A2 | Exp B2 | Exp C2 |
|---|---|---|---|---|---|---|---|---|
| ASN | | | | | | 0.74 | 0.00 | 0.08 |
| GLN | | | | | | 0.00 | 0.00 | 0.00 |
| ASP | | | | | | 7.50 | 8.23 | 6.95 |
| GLU | | | | | | 11.81 | 10.70 | 14.08 |
| SER | | | | | | 6.39 | 12.81 | 9.44 |
| HIS | 1.31 | 1.00 | 1.03 | 1.40 | 1.25 | 0.00 | 0.00 | 0.00 |
| GLY | | | | | | 6.64 | 12.98 | 8.71 |
| THR | 1.75 | 2.64 | 2.43 | 3.50 | 2.50 | 2.39 | 2.26 | 0.61 |
| ALA | | | | | | 8.07 | 5.25 | 10.12 |
| ARG | 3.75 | 2.82 | 4.17 | 5.50 | 0.00 | 4.66 | 7.41 | 3.72 |
| VAL | 2.63 | 2.18 | 2.07 | 4.15 | 2.67 | 8.92 | 5.44 | 5.31 |
| CYS | 2.00+ | 2.41+ | 3.67+ | 4.00+ | 1.92+ | 2.32 | 0.00 | 4.52 |
| MET | 2.00+ | 2.41+ | 2.07 | 2.25 | 1.92+ | 1.82 | 1.40 | 1.36 |
| TYR | 4.38* | 4.05* | 2.93* | 5.85* | 3.75* | 6.88 | 3.72 | 1.30 |
| PHE | 4.38* | 4.05* | 1.40 | 3.15 | 3.75* | 4.31 | 5.03 | 4.54 |
| ILE | 2.28 | 2.05 | 1.73 | 3.65 | 2.50 | 6.08 | 4.48 | 5.15 |
| LEU | 3.06 | 3.27 | 4.17 | 5.25 | 2.50 | 10.53 | 9.28 | 10.16 |
| LYS | 4.47 | 3.50 | 4.00 | 5.75 | 3.58 | 5.16 | 1.45 | 2.42 |
| TRP | 0.44 | 0.91 | 0.83 | 1.05 | 0.75 | 0.84 | 0.00 | 0.00 |
| PRO | | | | | | 1.13 | 9.56 | 2.29 |

*Phenylalanine + Tyrosine
+Cysteine + Methionine
All values are in g amino acid/100 g protein.

For the liquid product obtained after the first hydrolysis of the chicken feather/offal mixture, the tabulated results imply that the solubilized protein meets, or exceeds, the essential amino acids requirements of the animals during their growth phase. Histidine will be the limiting amino acid for this product.

On the other hand, the product after the second hydrolysis (feathers), the values for threonine, cysteine+methionine, tryptophan, and especially lysine and histidine are lower than the requirements making this a poor product for monogastric animal nutrition. However, it is suitable for ruminants.

Experiment 3.

Calcium Recovery and Recycle

The use of calcium hydroxide as the alkaline material produces a relatively high calcium concentration in the centrifuged liquid solution. Because some calcium salts have low solubility, calcium can be recovered by precipitating it as calcium carbonate, calcium bicarbonate, or calcium sulfate (gypsum).

Calcium carbonate is preferred because of its low solubility (0.0093 g/L, solubility product for $CaCO_3$ is $8.7 \times 10^{-9}$). In contrast, the solubility of $CaSO_4$ is 1.06 g/L, with a solubility product of $6 \times 10^{-5}$. Also, it is easier to regenerate $Ca(OH)_2$ from calcium carbonate than from calcium sulfate. Because $CaSO_4$ is a more soluble material and gypsum is more difficult to recycle, the use of $CaCO_3$ as the precipitate is a more efficient process.

When $CO_2$ is bubbled into the centrifuged solution, carbonic acid ($H_2CO_3$) is formed. The carbonic acid is a weak diprotic acid with $pKa_1=6.37$ and $pKa_2=10.25$. An equilibrium between $H_2CO_3$, $HCO_3^-$, and $CO_3^{2-}$ is generated and the fraction of each component in the mixture is a function of pH. Because $Ca(HCO_3)_2$ is water-soluble (166 g/L of water, solubility product 1.08), the precipitation efficiency of the process is also a function of pH.

To measure and study calcium recovery by $CO_2$ bubbling; centrifuged liquid products from the hydrolysis process of chicken feathers and offal were collected in plastic bottles and kept at 4° C. for later use. A known volume of the centrifuged liquid material (400 mL) was placed into an Erlenmeyer flask with a magnetic stirring bar (constant stirring), and $CO_2$ was bubbled from a pressurized container. As pH decreased, liquid samples (~10 mL) were collected and centrifuged. Total nitrogen and calcium content were measured in the clarified liquid. Samples with different initial pH were used to study how this parameter affects precipitation efficiency.

Figure 36:
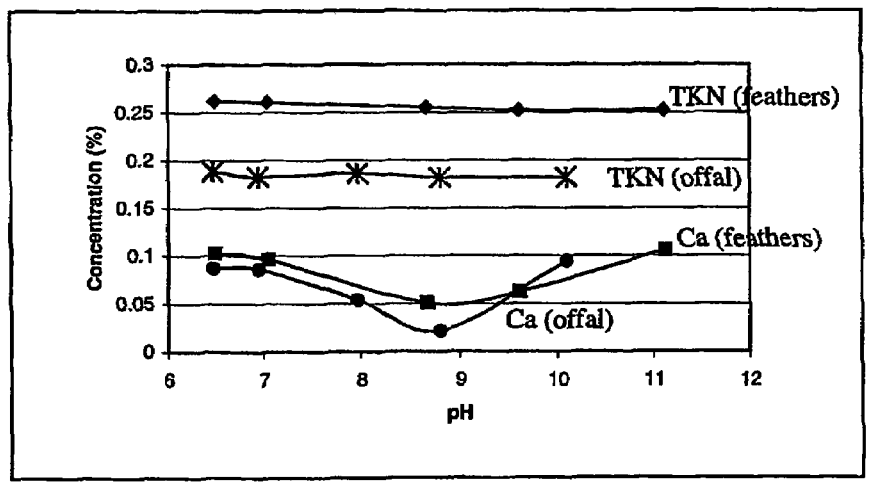
FIG. 36 is a graph illustrating calcium concentration as a function of pH during precipitation through carbon dioxide bubbling (high initial pH).

FIG. 36 shows the calcium and total nitrogen content as a function of pH for two different samples: one from chicken offal hydrolysis (C1) and the other from the chicken feathers hydrolysis (C2). In both cases, TKN concentration remains constant, implying that no nitrogen is lost during the precipitation of calcium.

FIG. 36 also shows that calcium concentration decreases to a minimum at pH~9 (calcium recovery between 50 and 70%), and increases at lower pHs. The increase in calcium concentration is expected because of the high solubility of calcium bicarbonate and the conversion of carbonate to bicarbonate and carbonic acid at low pH (8 and lower). The initial pH for the centrifuged liquid shown in FIG. 36 is relatively high (10.2 and 11.1 respectively); in both cases the equilibrium between the carbonic species is in a zone with relatively high carbonate concentration ($pKa_2$=10.25).

Figure 37:
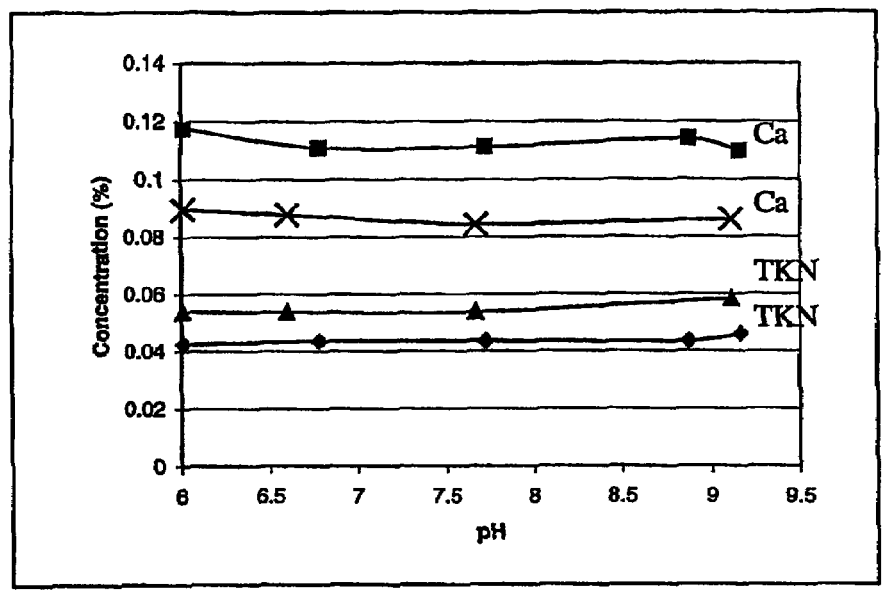
FIG. 37 is a graph illustrating calcium concentration as a function of pH during precipitation with carbon dioxide bubbling (lower initial pH).

FIG. 37 on the other hand, shows the calcium and total nitrogen content of samples with a relatively low initial pH (~9.2). Because the samples collected were well inside the equilibrium zone between carbonic acid and bicarbonate, no calcium could be recovered as a precipitate (calcium bicarbonate solubility).

Experiment 4

Preservation of Chicken Waste Under Alkaline Conditions

The chicken offal and feathers described previously in this example were used as raw materials for another set of experiments. Experiments were performed in 1-L Erlenmeyer flasks at ambient temperature and with no mixing; to avoid unpleasant odors, flasks were placed inside the hood. Calcium hydroxide loading (g $Ca(OH)_2$/g dry offal+feathers) was varied, to determine the lime required to preserve this waste material mixture. Generation of strong bad odors (fermentation products) is considered as the end-point of the study.

Duplicate experiments were run under the same conditions. Samples were taken from the reactor at different times and were centrifuged to separate the liquid phase from the solid material. Total nitrogen content and pH were measured in the centrifuged liquid samples.

To determine the lime required for preservation of the chicken waste mixture and to study protein solubilization of the waste material, several experiments were run with different lime loadings, at ambient temperature, and utilizing no mixing. The experimental conditions studied and variables measured are summarized in Table 86.

TABLE 86

Experimental conditions during study of preservation of chicken feathers and offal mixture

|  | Exp. G1 | Exp. G2 | Exp. H1 | Exp. H2 | Exp. I1 | Exp. I2 |
|---|---|---|---|---|---|---|
| Temperature (° C.) | 25 | 25 | 25 | 25 | 25 | 25 |
| Mass of $Ca(OH)_2$ (g) | 3.3 | 3.3 | 6.6 | 6.6 | 9.9 | 9.9 |
| Mass of offal (g) | 91.3 | 91.3 | 91.3 | 91.3 | 91.3 | 91.3 |
| Mass of feathers (g) | 36.5 | 36.5 | 36.5 | 36.5 | 36.5 | 36.5 |
| Volume of water (ml) | 800 | 800 | 800 | 800 | 800 | 800 |
| $Ca(OH)_2$ (g/g dry matter) | 0.052 | 0.052 | 0.103 | 0.103 | 0.155 | 0.155 |
| Dry matter (g/L) | 80.02 | 80.02 | 80.02 | 80.02 | 80.02 | 80.02 |
| Dry Offal (g/L) | 38.05 | 38.05 | 38.05 | 38.05 | 38.05 | 38.05 |
| Total TKN (g) | 6.79 | 6.79 | 6.79 | 6.79 | 6.79 | 6.79 |
| Total TKN (%) | 10.60 | 10.60 | 10.60 | 10.60 | 10.60 | 10.60 |

Table 87 shows the pH variation as a function of time while Table 88 shows the total nitrogen content of the centrifuged liquid.

TABLE 87 pH as a function of time during the preservation study of chicken offal and feathers mixture

| time (d) | Exp. G1 | Exp. G2 | Exp. H1 | Exp. H2 | Exp. I1 | Exp. I2 |
|---|---|---|---|---|---|---|
| 0 | 9.01 | 9.12 | 12.1 | 12.14 | 12.1 | 12.15 |
| 1 | — | — | 11.52 | 11.56 | 12.14 | 12.17 |
| 2 | — | — | 11.16 | 11.25 | 12.08 | 12.14 |
| 4 | — | — | 10.82 | 11.03 | 12.03 | 12.06 |
| 7 | — | — | 10.65 | 10.85 | 12.05 | 12.06 |
| 11 | — | — | 9.05 | 10.1 | 12.06 | 12.09 |
| 14 | — | — | — | — | 12.06 | 12.1 |
| 17 | — | — | — | — | 12.04 | 12.07 |

TABLE 88

Total Kjeldhal nitrogen content as a function of time during the preservation study of chicken offal and feathers mixture

| time (d) | Exp. G1 | Exp. G2 | Exp. H1 | Exp. H2 | Exp. I1 | Exp. I2 |
|---|---|---|---|---|---|---|
| 0 | 0.1438 | 0.1427 | 0.1002 | 0.1103 | 0.0924 | 0.0991 |
| 1 | — | — | 0.1248 | 0.1314 | 0.1325 | 0.1381 |
| 2 | — | — | 0.1337 | 0.1337 | 0.1460 | 0.1472 |
| 4 | — | — | 0.1348 | 0.1337 | 0.1596 | 0.1630 |
| 7 | — | — | 0.1371 | 0.1416 | 0.1835 | 0.1824 |
| 11 | — | — | 0.1472 | 0.1427 | 0.2099 | 0.2020 |
| 14 | — | — | — | — | 0.2239 | 0.2251 |
| 17 | — | — | — | — | 0.2297 | 0.2297 |

TKN in g nitrogen/100 g liquid sample.

The protein hydrolysis conversions were estimated and are given in Table 89 and Table 90. Table 89 considers the conversion with respect to the offal nitrogen content whereas Table 90 gives the conversion with respect to the initial TKN of the mixture. At the conditions studied, the highest conversion of nitrogen in the solid phase to the liquid phase was ~30%.

TABLE 89

Percent conversion in the liquid phase with respect to offal as a function of time (preservation experiment)

| time (d) | Exp. G1 | Exp. G2 | Exp. H1 | Exp. H2 | Exp. I1 | Exp. I2 |
|---|---|---|---|---|---|---|
| 0 | 75.5692 | 74.9911 | 52.6567 | 57.9644 | 48.5577 | 52.0786 |
| 1 | — | — | 65.5844 | 69.0528 | 69.6309 | 72.5738 |
| 2 | — | — | 70.2615 | 70.2615 | 76.7253 | 77.3560 |
| 4 | — | — | 70.8396 | 70.2615 | 83.8724 | 85.6591 |
| 7 | — | — | 72.0482 | 74.4131 | 96.4322 | 95.8541 |
| 11 | — | — | 77.3560 | 74.9911 | 110.3058 | 106.1542 |
| 14 | — | — | — | — | 117.6630 | 118.2937 |
| 17 | — | — | — | — | 120.7110 | 120.7110 |

TABLE 90

Percent conversion in the liquid phase with respect to total nitrogen as a function of time (preservation experiment)

| time (d) | Exp. G1 | Exp. G2 | Exp. H1 | Exp. H2 | Exp. I1 | Exp. I2 |
|---|---|---|---|---|---|---|
| 0 | 18.3018 | 18.1618 | 12.7527 | 14.0382 | 11.7600 | 12.6127 |
| 1 | — | — | 15.8836 | 16.7236 | 16.8636 | 17.5764 |
| 2 | — | — | 17.0164 | 17.0164 | 18.5818 | 18.7345 |
| 4 | — | — | 17.1564 | 17.0164 | 20.3127 | 20.7454 |
| 7 | — | — | 17.4491 | 18.0218 | 23.3545 | 23.2145 |
| 11 | — | — | 18.7345 | 18.1618 | 26.7145 | 25.7091 |
| 14 | — | — | — | — | 28.4963 | 28.6491 |
| 17 | — | — | — | — | 29.2345 | 29.2345 |

In Table 89, values higher than 100% imply the solubilization of chicken feather protein for the long-term reservation study. Also, a comparison between Experiments H and I correlate a high protein hydrolysis to a high pH. The reduction of pH during the hydrolysis process (Table 87) is related to the generation of new free amino acid values close to 9 were measured the day previous to strong odor generation.

Monitoring pH during the preservation of chicken waste mixture is a viable alternative for keeping a stable (non-fermentative) solution. Based on the results obtained, a pH value of 10.5 could be used as the lower limit for the addition of extra lime to avoid bacterial growth.

Lime is a relatively water insoluble base, and because of this low solubility, it generates mild-alkaline conditions (pH~12) in the solid-liquid mixture. The relative low pH reduces the possibility of unwanted degradation reactions, when compared to strong bases (e.g., sodium hydroxide). Lime also promotes the digestion of protein and solubilization into the liquid phase (Table 90), while the chicken waste mixture is preserved.

Chicken offal and feathers can be used to obtain an amino acid-rich product by treating with $Ca(OH)_2$ at temperatures less than 100° C. A simple non-pressurizing vessel can be used for the above process due to the low temperature requirements.

A chicken feather/offal mixture can be used to obtain two amino acid-rich products, one which is well balanced (offal) and a second which is deficient in some amino acids but high in protein and mineral content.

For the first lime treatment of the mixture—runs at 50-100° C.—the spectrum of essential amino acids obtained from the experiments meets or exceeds the requirements for many domestic animals during their growth period. Thus, the amino acid-rich solid product obtained by lime treating chicken offal could serve as a protein supplement for these animals.

For the second lime treatment of the mixture—runs at 75-100° C.—the spectrum of essential amino acids obtained from the experiments is deficient in several amino acids. Thus, the amino acid-rich solid product obtained by the second lime treatment of the chicken feathers/offal mixture could serve as a nitrogen and mineral source for ruminant animals.

Precipitation of calcium carbonate by bubbling $CO_2$ into the centrifuged liquid product gives a calcium recovery between 50 and 70%. A high initial pH is recommended (>10), so that calcium carbonate and not calcium bicarbonate is formed during the process; while a final pH~8.8-9.0 ensures a high calcium recovery for lime regeneration. Because $CaSO_4$ is a more soluble material and gypsum is more difficult to recycle, the use of $CaCO_3$ as the precipitate is a more efficient process. Finally, lime solutions hydrolyzed and preserved chicken processing waste, including the keratinous material in chicken feathers. The absence of putrefactive odors, the continuous protein hydrolysis into the liquid phase, and the possibility of continuous monitoring of pH during the conservation of the chicken waste mixture, make the process a feasible alternative for keeping a stable (non-fermentative) solution and preserve carcasses during on-farm storage.

Example 6

Protein Solubilization in Cow Hair

According to the USDA, 188 lbs. of red meat and poultry are consumed per capita each year in the USA, from which ~116 lbs. are from beef and pork. Animal slaughter generates large amounts of waste, and animal hair represents between 3 and 7% of the total weight. There is a need and a desire to make better use of waste residues, and to turn them into useful products.

Wet cow hair was obtained from Terrabon Company and then air-dried. To characterize the starting material, the moisture content, the total nitrogen (estimate of the protein fraction), and the amino acid content were determined.

Air-dried hair is used as the starting material for these experiments. Its dry matter content, chemical composition, and amino acid balance are given in Table 91, Table 92, and Table 93, respectively.

TABLE 91

Dry matter content of air-dried cow hair

| Sample | Humid Solid (q) | Dry Solid (g) | Dry matter (%) |
|---|---|---|---|
| 1 | 4.0883 | 3.8350 | 93.80 |
| 2 | 3.7447 | 3.5163 | 93.90 |
|  |  | Average | 93.85 |

TABLE 92

Protein and mineral content of air-dried cow hair

| Sample | TKN (%) | P (%) | K (%) | Ca (%) | Mg (%) | Na (ppm) | Zn (ppm) | Fe (ppm) | Cu (ppm) | Mn (ppm) |
|---|---|---|---|---|---|---|---|---|---|---|
| Hair | 14.73 | 0.0508 | 0.0197 | 0.1658 | 0.029 | 5244 | 58 | 185 | 50 | 37 |

TABLE 93

Amino acid composition of air-dried cow hair

| Amino acid | Measured | Literature | Amino acid | Measured | Literature |
|---|---|---|---|---|---|
| ASP | 6.63 | 3.0 | TYR | 2.44 | 3.4 |
| GLU | 14.47 | 12.2 | VAL | 6.80 | 5.5 |
| SER | 8.91 | 7.2 | MET | 0.71 | 0.6 |
| HIS | 1.29 | 0.7 | PHE | 3.09 | 3.0 |
| GLY | 5.52 | 10.8 | ILE | 4.20 | 4.4 |
| THR | 7.48 | 6.6 | LEU | 9.77 | 7.7 |
| ALA | 4.50 | 1.0 | LYS | 5.53 | 2.1 |
| CYS | ND | 13.9 | TRP | ND | 1.4 |
| ARG | 10.98 | 7.7 | PRO | 7.68 | 8.5 |

ND: Not determined
Values in g AA/100 g total amino acids.

The starting material contains a relatively well-balanced amino acid content, with low levels of histidine, methionine, tyrosine, and phenylalanine. The ash content is very low (~1%) and the crude protein content is high (~92.1%). The starting moisture content is 6.15%.

Experiment 1

Hair Concentration Effect

To determine the effect of the initial hair concentration in the solubilization of protein, experiments were run at different concentrations keeping the temperature and lime loading constant (100° C. and 0.10 g lime/g air-dried hair, respectively). The experimental conditions studied and variables measured are summarized in Table 94.

TABLE 94

Experimental conditions and variables measured for determining the effect of initial hair concentration in protein solubilization of cow hair

| | Hair concentration (g hair/L) | |
|---|---|---|
| | 40 | 60 |
| Mass of hair (g) | 34 | 51 |
| Volume of water (mL) | 850 | 850 |
| Mass of lime (g) | 3.4 | 5.1 |
| Temperature (° C.) | 100 | 100 |
| Initial temperature (° C.) | 101.4 | 87.1 |
| pH final | 9.2 | 9.8 |
| Residual solid (g) | 28.8 | 44.9 |
| Dissolved solids in 100 mL (g) | 1.18 | 1.92 |
| Protein in 100 mL (g) | 0.81 | 1.04 |

Table 95 shows the total nitrogen content in the centrifuged liquid samples as a function of time for the different hair concentrations. On the basis of the average TKN for air-dried hair (14.73%), the protein hydrolysis conversions are estimated and are given in Table 96.

TABLE 95

Total Kjeldhal nitrogen content in the centrifuged liquid phase as a function of time for Experiment 1 (cow hair)

| | Air-dried hair concentration | |
|---|---|---|
| Time (h) | 40 g/L | 60 g/L |
| 0 | 0.0160 | 0.0327 |
| 0.5 | 0.0185 | 0.0497 |
| 1 | 0.0435 | 0.0699 |
| 2 | 0.0718 | 0.1000 |
| 3 | 0.0754 | 0.1194 |
| 4 | 0.0868 | 0.1368 |
| 6 | 0.1088 | 0.1629 |
| 8 | 0.1298 | 0.1662 |

TKN in g nitrogen/100 g liquid sample

TABLE 96

Percentage conversion of the total TKN to soluble TKN for Experiment 1 (cow hair)

| | Air-dried hair concentration | |
|---|---|---|
| Time (h) | 40 g/L | 60 g/L |
| 0 | 2.72 | 3.70 |
| 0.5 | 3.14 | 5.62 |
| 1 | 7.38 | 7.91 |
| 2 | 12.19 | 11.31 |
| 3 | 12.80 | 13.51 |
| 4 | 14.73 | 15.48 |
| 6 | 18.47 | 18.43 |
| 8 | 22.03 | 18.81 |

Figure 38:
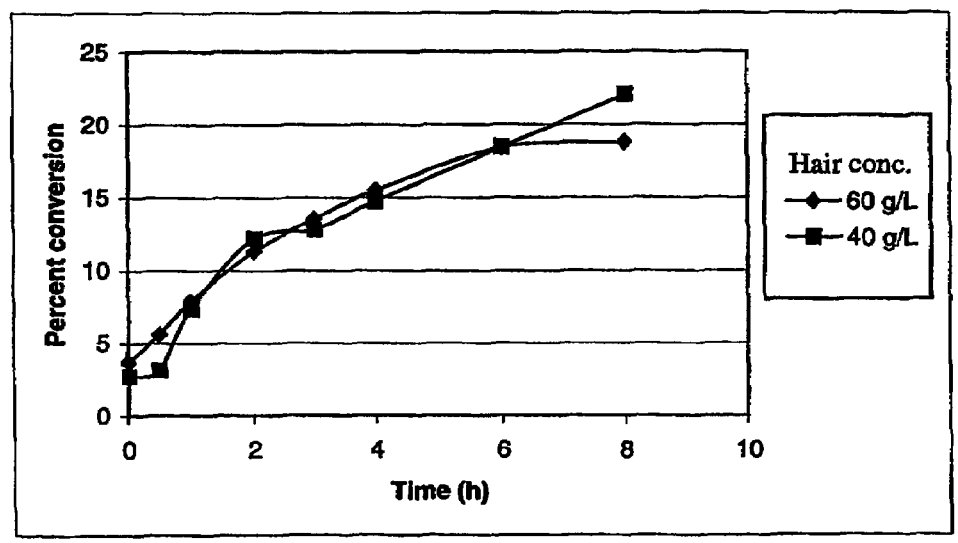
FIG. 38 is a graph illustrating the effect of air-dried hair concentration on protein solubilization.

FIG. 38 presents the protein solubilization (percentage conversion) as a function of time for the different hair concentrations studied. It shows that hair concentration has no important effect on protein hydrolysis (conversion) and that higher lime loadings or a longer treatment period are required to obtain conversions on the order of 70%, which can be obtained with chicken feathers, another keratin material.

As Table 94 shows, the dissolved solids are higher for the higher hair concentration, as expected. The final pH for both cases is lower than the initial 12.0, implying that lime was consumed during the hydrolysis and that lime was not present as a solid in the final mixture.

Experiment 2

Lime Loading Effect

To determine the effect of lime loading on protein solubilization of air-dried hair, experiments were run at different lime/hair ratios keeping the temperature and hair concentration constant (100° C. and 40 g air-dried hair/L, respectively). The experimental conditions studied and variables measured are summarized in Table 97.

TABLE 97

Experimental conditions and variables measured to determine the lime loading effect in protein solubilization of cow hair

| | Lime loading (g lime/g hair) | | | |
|---|---|---|---|---|
| | 0.10 | 0.20 | 0.25 | 0.35 |
| Mass of hair (g) | 34 | 34 | 34 | 34 |
| Volume of water (mL) | 850 | 850 | 850 | 850 |
| Mass of lime (g) | 3.4 | 6.8 | 8.5 | 11.9 |
| Temperature (° C.) | 100 | 100 | 100 | 100 |
| Initial temperature (° C.) | 101.4 | 102.3 | 75.6 | 90.2 |
| pH final | 9.2 | 10.3 | 11.4 | 11.2 |
| Residual solid (g) | 28.8 | 17.44(*) | 22.6 | 22.9 |
| Dissolved solids in 100 mL (g) | 1.18 | 2.92(*) | 2.96 | 2.99 |
| Protein in 100 mL (g) | 0.81 | 1.77 | 2.18 | 2.40 |

(*)Measured after 48 h and not at 8 h as the other three conditions.

Table 98 shows the total nitrogen content in the centrifuged liquid samples as a function of time for the different lime loadings. On the basis of the average TKN for air-dried hair (14.73%), the protein hydrolysis conversions are estimated and given in Table 99.

TABLE 98

Total Kjeldhal nitrogen content in the centrifuged liquid phase as a function of time for Experiment 2 (cow hair)

| | Lime loading | | | |
|---|---|---|---|---|
| Time (min) | 0.10 g/g | 0.20 g/g | 0.25 g/g | 0.35 g/g |
| 0 | 0.0160 | 0.0144 | 0.0241 | 0.0133 |
| 0.5 | 0.0185 | — | 0.0454 | 0.0637 |
| 1 | 0.0435 | 0.0845 | 0.0922 | 0.0822 |
| 2 | 0.0718 | 0.1425 | 0.1350 | 0.1438 |
| 3 | 0.0754 | — | 0.1549 | 0.1792 |
| 4 | 0.0868 | 0.2145 | 0.1951 | 0.2023 |
| 6 | 0.1088 | — | 0.2699 | 0.2999 |
| 8 | 0.1298 | 0.2832 | 0.3487 | 0.3837 |

TKN in g nitrogen/100 g liquid sample.

TABLE 99

Percentage conversion of the total TKN to soluble TKN for Experiment 2 (cow hair)

| | Lime loading | | | |
|---|---|---|---|---|
| Time (min) | 0.10 g/g | 0.20 g/g | 0.25 g/g | 0.35 g/g |
| 0 | 2.72 | 2.44 | 4.09 | 2.26 |
| 0.5 | 3.14 | — | 7.71 | 10.81 |
| 1 | 7.38 | 14.34 | 15.65 | 13.95 |
| 2 | 12.19 | 24.19 | 22.91 | 24.41 |
| 3 | 12.80 | — | 26.29 | 30.41 |
| 4 | 14.73 | 36.41 | 33.11 | 34.33 |
| 6 | 18.47 | — | 45.81 | 50.90 |
| 8 | 22.03 | 48.07 | 59.18 | 65.12 |

Figure 39:
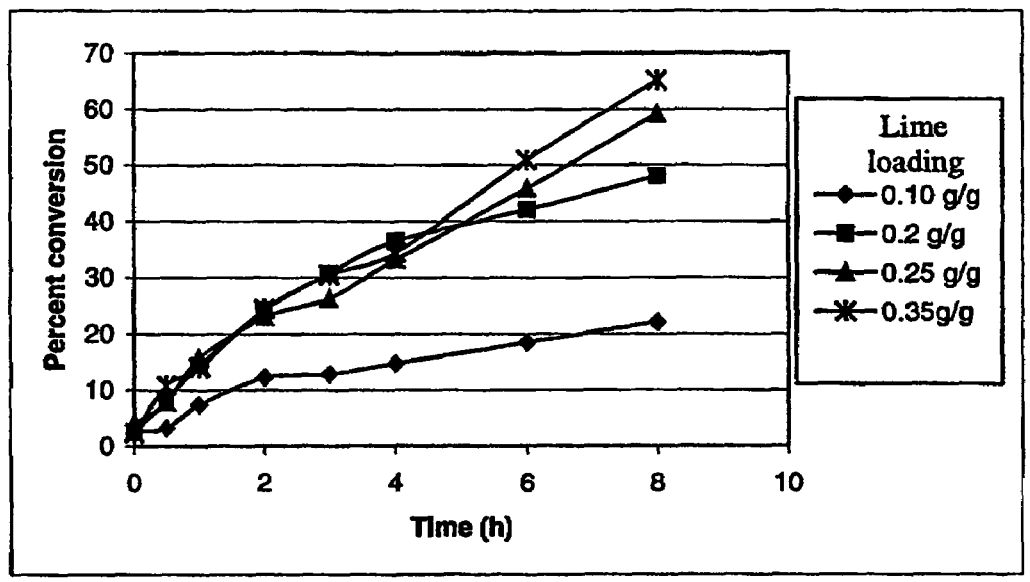
FIG. 39 is a graph illustrating lime loading effect on protein solubilization of air-dried hair.

FIG. 39 presents the protein solubilized (percentage conversion) as a function of time for the different lime loadings studied. It shows that the conversion is similar for all lime loadings, except for 0.1 g lime/g air-dried hair. FIG. 38 shows that the conversions differ more at longer times and that the reaction does not slow down at 8 h for any of the lime loading studied. Hence, a longer treatment period may increase the conversion and the minimum lime loading required for the process to be efficient.

As Table 97 shows, the dissolved solids are higher for the higher lime loadings as expected (higher calcium salts in solutions and higher conversion). The final pH increases the lime loading increases, and is lower than 12.0 in all cases, again implying the consumption of lime during the hydrolysis and that the final OH-concentration (pH) can be related back to the efficiency of the treatment.

The behavior shown in FIG. 39 can be related to the requirement for the hydroxyl group as a catalyst for the hydrolysis reaction. The low solubility of lime maintains a "constant" lime concentration in all treatments (0.2 to 0.35 g lime/g air-dried hair), but its consumption during the process makes the lower lime loading reaction slow down or level off faster.

Experiment 3

Effect of Longer Term Treatment

To establish the effect of a long-term treatment in the solubilization of protein, experiments were run at two different conditions: 100° C., 0.2 g lime/g air-dried hair with 40 g air-dried hair/L; and 100° C., 0.35 g lime/g air-dried hair with 40 g air-dried hair/L, respectively. The experimental conditions studied and variables measured are summarized in Table 100.

TABLE 100

Experimental conditions and variables measured for determining the effect of a longer treatment period in protein solubilization of cow hair

| | Lime loading (g lime/g air-dried hair) | |
|---|---|---|
| | 0.2 | 0.35 |
| Mass of hair (g) | 34 | 34 |
| Volume of water (mL) | 850 | 850 |
| Mass of lime (g) | 6.8 | 11.9 |
| Temperature (° C.) | 100 | 100 |
| pH final | 10.3 | 11.99 |
| Residual solid (g) | 17.44 | 10.74 |
| Dissolved solids in 100 mL (g) | 2.92 | 4.01 |
| Protein in 100 mL (g) at 48 h | 2.25 | 2.63 |

Table 101 shows the total nitrogen content in the centrifuged liquid samples as a function of time for the different lime loadings. On the basis of the average TKN for air-dried hair (14.73%), the protein hydrolysis conversions are estimated and given in Table 102.

TABLE 101

Total Kjeldhal nitrogen content in the centrifuged liquid phase as a function of time for Experiment 3 (cow hair)

| | Lime loading | |
|---|---|---|
| Time (h) | 0.20 g/g | 0.35 g/g |
| 0 | 0.0144 | 0.0133 |
| 1 | 0.0845 | — |
| 2 | 0.1425 | — |
| 4 | 0.2145 | 0.2088 |
| 8 | 0.2832 | 0.2832 |
| 12 | 0.3089 | — |
| 24 | 0.3319 | 0.3988 |

TABLE 101-continued

Total Kjeldhal nitrogen content in the centrifuged liquid phase as a function of time for Experiment 3 (cow hair)

| | Lime loading | |
|---|---|---|
| Time (h) | 0.20 g/g | 0.35 g/g |
| 36 | 0.3617 | 0.4265 |
| 48 | 0.3597 | 0.4210 |

TKN in g nitrogen/100 g liquid sample.

TABLE 102

Percentage conversion of total TKN to soluble TKN for Experiment 3 (cow hair)

| | Lime loading | |
|---|---|---|
| Time (h) | 0.20 g/g | 0.35 g/g |
| 0 | 2.44 | 2.26 |
| 1 | 14.34 | — |
| 2 | 24.19 | — |
| 4 | 36.41 | 35.44 |
| 8 | 48.07 | 48.07 |
| 12 | 52.43 | — |
| 24 | 56.33 | 67.68 |
| 36 | 61.39 | 72.39 |
| 48 | 61.05 | 71.45 |

Figure 40:
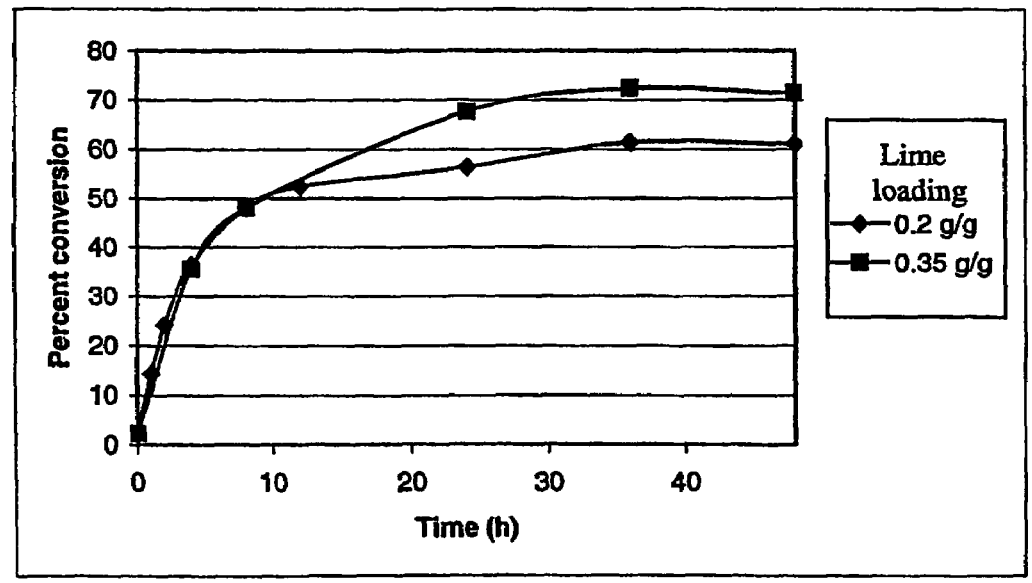
FIG. 40 is a graph illustrating lime loading effect on protein solubilization of air-dried hair in long-term treatments.

FIG. 40 presents the protein solubilization (percentage conversion) as a function of time for the two different conditions studied. It shows that the conversions differ for the longer time treatments and that the reaction reaches the highest conversion between 24 and 36 hours of treatment. The relation between lime availability and conversion is more perceptible in this long-term treatment study.

There is a very perceptible ammonia odor, starting at 24 hours, that suggests amino acid degradation at longer periods. One way to reduce this problem is to recover amino acids already hydrolyzed to the liquid phase with separation of residual solids for further alkaline hydrolysis in subsequent treatment steps.

Experiment 4

Ammonia Measurements During Alkaline Hydrolysis of Air-Dried Cow Hair (Amino Acid Degradation)

The effect of a long-term treatment in the solubilization of protein and the degradation of soluble amino acids was determined by ammonia measurements. The ammonia concentration was determined as a function of time for the two experimental conditions of Experiment 3 and for an additional run that used the centrifuged liquid of an experiment performed at 100° C., 0.2 g lime/g air-dried hair with 40 g air-dried hair/L for 5 hours. The experimental conditions studied and variables measured are summarized in Table 103.

TABLE 103

Experimental conditions and variables measured for determining the effect of a longer treatment period on amino acid degradation

| | Lime loading (g lime/g air-dried hair) | | |
|---|---|---|---|
| | 0.2 (Exp. A1) | 0.35 (Exp. A2) | 0.35 (Exp. A3) |
| Mass of hair (g) | 34 | 34 | ** |
| Volume of water (mL) | 850 | 850 | 850 |
| Mass of lime (g) | 6.8 | 11.9 | 8.5 |
| Temperature (° C.) | 100 | 100 | 100 |
| Initial temperature (° C.) | 102.3 | 98.8 | 96.6 |
| pH final | 10.3 | 11.99 | 12.08 |
| Residual solid (g) | 17.44 | 10.74 | 8.28 |
| Dissolved solids in 100 mL (g) | 2.92 | 4.01 | 2.50 |
| Protein in 100 mL (g) at 48 h | 2.25 | 2.63 | 1.41 |

** No solid material was used, only the centrifuged liquid from a previous experiment.

Figure 41:
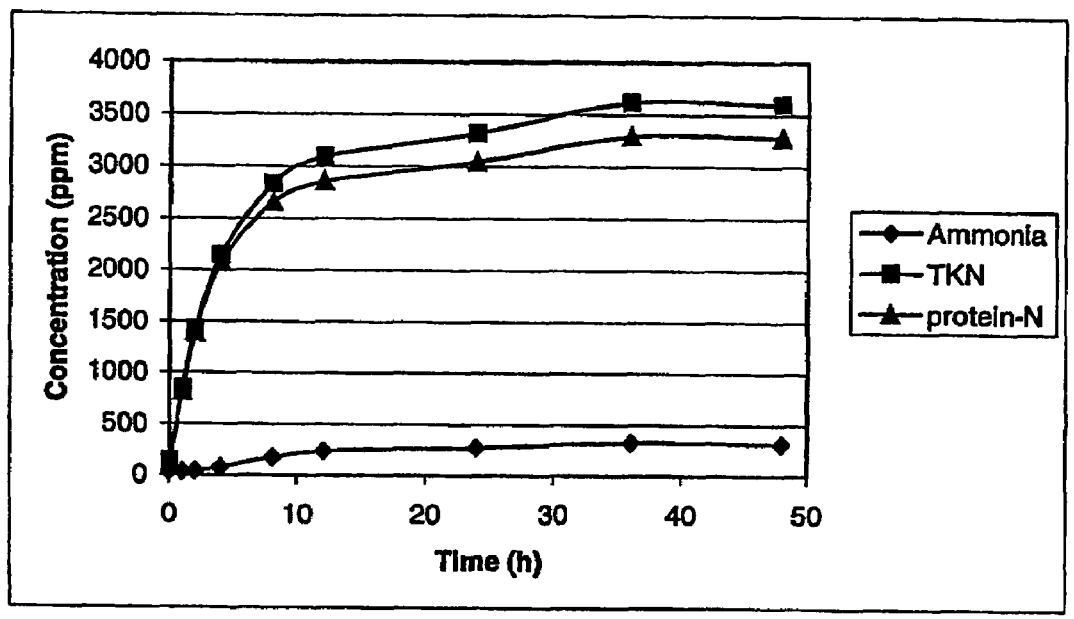
FIG. 41 is a graph illustrating ammonia, total Kjeldhal nitrogen, and estimated protein nitrogen concentration as a function of time in experiment A1.
Figure 42:
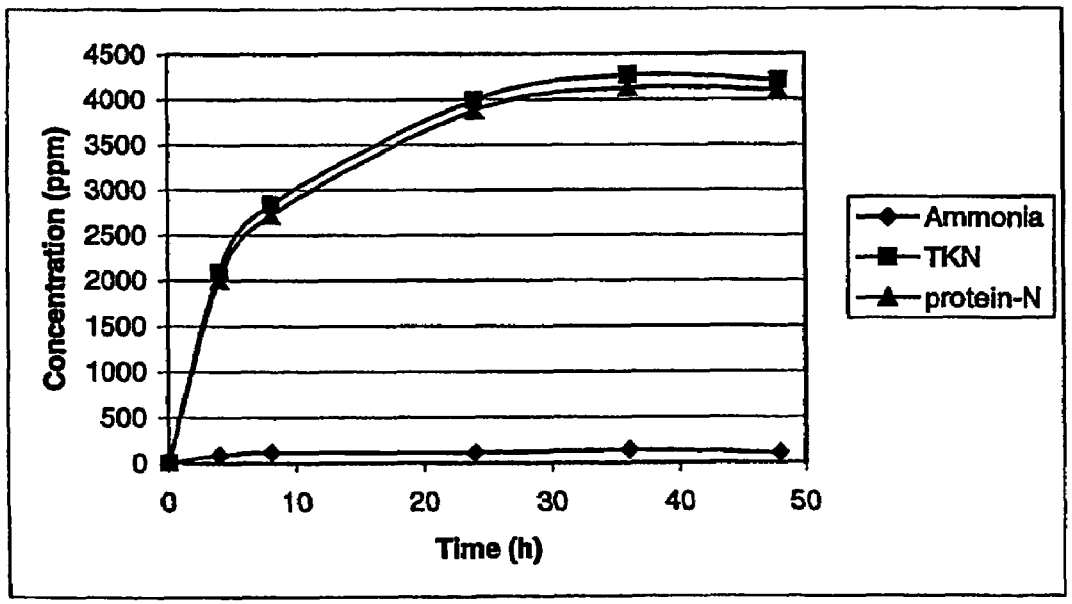
FIG. 42 is a graph illustrating ammonia, total Kjeldhal nitrogen, and estimated protein nitrogen concentration as a function of time in experiment A2.
Figure 43:
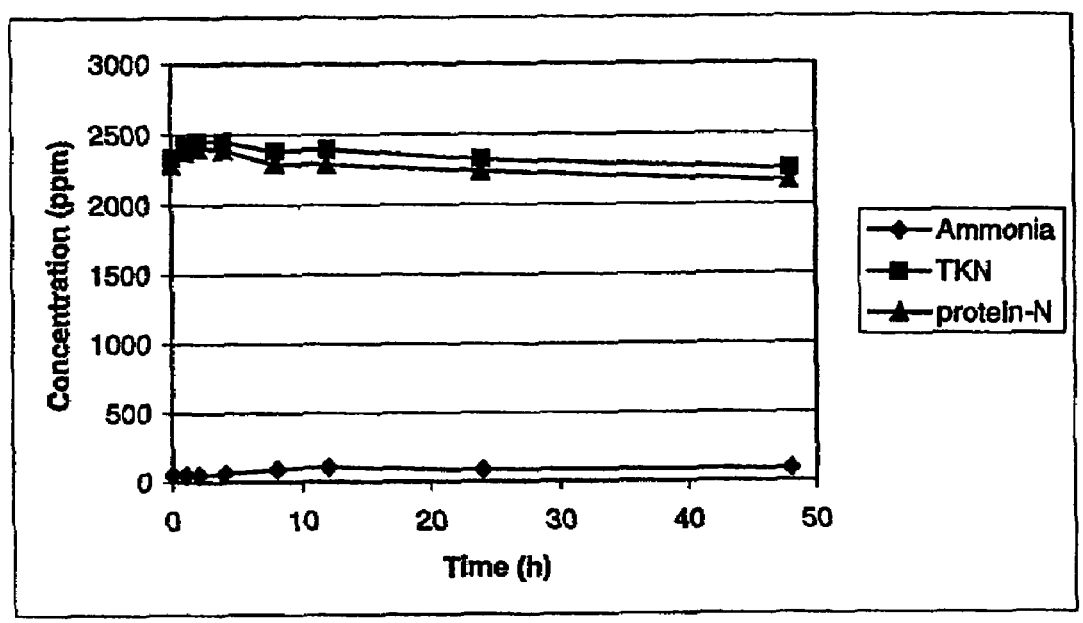
FIG. 43 is a graph illustrating ammonia, total Kjeldhal nitrogen, and estimated protein nitrogen concentration as a function of time in experiment A3.

Tables 104-106 and FIGS. 41-43 show the total nitrogen content and the free ammonia concentration in the centrifuged liquid samples as a function of time for the different experimental conditions.

TABLE 104

Total Kjeldhal nitrogen content, ammonia concentration and estimated protein nitrogen in the centrifuged liquid phase as a function of time for Experiment A1 (cow hair)

| Time (h) | [Ammonia] (ppm) | TKN (%) | TKN (ppm) | Protein-N (ppm) |
|---|---|---|---|---|
| 0 | 34 | 0.0144 | 144 | 110 |
| 1 | 33 | 0.0845 | 845 | 812 |
| 2 | 41 | 0.1425 | 1425 | 1384 |
| 4 | 76 | 0.2145 | 2145 | 2069 |
| 8 | 175 | 0.2832 | 2832 | 2657 |
| 12 | 236 | 0.3089 | 3089 | 2853 |
| 24 | 274 | 0.3319 | 3319 | 3045 |
| 36 | 327 | 0.3617 | 3617 | 3290 |
| 48 | 316 | 0.3597 | 3597 | 3281 |

TKN in g nitrogen/100 g liquid sample.

TABLE 105

Total Kjeldhal nitrogen content, ammonia concentration and estimated protein nitrogen in the centrifuged liquid phase as a function of time for Experiment A2 (cow hair)

| Time (h) | [Ammonia] (ppm) | TKN (%) | TKN (ppm) | Protein-N (ppm) |
|---|---|---|---|---|
| 0 | 0 | 0 | 0 | 0 |
| 4 | 85 | 0.2088 | 2088 | 2003 |
| 8 | 115 | 0.2832 | 2832 | 2717 |
| 24 | 111 | 0.3988 | 3988 | 3877 |
| 36 | 141 | 0.4265 | 4265 | 4124 |
| 48 | 110 | 0.4210 | 4210 | 4100 |

TKN in g nitrogen/100 g liquid sample.

TABLE 106

Total Kjeldhal nitrogen content, ammonia concentration and estimated protein nitrogen in the centrifuged liquid phase as a function of time for Experiment A3 (cow hair)

| Time (h) | [Ammonia] (ppm) | TKN (%) | TKN (ppm) | Protein-N (PPM) |
|---|---|---|---|---|
| 0 | 50 | 0.2332 | 2332 | 2282 |
| 1 | 50 | 0.2426 | 2426 | 2376 |

TABLE 106-continued

Total Kjeldhal nitrogen content, ammonia concentration and estimated protein nitrogen in the centrifuged liquid phase as a function of time for Experiment A3 (cow hair)

| Time (h) | [Ammonia] (ppm) | TKN (%) | TKN (ppm) | Protein-N (PPM) |
|---|---|---|---|---|
| 2 | 51 | 0.2449 | 2449 | 2398 |
| 4 | 60 | 0.2449 | 2449 | 2389 |
| 8 | 90 | 0.2382 | 2382 | 2292 |
| 12 | 106 | 0.2393 | 2393 | 2287 |
| 24 | 86 | 0.2326 | 2326 | 2240 |
| 48 | 87 | 0.2248 | 2248 | 2161 |

Ammonia concentration in the centrifuged liquid is determined by the Kjeldhal method but with no initial hydrolysis of the sample.
TKN in g nitrogen/100 g liquid sample.

FIGS. 41 and 42 show that the total protein-N concentration increases as a function of time until it reaches a maximum between 24 and 36 h of treatment. The free ammonia concentration also increases as a function of time, suggesting the degradation of amino acids. In Experiments A1 and A2, further hydrolysis of hair into the liquid exceeds amino acid degradation, giving a net improvement of protein-N until the 24-36 h period.

In Experiment A3 no solid hair was present, so there is no protein source other than previously solubilized protein. In this case, the reduction of protein-N occurred after 4 h and continued at 48 h, implying that there are several amino acids that are susceptible to degradation at the conditions studied.

Experiment 4A

Amino Acid Degradation Study

For Experiments A2 and A3, the amino acid composition of liquid samples was analyzed to determine the stability of individual amino acids in the protein hydrolyzate.

Two different amino acid analyses of lime-hydrolyzed cow-hair were performed:

1) Free amino acids in the centrifuged liquid. The analysis was made without extra HCL hydrolysis of the sample. No amino acids were destroyed by the analytical procedure, but soluble polypeptides are missing in the analysis.

2) Total amino acids in the centrifuged liquid.

HCL hydrolysis was performed before HPLC determination. Some amino acids (asparagine, glutamine, cysteine, and tryptophan) were destroyed by the acid and could not be measured.

Table 107 and Table 108 compare the total amino acids (HCL hydrolysis), the free amino acids, and the estimated amino acids using TKN values. These tables show that hair protein is hydrolyzed mainly to small soluble peptides instead of free amino acids (comparing the free amino acids with the total amino acids columns).

TABLE 107

Protein concentrations comparison for Experiment A2 (cow hair)

| Time (h) | TKN (%) | Protein (mg/L) | Free AA (mq/L) | Total AA (mg/L) |
|---|---|---|---|---|
| 4 | 0.2088 | 13050.0 | 330.4 | 4783.5 |
| 8 | 0.2832 | 17700.0 | 684.5 | 9300.4 |
| 24 | 0.3988 | 24925.0 | 1454.9 | 12208.4 |

TABLE 107-continued

Protein concentrations comparison for Experiment A2 (cow hair)

| Time (h) | TKN (%) | Protein (mg/L) | Free AA (mq/L) | Total AA (mg/L) |
|---|---|---|---|---|
| 36 | 0.4265 | 26656.3 | 1699.2 | 13680.1 |
| 48 | 0.4210 | 26312.5 | 1742.6 | 13989.6 |

TABLE 108

Protein concentrations comparison for Experiment A3 (cow hair)

| Time (h) | TKN (%) | Protein (mg/L) | Free AA (mg/L) | Total AA (mg/L) |
|---|---|---|---|---|
| 0 | 0.2332 | 14575.0 | 413.6 | 7373.0 |
| 1 | 0.2426 | 15162.5 | 816.6 | 9490.6 |
| 2 | 0.2449 | 15306.3 | 989.4 | 11075.4 |
| 4 | 0.2449 | 15306.3 | 1154.7 | 12040.4 |
| 8 | 0.2382 | 14887.5 | 1393.9 | 10549.1 |
| 12 | 0.2393 | 14956.3 | 1571.9 | 9988.4 |
| 24 | 0.2326 | 14537.5 | 2266.9 | 8464.8 |
| 48 | 0.2248 | 14050.0 | 2236.9 | 8782.3 |

Table 108 also shows an increase in the total amino acid concentration between 0 and 4 h. Because this experiment (A3) was performed only with centrifuged liquid (no solid hair), the increasing value can be explained by the presence of suspended polypeptides particles in solution that are further hydrolyzed in the liquid. Liquid was centrifuged at 3500 rpm in the solid separation, whereas 15000 rpm is used before HPLC analysis.

Table 108 shows a very good agreement between the estimated protein (TKN) and the total amino acids concentration at 4 h. At this time, there is relatively little amino acid degradation and a very high conversion of the "suspended material" in the liquid phase. In Table 107, the difference can be explained by the presence of this suspended material, which is not accounted for in the amino acid analysis.

Figure 44:
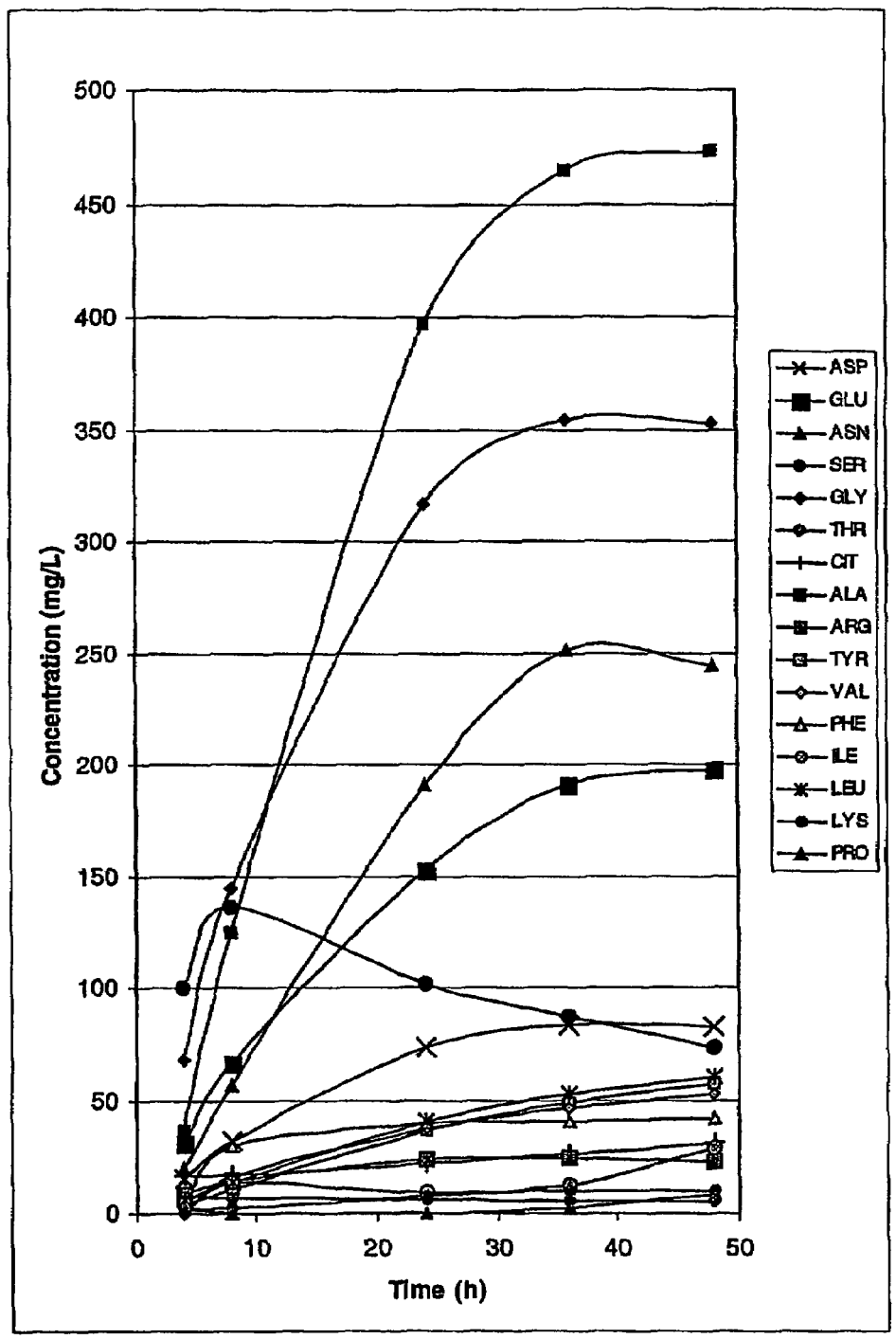
FIG. 44 is a graph illustrating free amino acid concentration as a function of time in experiment A2.
Figure 45:
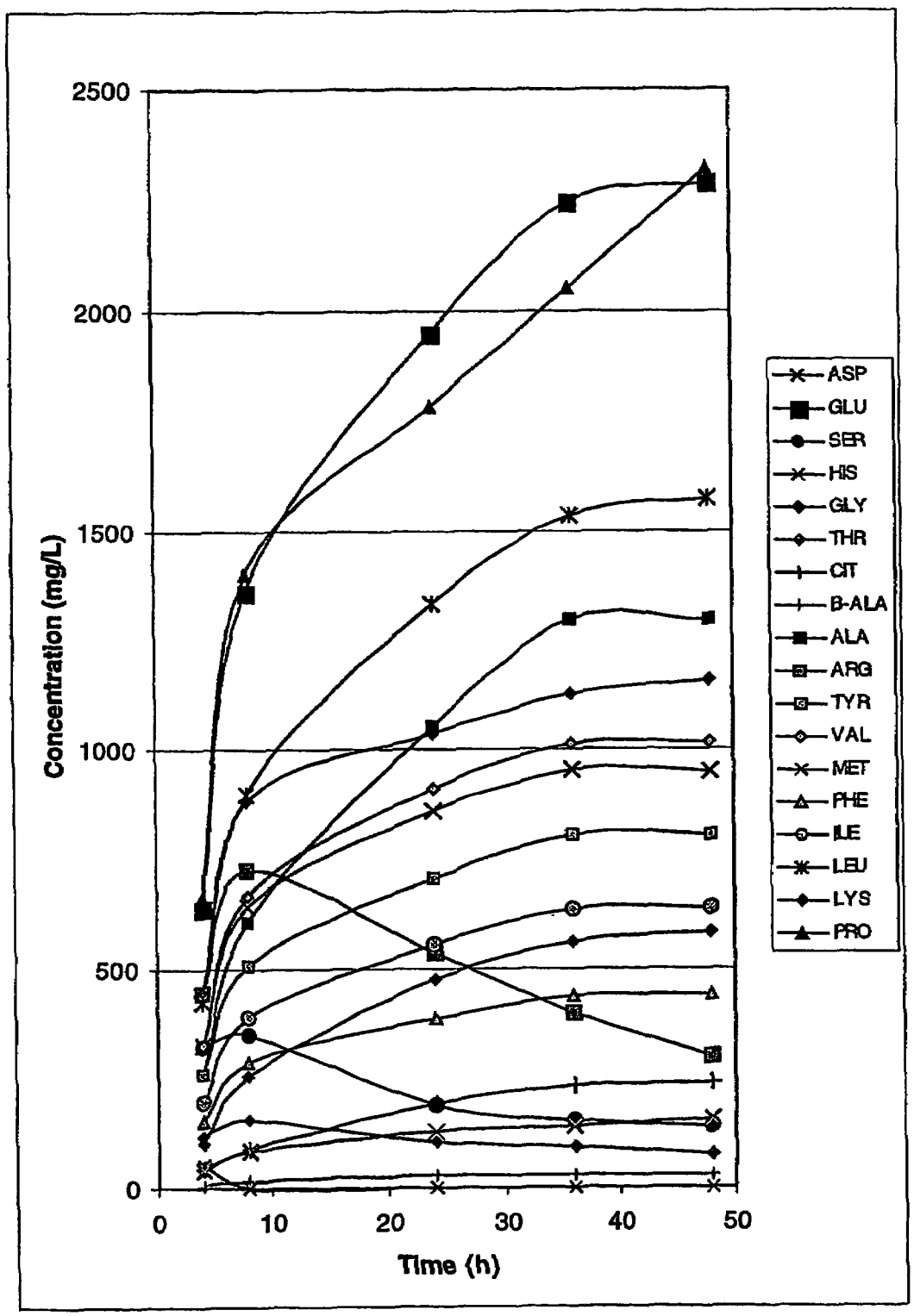
FIG. 45 is a graph illustrating total amino acid concentration as a function of time in experiment A2.

For Experiment A2, FIG. 44 shows the concentration of individual free amino acids present in the centrifuged liquid as a function of time, whereas FIG. 45 shows the total concentration of individual amino acids as a function of time. Histidine concentrations could not be measured or are underestimated because it eluted right before a very high concentration of glycine; hence, the peaks could not be separated.

FIG. 45 shows an increase in all amino acids concentration until 36 h, except for arginine, threonine, and serine. FIG. 44 shows a similar behavior, except that the concentrations are lower, especially for arginine and threonine. At 36 hours the amino acid concentrations level off (except for arginine, threonine, and serine), suggesting equilibrium between the solubilization and degradation processes.

Figure 46:
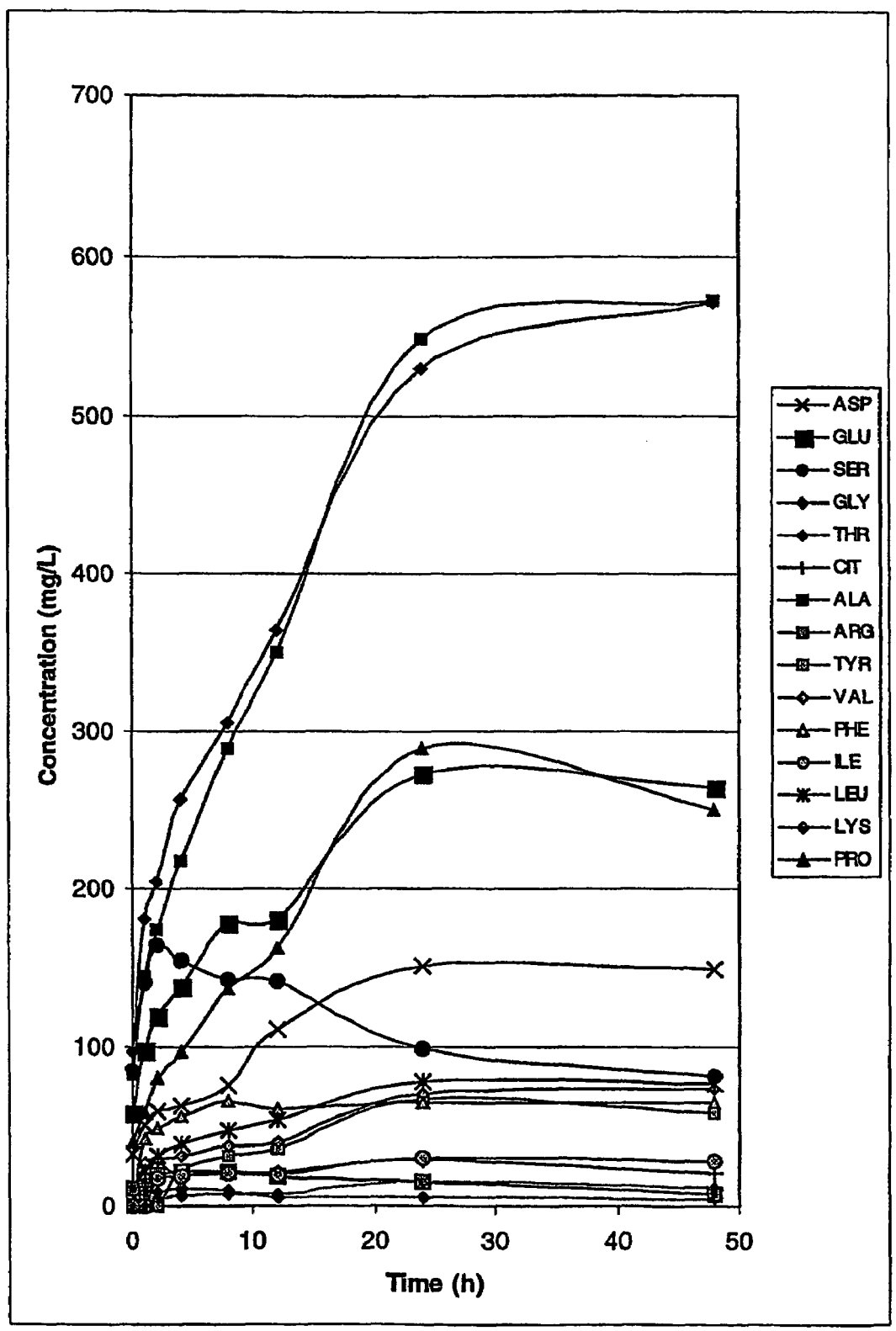
FIG. 46 is a graph illustrating free amino acid concentration as a function of time in experiment A3.

For Experiment A3 (no solid hair added, only centrifuged liquid), FIG. 45 shows the concentration of individual free amino acids present in the centrifuged liquid as a function of time, whereas FIG. 46 shows the total concentration of individual amino acids as a function of time.

In FIG. 46, the concentration of free amino acids increases until 24 h when it levels off. Again, the exceptions are arginine, threonine, and serine, with very low concentrations of the first two as free amino acids.

Figure 47:
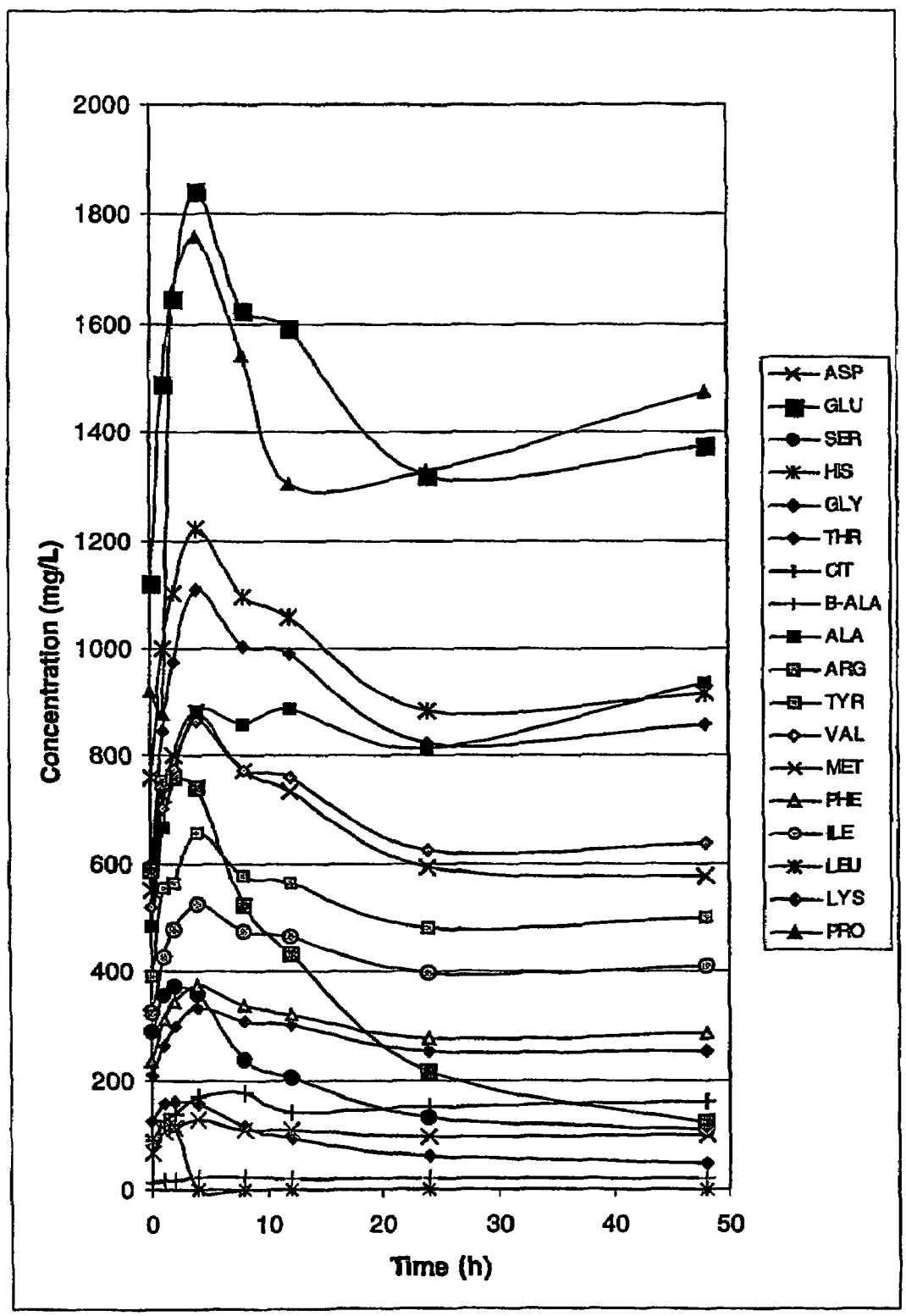
FIG. 47 is a graph illustrating total amino acid concentration as a function of time in experiment A3.

FIG. 47 shows an increase in all individual amino acids concentration between 0 and 4 h. This implies again the presence of suspended particles in the initial centrifuged liquid that are hydrolyzed to the liquid phase between 0 and 4 h. After this initial trend, the concentrations of all amino acids decline with time, suggesting the degradation of all amino acids under the condition studied for the long-term treatments. Arginine (16% of the concentration obtained at 4 h is present at 48 h), threonine (31%), and serine (31%) degrade more than the other amino acids.

Increasing concentrations of ornithine and citrulline, both not present in perceptible amounts in hair, suggest them as possible degradation products.

Table 109 shows the weight percentage of each amino acid as a function of time for Experiment A2. Similar contents are present for most of the amino acids with the exception of arginine, threonine, and serine. Some amino acid percentages Increase because of their higher resistance to degradation and the decrease of others.

TABLE 109

Individual amino acid present in Experiment A2 as a function of time compared to the initial material

| Amino Acid | Time (h) | | | | | Hair |
|---|---|---|---|---|---|---|
| | 4 | 8 | 24 | 36 | 48 | |
| ASP | 6.76 | 6.90 | 7.03 | 6.96 | 6.77 | 6.63 |
| GLU | 13.31 | 14.64 | 15.96 | 16.42 | 16.37 | 14.47 |
| SER | 6.68 | 3.76 | 1.53 | 1.11 | 1.00 | 8.91 |
| HIS | 1.11 | 0.00 | 0.00 | 0.00 | 0.00 | 1.29 |
| GLY | 9.33 | 9.48 | 8.50 | 8.25 | 8.29 | 5.52 |
| THR | 2.40 | 1.66 | 0.85 | 0.66 | 0.54 | 7.48 |
| CIT | 0.91 | 0.95 | 1.56 | 1.68 | 1.68 | 0.00 |
| ALA | 5.40 | 6.50 | 8.63 | 9.47 | 9.27 | 4.50 |
| ARG | 9.22 | 7.79 | 4.38 | 2.89 | 2.11 | 10.98 |
| TYR | 5.35 | 5.43 | 5.78 | 5.87 | 5.74 | 2.44 |
| VAL | 6.74 | 7.13 | 7.45 | 7.40 | 7.25 | 6.80 |
| MET | 0.80 | 0.90 | 1.05 | 1.00 | 1.09 | 0.71 |
| PHE | 3.17 | 3.05 | 3.13 | 3.17 | 3.15 | 3.09 |
| ILE | 4.04 | 4.19 | 4.52 | 4.62 | 4.55 | 4.20 |
| LEU | 8.81 | 9.66 | 10.92 | 11.21 | 11.25 | 9.77 |
| LYS | 2.09 | 2.71 | 3.89 | 4.08 | 4.14 | 5.53 |
| PRO | 13.77 | 15.07 | 14.60 | 15.02 | 16.60 | 7.68 |

Values in g AA/100 g total amino acids.

Experiment 5

Two-Step Treatment of Material

The amino acid degradation observed in the previous experiments affects the overall efficiency of the hydrolysis process. One way to tackle this problem is to separate the already-hydrolyzed protein with subsequent solubilization of protein (residual solids) in a series of treatment steps. In this experiment, two conditions were studied to determine the effect of a two-step process in the hydrolysis efficiency and the amino acid degradation of protein in air-dried hair. The experimental conditions studied and variables measured are summarized in Table 110.

TABLE 110

Experimental conditions and variables measured to determine the lime loading effect in protein solubilization (cow hair - two step treatment)

| | Experiment | | | |
|---|---|---|---|---|
| | Exp. C1 | Exp. C2 | Exp. D1 | Exp. D2 |
| Mass of hair (g) | 34 | 20 | 34 | 20 |
| Volume of water (mL) | 850 | 850 | 850 | 850 |
| Mass of lime (g) | 8.5 | 5 | 11.9 | 5 |
| Temperature (° C.) | 100 | 100 | 100 | 100 |

TABLE 110-continued

Experimental conditions and variables measured to determine the lime loading effect in protein solubilization (cow hair - two step treatment)

| | Experiment | | | |
|---|---|---|---|---|
| | Exp. C1 | Exp. C2 | Exp. D1 | Exp. D2 |
| Initial temperature (° C.) | 75.6 | 96.5 | 90.2 | 105 |
| pH final | 11.4 | 11.2 | 11.2 | 11.2 |
| Residual solid (g) at 8 h | 22.6 | 12.7 | 22.9 | 12.4 |
| Dissolved solids in 100 mL (g) | 2.96 | 1.15 | 2.99 | 1.17 |
| Protein in 100 mL (g) at 8 h | 1.80 | 0.91 | 1.78 | 0.86 |

Figure 48:
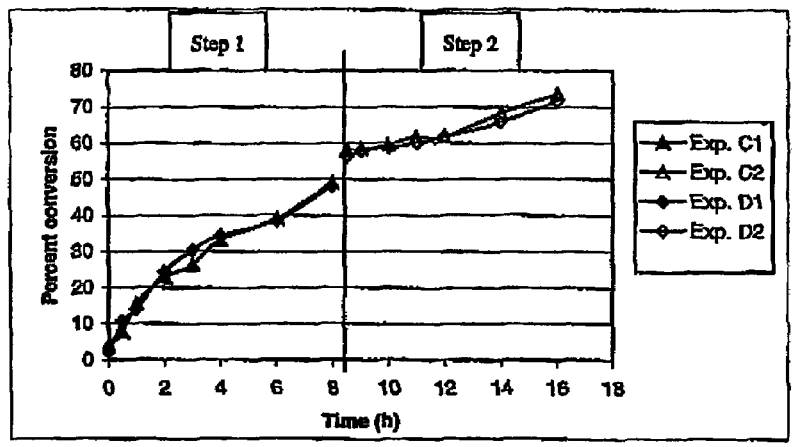
FIG. 48 is a graph illustrating percent conversion of protein to the liquid phase as a function of time for hair hydrolysis with two steps in series.

Table 111 shows the total nitrogen content in the centrifuged liquid sample as a function of time for the different experimental conditions. On the basis of the average TKN for air-dried hair (14.73%), the protein hydrolysis conversions were estimated and given in Table 112. FIG. 48 shows the total conversion for the process (Step 1+Step 2) as a function of time.

TABLE 111

Total Kjeldhal nitrogen content in the centrifuged liquid phase as a function of time for Experiment 5 (cow hair)

| Time (h) | Exp. C1 | Exp. C2 | Exp. D1 | Exp. D2 |
|---|---|---|---|---|
| 0 | 0.0241 | 0.0363 | 0.0133 | 0.0365 |
| 0.5 | 0.0454 | 0.0553 | 0.0637 | 0.0481 |
| 1 | 0.0922 | 0.0560 | 0.0822 | 0.0571 |
| 2 | 0.1350 | 0.0620 | 0.1438 | 0.0631 |
| 3 | 0.1549 | 0.0756 | 0.1792 | 0.0704 |
| 4 | 0.1951 | 0.0745 | 0.2023 | 0.0798 |
| 6 | 0.2299 | 0.1135 | 0.2269 | 0.1042 |
| 8 | 0.2887 | 0.1450 | 0.2837 | 0.1383 |

TKN in g nitrogen/100 g liquid sample.

TABLE 112

Percentage conversion of the total TKN to soluble TKN for Experiment 5 (cow hair)

| Time (h) | Exp. C1 | Exp. C2 | Exp. D1 | Exp. D2 |
|---|---|---|---|---|
| 0 | 4.09 | 6.16 | 2.26 | 6.19 |
| 0.5 | 7.71 | 9.39 | 10.81 | 8.16 |
| 1 | 15.65 | 9.50 | 13.95 | 9.69 |
| 2 | 22.91 | 10.52 | 24.41 | 10.71 |
| 3 | 26.29 | 12.83 | 30.41 | 11.95 |
| 4 | 33.11 | 12.64 | 34.33 | 18.54 |
| 6 | 39.02 | 19.26 | 38.51 | 17.68 |
| 8 | 49.00 | 24.61 | 48.15 | 23.47 |

FIG. 48 shows a similar conversion for the two conditions studied. At 16 h of treatment, a total of 70% of the initial nitrogen is recovered in the liquid phase. The total conversion increases during the second treatment and a lower concentration of ammonia is present compared to the one-step treatment (Table 113), which suggest a lower degradation of amino acids. Hence, further treatment of the residual solid with lime hydrolyzes more hair, but the concentration of nitrogen (protein/amino acids) in the second step is only 40% of the obtained in the initial treatment, which increases the energy required for water evaporation. Because the initial concentration of hair has no important effect in the conversion, a higher product concentration might be obtained with a semi-solid reaction.

TABLE 113

Total Kjeldhal nitrogen and ammonia concentration for the two-step and the one-step process

|  | Step 1 (8 h) | Step 2 (8 h) | One-Step (16 h) |
|---|---|---|---|
| TKN | 0.2984 | 0.1154 | 0.3525 |
| Ammonia | 87 | 39 | 363 |

The separation of the initial liquid at 8 h ensures relatively high concentrations for the susceptible amino acids (arginine, threonine, and serine) with approximately 50% conversion of the initial protein. The second step gives a higher total conversion with lower concentrations of these amino acids.

The unreacted residual solid after Step 2 (approximately 30% of the initial hair with 7 g nitrogen/100 g dry solid) could be further treated to give a total of 80% protein recovery in the liquid phase. This step will probably require between 24 and 36 hours.

Experiment 6

Amino Acid Composition of Products and Process Mass Balance

This section presents the total mass balance and the amino acid composition of the products obtained with the suggested two 8-h step process and the one 16-h step treatment.

Figure 49:
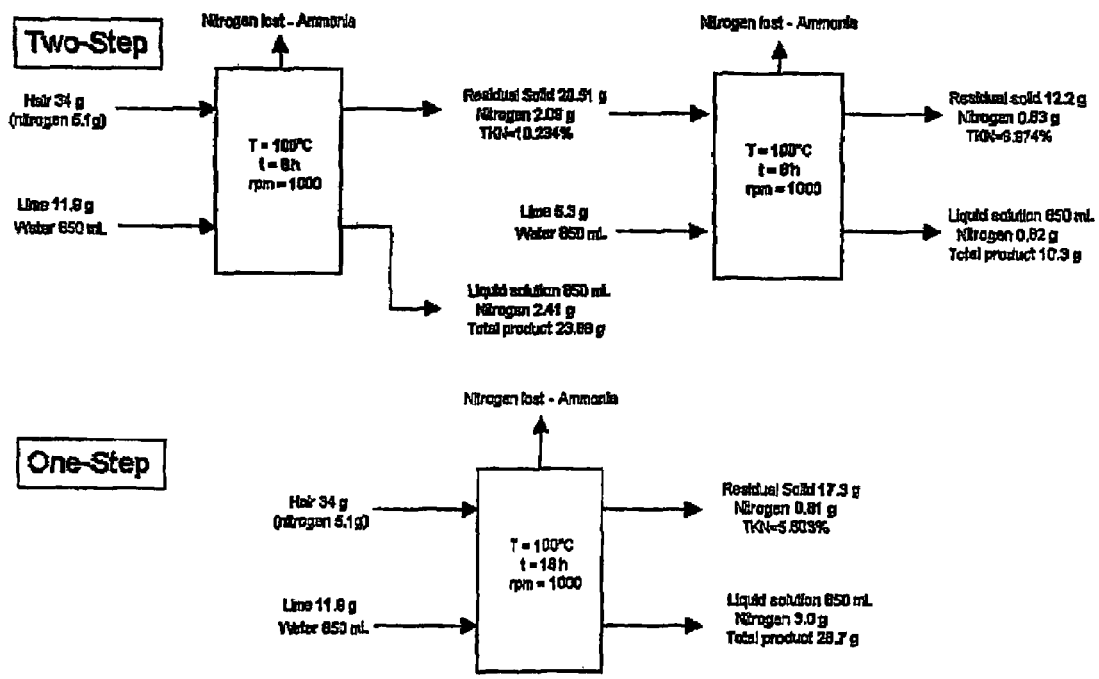
FIG. 49 shows the mass balance of two-step and one-step lime treatment processes.
Figure 50:
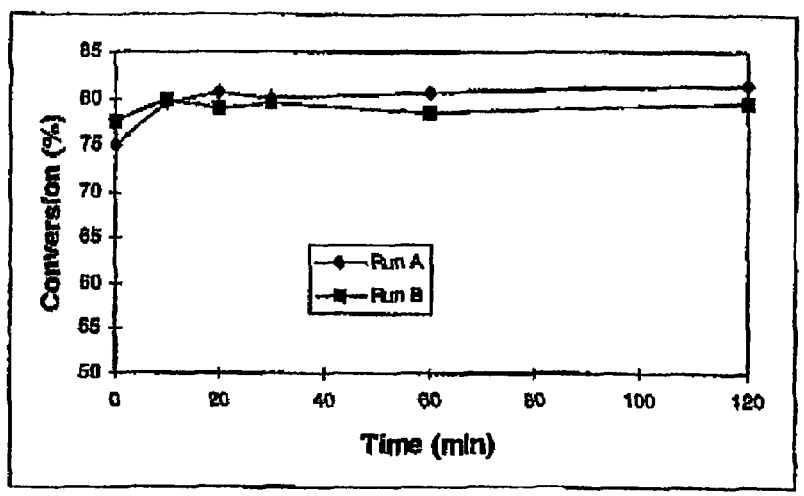
FIG. 50 is a graph illustrating repeatability of protein solubilization of shrimp head waste.

Table 113 compares the total Kjeldhal nitrogen and the ammonia concentration for the three centrifuged liquid products. Table 114 shows the solid composition (nitrogen and minerals) for the three residual solids. FIG. 49 shows the mass balance for the two-step process and the one-step process. Non-homogeneity in solids produces very high variation in concentrations.

TABLE 114

Protein and mineral content of air-dried hair and residual solids of the process

| Sample | TKN (%) | P (%) | K (%) | Ca (%) | Mg (%) | Na (ppm) | Zn (ppm) | Fe (ppm) | Cu (ppm) | Mn (ppm) |
|---|---|---|---|---|---|---|---|---|---|---|
| Hair | 14.73 | 0.0508 | 0.0197 | 0.1658 | 0.029 | 5244 | 58 | 185 | 50 | 37 |
| RS1 8 h | 10.234 | 0.0622 | 0.0176 | 7.0083 | 0.1233 | 3005 | 108 | 457 | 61 | 17 |
| RS2 8 h | 6.974 | 0.0725 | 0.0155 | 10.1003 | 0.1938 | 2301 | 117 | 702 | 62 | 22 |
| RS3 16 h | 5.803 | 0.0642 | 0.0228 | 9.7181 | 0.1617 | 2404 | 79 | 472 | 56 | 18 | nine, arginine, and serine. With the exception of the previously mentioned amino acids, the concentration of the product from Step I, Step 2, and the one-step process are very similar.

TABLE 115

Individual amino acid present in solid products and the starting material

| Amino acid | Step 1 (8 h) | Step 2 (8 h) | One-Step (16 h) | Hair |
|---|---|---|---|---|
| ASP | 8.19 | 8.68 | 7.85 | 6.63 |
| GLU | 17.46 | 19.30 | 17.51 | 14.47 |
| SER | 3.01 | 1.10 | 1.57 | 8.91 |
| HIS | 1.06 | 0.83 | 0.94 | 1.29 |
| GLY | 10.00 | 6.97 | 9.84 | 5.52 |
| THR | 1.32 | 0.83 | 0.76 | 7.48 |
| ALA | 7.34 | 7.80 | 8.64 | 4.50 |
| ARG | 7.95 | 4.94 | 5.25 | 10.98 |
| TYR | 1.75 | 2.14 | 2.59 | 2.44 |
| VAL | 7.82 | 8.99 | 8.20 | 6.80 |
| MET | 0.73 | 0.99 | 0.75 | 0.71 |
| PHE | 3.37 | 3.39 | 3.38 | 3.09 |
| ILE | 4.62 | 5.21 | 4.82 | 4.20 |
| LEU | 11.01 | 13.04 | 11.52 | 9.77 |
| LYS | 2.77 | 4.82 | 3.91 | 5.53 |
| PRO | 11.62 | 10.94 | 12.45 | 7.68 |

Values in g AA/100 g total amino acids.

Table 115 compares the amino acid composition for the three different products and the hair. As expected from previous experiments, Step 1 gives the higher values for threo- Finally, in Table 116, the amino acid composition of the products was compared to the needed essential amino acids of various monogastric domestic animals.

TABLE 116

Amino acid analysis of product and essential amino acids requirements for various domestic animals

| Amino Acid | Step 1 (8 h) | Step 2 (8 h) | One-Step 16 h | Hair | Catfish | Dogs | Cats | Chickens | Pigs |
|---|---|---|---|---|---|---|---|---|---|
| ASP | 8.19 | 8.68 | 7.85 | 6.63 | | | | | |
| GLU | 17.46 | 19.30 | 17.51 | 14.47 | | | | | |
| SER | 3.01 | 1.10 | 1.57 | 8.91 | | | | | |
| HIS | 1.06 | 0.83 | 0.94 | 1.29 | 1.31 | 1 | 1.03 | 1.4 | 1.25 |
| GLY | 10.00 | 6.97 | 9.84 | 5.52 | | | | | |
| THR | 1.32 | 0.83 | 0.76 | 7.48 | 1.75 | 2.64 | 2.43 | 3.5 | 2.5 |

TABLE 116-continued

Amino acid analysis of product and essential amino acids requirements for various domestic animals

| Amino Acid | Step 1 (8 h) | Step 2 (8 h) | One-Step 16 h | Hair | Catfish | Dogs | Cats | Chickens | Pigs |
|---|---|---|---|---|---|---|---|---|---|
| ALA | 7.34 | 7.80 | 8.64 | 4.50 | | | | | |
| ARG | 7.95 | 4.94 | 5.25 | 10.98 | 3.75 | 2.82 | 4.17 | 5.5 | 0 |
| VAL | 7.82 | 8.99 | 8.20 | 6.80 | 2.63 | 2.18 | 2.07 | 4.15 | 2.67 |
| CYS | ND | ND | ND | ND | 2$^+$ | 2.41$^+$ | 3.67$^+$ | 4$^+$ | 1.92$^+$ |
| MET | 0.73 | 0.99 | 0.75 | 0.71 | 2$^+$ | 2.41$^+$ | 2.07 | 2.25 | 1.92$^+$ |
| TYR | 1.75 | 2.14 | 2.59 | 2.44 | 4.38* | 4.05* | 2.93* | 5.85* | 3.75* |
| PHE | 3.37 | 3.39 | 3.38 | 3.09 | 4.38* | 4.05* | 1.4 | 3.15 | 3.75* |
| ILE | 4.62 | 5.21 | 4.82 | 4.20 | 2.28 | 2.05 | 1.73 | 3.65 | 2.5 |
| LEU | 11.01 | 13.04 | 11.52 | 9.77 | 3.06 | 3.27 | 4.17 | 5.25 | 2.5 |
| LYS | 2.77 | 4.82 | 3.91 | 5.53 | 4.47 | 3.5 | 4 | 5.75 | 3.58 |
| TRP | ND | ND | ND | ND | 0.44 | 0.91 | 0.83 | 1.05 | 0.75 |
| PRO | 11.62 | 10.94 | 12.45 | 7.68 | | | | | |

$^+$Cysteine + methionine
*Tyrosine + phenylalanine
ND Not determined
All values are in g amino acid/100 g protein.

As shown in Table 116, the amino acid composition of lime-hydrolyzed cow hair is not well balanced with respect to the essential amino acid requirements of different domestic monogastric animals. There are particularly low values for histidine (underestimated in the analysis), threonine, methionine, and lysine some other amino acids are sufficient for the majority of animals, but not all (tyrosine, phenylalanine). Lime hydrolysis, of cow hair generates a product that is very rich in proline and glutamine+glutamate, but these are not essential amino acids in the diet of domestic monogastric animals. The amino acid product can be used for ruminants.

A higher serine and threonine concentration could be obtained by reducing the time in Step 1.

Air-dried cow hair, containing 92% protein (wet basis), can be used to obtain an amino acid-rich product by treating with Ca(OH)$_2$ at 100° C. A simple non-pressurizing vessel can be used for the above process due to the low temperature requirements.

Hair concentration has no important effect on protein hydrolysis, whereas high lime loadings (greater than 0.1 g Ca(OH)$_2$/g hair) and long treatment periods (t>8 h) are required to obtain conversions of about 70%, which also can be obtained from chicken feathers, another keratin material.

Protein solubilization varies with lime loading only for the long-term treatment, showing that the hydroxyl group is required as a catalyst for the hydrolysis reaction, but its consumption during the process makes the lower lime loading reaction slow down or level off faster.

The optimal conditions to maximize protein conversion (up to 70%) are 0.35 g Ca(OH)$_2$/g air-dried hair processed at 100° C. for at least 24 hours. A very perceptible ammonia odor, starting at 24 hours, suggests amino acid degradation. Arginine, threonine and serine are the more susceptible amino acids under alkaline hydrolysis.

Degradation of amino acids can be minimized by recovering the amino acids already hydrolyzed into the liquid phase, with separation of residual solids for further alkaline hydrolysis in subsequent treatment steps. The separation of the initial liquid (Step 1) at 8 h ensures relatively high concentrations for the susceptible amino acids (arginine, threonine, and serine) with approximately 50% conversion of the initial protein. The second 8-h step gives a higher total conversion (approximately 70%) with lower concentrations of these amino acids.

Nitrogen concentration (protein/amino acids) in Step 2 is only 40% of that obtained in the initial treatment, which increases the energy required for water evaporation. Because the initial concentration of hair has no important effect in the conversion, a higher product concentration might be obtained with a semi-solid reaction.

The amino acid composition of the product compares poorly with the essential amino acid requirements for various domestic monogastric animals. The product is low in threonine, histidine, methionine, and lysine. It is especially rich in asparagine and proline, but these are not required in animal diets. The products obtained by this process are valuable as ruminant feed, have a very high digestibility, a high nitrogen content, and are highly soluble in water.

Example 7

Protein Solubilization in Shrimp Heads

Considerable amounts of shrimp processing by-products are discarded each year. In commercial shrimp processing about 25% (w/w) of the live shrimp is recovered as meat. The solid waste contains about 30-35% tissue protein; calcium carbonate and chitin are the other major fractions. Chitin and chitosan production are currently based on waste from crustacean processing. During chitosan production, for every kg of chitosan produced, about 3 kg of protein are wasted (Gildberg and Stenberg, 2001).

Chitin is a widely distributed, naturally abundant amino polysaccharide, insoluble in water, alkali, and organic solvents, and slightly soluble in strong acids. Chitin is a structural component in crustacean exoskeletons, which are ~15-20% chitin by dry weight. Chitin is similar to cellulose both in chemical structure and in biological function as a structural polymer (Kumar, 2000).

At the present time, chitin-containing materials (crab shell, shrimp waste, etc.) are treated in boiling aqueous sodium hydroxide (4% w/w) for 1-3 h followed by decalcification (calcium carbonate elimination) in diluted hydrochloric acid (1-2 N HCL) for 8-10 h. Then chitin is deacetylated to become chitosan in concentrated sodium hydroxide (40-50% w/w) under boiling temperature.

Frozen large whole white shrimps were obtained from the grocery store. Shrimp tails were removed and the residual waste (heads, antennae, etc.) was blended for 10 min in an industrial blender, collected in plastic bottles and finally frozen at −4° C. for later use. Samples of this blended material were used to obtain the moisture content, the total nitrogen (estimate of the protein ~16%+chitin fraction ~16.4% of total weight is nitrogen), the ash (mineral fraction), and the amino acid content to characterize the starting material.

Shrimp head waste was 21.46% dry material and 17.2 g ash/100 g dry weight (Table 117 and Table 118). The TKN was 10.25% corresponding to a crude protein and chitin fraction of about 64.1% (Table 119). The remaining 18% corresponds to lipids and other components. The amino acid composition for shrimp head waste is given in Table 120.

TABLE 117

Moisture content in shrimp head waste

| Sample | Solid (g) | Dry Solid (g) | Dry solid (%) |
|---|---|---|---|
| 1 | 64.1091 | 13.7745 | 21.49 |
| 2 | 58.5237 | 12.5662 | 21.47 |
| 3 | 61.7193 | 13.2126 | 21.41 |
|  |  | Mean | 21.46 |

TABLE 118

Ash content in shrimp head waste

| Sample | Solid (g) | Dry Solid (g) | Dry solid (%) |
|---|---|---|---|
| 1 | 3.2902 | 0.5859 | 17.81 |
| 2 | 3.068 | 0.5148 | 16.78 |
| 3 | 3.0486 | 0.5196 | 17.04 |
|  |  | Mean | 17.21 |

TABLE 119

Protein and mineral content in shrimp head waste

| Sample | TKN (%) | P (%) | K (%) | Ca (%) | Mg (%) | Na (ppm) | Zn (ppm) | Fe (ppm) | Cu (ppm) | Mn (ppm) |
|---|---|---|---|---|---|---|---|---|---|---|
| 1 | 10.2 | 1.34 | 1.07 | 4.5430 | 0.3896 | 12090 | 90 | 355 | 160 | 10 |
| 2 | 10.3 | 1.21 | 1.02 | 4.7162 | 0.3586 | 11550 | 90 | 167 | 155 | 9 |
| Mean | 10.25 | 1.27 | 1.045 | 4.6296 | 0.3781 | 11820 | 90 | 261 | 157.5 | 95 |

TABLE 120

Amino acid composition of shrimp head waste

| Amino acid | Measured | Amino acid | Measured |
|---|---|---|---|
| ASP | 11.13 | TYR | 3.15 |
| GLU | 15.83 | VAL | 5.77 |
| SER | 4.08 | MET | 1.84 |
| HIS | 1.78 | PHE | 4.93 |
| GLY | 6.94 | ILE | 4.54 |
| THR | 4.06 | LIEU | 8.30 |
| ALA | 6.83 | LYS | 5.63 |
| OYS | ND | TRIP | ND |
| ARG | 7.25 | PRO | 7.96 |

ND: Not determined
Values in g AA/100 g total amino acids.

The starting material contains a well-balanced amino acid content (Table 120); with relatively low levels of histidine and methionine. High levels of phosphorous, calcium, potassium make the material a valuable source for minerals in animal diets.

Experiment 1

Repeatability

To determine the repeatability of the solubilization process of protein in shrimp head waste, two experiments were run under the same conditions (100° C., 40 g dry shrimp/L, and 0.10 g lime/g dry shrimp respectively). The experimental conditions and variables measured are summarized in Table 121.

TABLE 121

Experimental conditions and variables measured for determining the repeatability in protein solubilization of shrimp head waste

| Experiment | A | B |
|---|---|---|
| Mass of shrimp head waste (g) | 149 | 149 |
| Volume of water (mL) | 750 | 750 |
| Mass of lime (g) | 3.2 | 3.2 |
| Initial temperature (° C.) | 97 | 87 |
| pH final | 10.64 | 10.2 |
| Humid residual solid (g) | 137.19 | 182.7 |
| Dry residual solid (g) | 17.24 | 19.74 |
| Dissolved solids in 100 mL (g) | 2.3757 | 2.4322 |

Table 22 shows the total nitrogen content in the centrifuged liquid samples as a function of time for the two different runs. On the basis of the average TKN for dry shrimp head wastes (10.25%), the protein hydrolysis conversions were estimated and given in Table 123. The average standard deviation for the conversion values is 1.13 or 1.5% of the average result (79.3% conversion).

TABLE 122

Total Kjeldhal nitrogen content in the centrifuged liquid phase as a function of time for Experiment 1 (shrimp head waste)

| Time (min) | A | B |
|---|---|---|
| 0 | 0.2837 | 0.2934 |
| 10 | 0.3005 | 0.3017 |
| 20 | 0.3053 | 0.2981 |
| 30 | 0.3029 | 0.3005 |
| 60 | 0.3053 | 0.2969 |
| 120 | 0.3077 | 0.3005 |

TKN in g nitrogen/100 g liquid sample.

TABLE 123

Percentage conversion of the total TKN to soluble TKN for Experiment 1 (shrimp head waste)

| Time (min) | A | B |
|---|---|---|
| 0 | 75.1 | 77.6 |
| 10 | 79.5 | 79.8 |
| 20 | 80.8 | 78.9 |
| 30 | 80.1 | 79.5 |
| 60 | 80.8 | 78.6 |
| 120 | 81.4 | 79.5 |

FIG. 49 presents the protein solubilization (percentage conversion) as a function of time for the two different runs. It shows that the conversion remains constant after the initial 5-10 min, and that the protein hydrolysis process is fairly repeatable under the conditions studied. For the sample for time 0 min, is taken after the reactor is closed and pressurized, this process takes between 8 and 12 min.

Experiment 2

Temperature Effect

To determine the effect of temperature on solubilizing protein in shrimp head waste, experiments were run at different temperatures keeping the lime loading and material concentration constant (0.10 g lime/g shrimp and 40 g dry shrimp/L respectively). The experimental conditions and variables measured are summarized in Table 124.

TABLE 124

Experimental conditions and variables measured to determine the effect of temperature in protein solubilization of shrimp head waste

| | Temperature (° C.) | | |
|---|---|---|---|
| | 75 | 100 | 125 |
| Mass of shrimp (g) | 149 | 149 | 149 |
| Volume of water (mL) | 750 | 750 | 750 |
| Mass of lime (g) | 3.2 | 3.2 | 3.2 |
| Initial temperature (° C.) | 78.5 | 97 | 108 |
| pH final | 10.1 | 10.64 | 9.88 |
| Humid residual solid (g) | 133.04 | 137.19 | 130.58 |
| Dry residual solid (g) | 16.06 | 17.24 | 17.42 |
| Dissolved solids in 100 mL (g) | 2.6439 | 2.3757 | 2.6808 |

Table 125 shows the total nitrogen content in the centrifuged liquid samples as a function of time for the different temperatures. On the basis of the average TKN for dry shrimp head waste (10.25%), the protein hydrolysis conversions were estimated and given in Table 126.

TABLE 125

Total Kjeldhal nitrogen content in the centrifuged liquid phase as a function of time for Experiment 2 (shrimp head waste)

| | Temperature | | |
|---|---|---|---|
| Time (min) | 75° C. | 100° C. | 125° C. |
| 0 | 0.3160 | 0.2837 | 0.3053 |
| 10 | 0.3196 | 0.3005 | 0.3101 |
| 20 | 0.3101 | 0.3053 | 0.3101 |
| 30 | 0.3101 | 0.3029 | 0.3112 |
| 60 | 0.3101 | 0.3053 | 0.3101 |
| 120 | 0.3172 | 0.3077 | 0.3101 |

TKN in g nitrogen/100 g liquid sample.

TABLE 126

Percentage conversion of the total TKN to soluble TKN for Experiment 2 (shrimp head waste)

| | Temperature | | |
|---|---|---|---|
| Time (min) | 75° C. | 100° C. | 125° C. |
| 0 | 83.6 | 75.1 | 80.8 |
| 10 | 84.6 | 79.5 | 82.1 |
| 20 | 82.1 | 80.8 | 82.1 |
| 30 | 82.1 | 80.1 | 82.3 |
| 60 | 82.1 | 80.8 | 82.1 |
| 120 | 83.9 | 81.4 | 82.1 |

Figure 51:
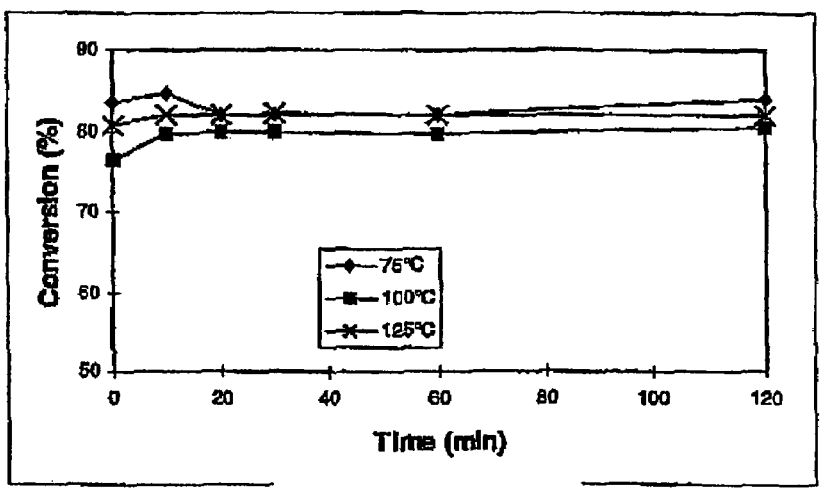
FIG. 51 is a graph illustrating temperature effect on protein solubilization of shrimp head waste.

FIG. 51 presents the protein hydrolysis (percentage conversion) as a function of time for the different temperatures studied. The conversion does not depend on temperature (statistically the same value). The lower temperature is favored because the amino acids Should degrade less, and the energy required to keep the process at this temperature is also less.

Experiment 3

Lime Loading Effect I

To determine the effect of lime loading on protein solubilization of shrimp head waste, experiments were run at different lime/shrimp ratios keeping the temperature and shrimp concentration constant (100° C. and 40 g dry shrimp/L respectively). The experimental conditions and variables measured are summarized in Table 127.

TABLE 127

Experimental conditions and variables measured to determine the lime loading effect in protein solubilization of shrimp head waste

| | Lime loading (g lime/g shrimp) | | | |
|---|---|---|---|---|
| | 0 | 0.05 | 0.1 | 0.2 |
| Mass of shrimp head waste (g) | 149 | 149 | 149 | 149 |
| Volume of water (mL) | 750 | 750 | 750 | 750 |
| Mass of lime (g) | 0 | 1.6 | 3.2 | 6.4 |
| Initial Temperature (° C.) | 96 | 95 | 97 | 103 |
| pH final | 8.1 | 9.20 | 10.64 | 12 |
| Humid residual solid (g) | 179.4 | 148.8 | 137.2 | 122.5 |
| Dry residual solid (g) | 17.72 | 16.5 | 17.24 | 18.28 |
| Dissolved solids in 100 mL (g) | 2.3576 | 2.5146 | 2.3757 | 2.4516 |

Table 128 shows the total nitrogen content in the centrifuged liquid samples as a function of time for the different lime loadings. On the basis of the average TKN for dry shrimp head waste (10.25%), the protein hydrolysis conversions were estimated (Table 129).

TABLE 128

Total Kjerahl nitrogen content in the centrifuged liquid phase as a function of time for Experiment 3 (shrimp head waste)

| Time (min) | Lime loading | | | |
|---|---|---|---|---|
| | 0 g/g | 0.05 g/g | 0.1 g/g | 0.2 g/g |
| 0 | 0.2477 | 0.2890 | 0.2837 | 0.2573 |
| 10 | 0.2452 | 0.2978 | 0.3005 | 0.2573 |
| 20 | 0.244 | 0.3035 | 0.3053 | 0.2621 |
| 30 | 0.2488 | 0.3035 | 0.3029 | 0.2669 |
| 60 | 0.2452 | 0.3051 | 0.3053 | 0.2766 |
| 120 | 0.2513 | 0.3035 | 0.3077 | 0.2897 |

TKN in g nitrogen/100 g liquid sample.

TABLE 129

Percentage conversion of the total TKN to soluble TKN for Experiment 3 (shrimp head waste)

| Time (min) | Lime loading | | | |
|---|---|---|---|---|
| | 0 g/g | 0.05 g/g | 0.1 g/g | 0.2 g/g |
| 0 | 65.5 | 76.5 | 76.4 | 68.1 |
| 10 | 64.9 | 78.8 | 79.7 | 68.1 |
| 20 | 64.6 | 80.3 | 79.8 | 69.4 |
| 30 | 65.8 | 80.3 | 79.8 | 70.6 |
| 60 | 64.9 | 80.7 | 79.7 | 73.2 |
| 120 | 66.5 | 80.3 | 80.5 | 76.7 |

Figure 52:
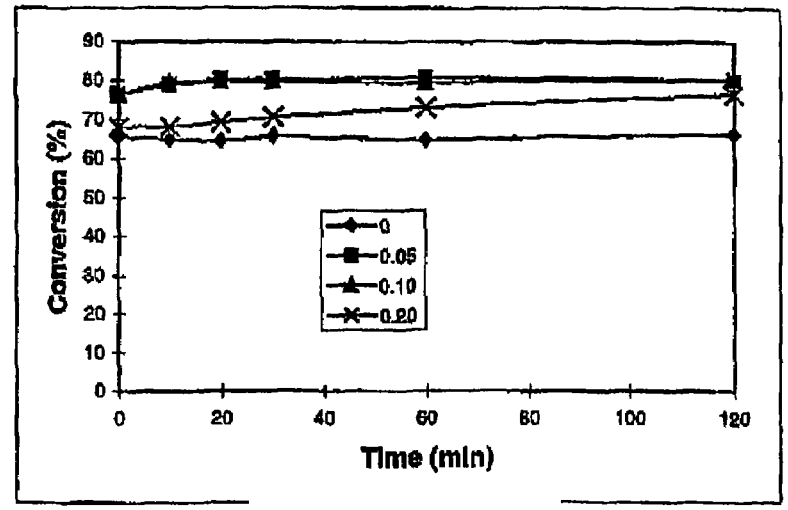
FIG. 52 is a graph illustrating lime loading effect on protein solubilization of shrimp head waste.

FIG. 52 presents the protein solubilized (percentage conversion) as a function of time for the different lime loadings studied. It shows that the conversion is similar for all lime loadings, except for the experiment with no lime (statistically different).

In the no-lime experiment, there is soluble protein present in the water phase; however, hydroxyl groups are dilute, making the hydrolysis reaction and cell breakage slow-down. The final pH for the no-lime experiment was 8.1. Likely, the alkaline pH is caused by the calcium carbonate and bicarbonate released from the shrimp waste.

The addition of lime is required to ensure fast protein hydrolysis into the liquid phase, and would likely give a higher fraction of free amino acids in the product. Also, because the lime treatment is considered as a preliminary step for generating chitin and chitosan, a high protein recovery is related to reducing chemicals required for subsequent steps during processing, and a higher quality chitin or chitosan product.

The recovery of carotenoids (astaxanthin) from the suspended solids could be considered for generating an additional valuable product from the process. Because calcium carbonate and chitin are structural components in the crustacean, straining the mixture and centrifuging the suspended solids could recover carotenoids (Gildberg and Stenberg, 2001).

Experiment 4

Amino Acid Analysis

Table 130 shows the total amino acid composition of the hydrolyzate for different process conditions. With the exception of serine and threonine in the high-lime-loading experiment, and a relatively high variation in the cysteine content, the composition of the final product does not vary with the treatment conditions. As shown in previous results, the no-lime experiment produces a lower protein concentration in the hydrolyzate.

TABLE 130

Total amino acid composition with different process conditions protein hydrolysis of shrimp head waste

| Conditions | 100° C. 60 min 0.1 lime | 100° C. 120 min 0.2 lime | 100° C. 120 min 0.1 lime | 100° C. 120 min No lime | 75° C. 120 min 0.1 lime | 125° C. 120 min 0.1 lime |
|---|---|---|---|---|---|---|
| ASP | 9.66 | 10.19 | 9.27 | 9.78 | 9.46 | 9.40 |
| GLU | 15.68 | 15.85 | 15.50 | 15.68 | 15.03 | 15.20 |
| SER | 4.57 | 3.92* | 4.33 | 4.46 | 4.41 | 4.38 |
| HIS | 0.00 | 0.00 | 0.00 | 0.00 | 0.00 | 0.00 |
| GLY | 7.77 | 8.31 | 7.32 | 7.26 | 7.05 | 7.42 |
| THR | 3.57 | 2.30* | 4.01 | 4.46 | 4.40 | 3.77 |
| ALA | 7.15 | 7.53 | 7.28 | 7.20 | 6.69 | 7.17 |
| TAU | 0.00 | 0.00 | 0.00 | 0.00 | 0.00 | 0.00 |
| ARG | 7.00 | 6.47 | 7.59 | 4.90* | 7.94 | 6.60 |
| TYR | 3.82 | 4.27 | 3.78 | 3.94 | 3.83 | 4.13 |
| CYS—CYS | 0.67 | 0.48 | 0.82 | 1.42 | 1.09 | 0.74 |
| VAL | 5.79 | 6.13 | 6.08 | 6.17 | 6.24 | 6.30 |
| MET | 2.19 | 2.15 | 2.21 | 2.25 | 2.15 | 2.14 |
| TRP | ND | ND | ND | ND | ND | ND |
| PHE | 4.43 | 4.90 | 4.43 | 4.67 | 4.57 | 4.81 |
| ILE | 4.01 | 4.32 | 4.31 | 4.30 | 4.33 | 4.51 |
| LEU | 8.60 | 8.94 | 8.75 | 9.02 | 8.83 | 8.97 |
| LYS | 7.79 | 7.31 | 7.34 | 7.52 | 7.53 | 7.59 |
| PRO | 7.30 | 6.92 | 6.97 | 6.97 | 6.45 | 6.85 |

ND: Not determined
Values in g AA/100 g total amino acids.

Table 131 shows the free amino acid composition of the hydrolyzate for different process conditions. The composition variability is higher than in the total amino acids case. Treatment conditions affect susceptible amino acids; stronger conditions (e.g., longer times, higher temperatures, or higher lime loadings) accelerate the degradation reactions and generate different compositions, especially in the free amino acid determination.

Tryptophan represents approximately 2% of the free amino acid composition, whereas taurine is close to 4%. These values can be used as estimates for their concentrations in the total amino acid composition.

TABLE 131

Free amino acid composition with different process conditions for protein hydrolysis of shrimp head waste

| Conditions | 100° C. 60 min 0.1 lime | 100° C. 120 min 0.2 lime | 100° C. 120 min 0.1 lime | 100° C. 120 min No lime | 75° C. 120 min 0.1 lime | 125° C. 120 min 0.1 lime |
|---|---|---|---|---|---|---|
| ASP | 1.61 | 3.85 | 2.09 | 2.93 | 216 | 2.75 |
| GLU | 3.49 | 5.54 | 3.86 | 4.46 | 4.08 | 4.20 |
| ASN | 1.87 | 0.83 | 2.15 | 2.40 | 2.53 | 2.12 |
| SER | 3.01 | 4.15 | 3.17 | 3.37 | 3.20 | 3.59 |
| GLN | 1.67 | 0.00 | 2.05 | 2.69 | 3.29 | 0.18 |
| HIS | 0.00 | 0.00 | 0.00 | 0.00 | 0.00 | 0.00 |
| GLY | 8.51 | 8.61 | 6.55 | 6.54 | 5.80 | 6.59 |
| THR | 2.44 | 1.38 | 3.00 | 3.38 | 3.25 | 2.91 |
| CIT | 0.52 | 1.13 | 0.58 | 0.38 | 0.67 | 0.36 |
| B-ALA | 0.50 | 0.25 | 0.09 | 0.02 | 0.00 | 0.15 |
| ALA | 8.71 | 9.21 | 8.41 | 8.45 | 7.85 | 8.98 |
| TAU | 6.51 | 5.63 | 4.31 | 3.84 | 3.48 | 3.95 |
| ARG | 11.45 | 9.37 | 11.63 | 6.53 | 11.46 | 9.51 |
| TYR | 3.93 | 4.35 | 4.72 | 5.40 | 5.06 | 5.25 |
| CYS—CYS | ND | ND | ND | ND | ND | ND |
| VAL | 4.10 | 4.61 | 4.84 | 4.87 | 4.85 | 5.50 |
| MET | 2.78 | 3.22 | 3.22 | 3.36 | 3.01 | 2.89 |
| TRP | 2.78 | 2.57 | 2.32 | 2.17 | 2.16 | 1.86 |
| PHE | 4.55 | 4.74 | 5.17 | 6.15 | 5.87 | 5.56 |
| ILE | 3.86 | 3.92 | 4.82 | 4.32 | 4.45 | 5.72 |

TABLE 131-continued

Free amino acid composition with different process conditions for protein hydrolysis of shrimp head waste

| Conditions | 100° C. 60 min 0.1 lime | 100° C. 120 min 0.2 lime | 100° C. 120 min 0.1 lime | 100° C. 120 min No lime | 75° C. 120 min 0.1 lime | 125° C. 120 min 0.1 lime |
|---|---|---|---|---|---|---|
| LEU | 7.63 | 8.15 | 8.90 | 9.82 | 9.60 | 9.75 |
| LYS | 10.31 | 9.39 | 9.82 | 10.98 | 9.32 | 9.82 |
| PRO | 9.78 | 9.10 | 8.28 | 7.95 | 7.91 | 8.37 |

ND: Not determined
Valves in g AA/100 g total free amino acids.

An average of 40% of the total amino acids is present as free amino acids. A relatively higher fraction is obtained for longer times or stronger conditions.

The thermo-chemical treatment of shrimp waste produces a mixture of free. amino acids and small soluble peptides) making it a potential nutritious product. The hydrolyzate product contains a high :fraction of essential amino acid) making it a high quality nutritional source for monogastric animals. Table 132 shows a comparison between the total amino acid composition and the requirement for various domestic animals. Because histidine is underestimated during the analysis, and using the 1.78 g/100 g value calculated for the raw waste material, a high quality protein supplement is generated that meets or exceed the essential amino acids requirements of the animals during their growth phase.

TABLE 132

Amino acid analysis of product and essential amino acids requirements for various domestic animals (shrimp head waste)

| Amino Acid | Catfish | Dogs | Cats | Chickens | Pigs | Liquid (TAA) | Liquid (FAA) |
|---|---|---|---|---|---|---|---|
| ASN | | | | | | | 2.15 |
| GLN | | | | | | | 2.05 |
| ASP | | | | | | 9.27 | 2.09 |
| GLU | | | | | | 15.50 | 3.86 |
| SER | | | | | | 4.33 | 3.17 |
| HIS | 1.31 | 1.00 | 1.03 | 1.40 | 1.26 | 0.00 | 0.00 |
| GLY | | | | | | 7.32 | 6.55 |
| THR | 1.75 | 2.64 | 2.43 | 3.50 | 2.50 | 4.01 | 3.00 |
| ALA | | | | | | 7.28 | 8.41 |
| ARG | 3.75 | 2.82 | 4.17 | 5.50 | 0.00 | 7.59 | 11.63 |
| VAL | 2.63 | 2.18 | 2.07 | 4.15 | 2.67 | 6.08 | 4.48 |
| CYS | 2.00* | 2.41* | 3.67* | 4.00* | 1.92* | 0.82 | ND |
| MET | 2.00* | 2.41* | 2.07 | 2.25 | 1.92* | 2.21 | 3.22 |
| TYR | 4.38+ | 4.05+ | 2.93+ | 5.85+ | 3.75+ | 3.78 | 4.72 |
| PHE | 4.38+ | 4.05+ | 1.40 | 3.15 | 3.75+ | 4.43 | 5.17 |
| ILE | 2.28 | 2.05 | 1.73 | 3.65 | 2.50 | 4.31 | 4.82 |
| LEU | 3.06 | 3.27 | 4.17 | 5.25 | 2.50 | 8.75 | 8.90 |
| LYS | 4.47 | 3.50 | 4.00 | 5.75 | 3.58 | 7.34 | 9.92 |
| TRP | 0.44 | 0.91 | 0.83 | 1.05 | 0.75 | ND | 2.32 |
| PRO | | | | | | 6.97 | 8.28 |

*Cysteine + Methionine
+Tyrosine + Phenylalanine
ND Not determined
All values are in g amino acid/100 g protein.

In addition to ~20% ash, shrimp head waste contains 64% protein plus chitin, both of which can be used to generate several valuable products. The thermo-chemical treatment of this waste with lime generates a protein-rich material with a well-balanced amino acid content that can be used as an animal feed supplement. Straining the treated mixture and centrifuging the liquid product can recover carotenoids. Finally, the residual solid rich in calcium carbonate and chitin could also be used to generate chitin and chitosan through well-known processes.

For all conditions of temperature, lime loading, and time that were studied, no significant change in conversion occurred after 30 minutes of reaction. Little amino acid degradation was observed for all these conditions and up to 2 h of treatment.

Lime addition is required during the treatment to obtain a higher nitrogen conversion to the liquid phase. This will also reduce the chemicals required for further treatment of the residual solid for chitin and chitosan production.

The product obtained by lime treating the shrimp waste material, meets or exceed the essential amino acid requirements for monogastric animals making it a suitable protein supplement.

Although only exemplary embodiments of the invention are specifically described above, it will be appreciated that modifications and variations of the invention are possible without departing from the spirit and intended scope of the invention.

The invention claimed is:

1. A recirculating method of solubilizing protein and destroying prions comprising the following steps in the following order:
    first, applying an alkali to an untreated protein source to form a slurry, wherein the alkali is added in an amount sufficient to induce hydrolysis of the protein source when the slurry is heated;
    second, heating the slurry to a temperature sufficient to allow hydrolysis of protein in the protein source to obtain a reaction liquid comprising small peptides and free amino acids, and further comprising solid residues;
    third, holding the reaction liquid at an elevated temperature between 125-250° C. for a time period sufficient to destroy prions in the reaction liquid;
    fourth, separating the solid residues from the reaction liquid;
    fifth, neutralizing the reaction liquid with acid or an acid source to produce a neutralized liquid comprising small peptides and free amino acids;
    sixth, concentrating the neutralized liquid to produce concentrated liquid comprising small peptides and free amino acids and water; and
    seventh, returning the water to the slurry before or during the heating step.

2. The method according to claim 1, further comprising grinding the protein source.

3. The method according to claim 1, wherein the alkali comprises calcium oxide.

4. The method according to claim 1, wherein the alkali comprises a compound selected from the group consisting of: magnesium oxide, magnesium hydroxide, sodium hydroxide, sodium carbonate, potassium hydroxide, ammonia, and any combinations thereof.

5. The method according to claim 1, further comprising neutralizing the ammonia produced during the heating of the slurry with an acid.

6. The method according to claim 1, further comprising separating reactive solid residues from inert solid residues in the separated solid residues.

7. The method according to claim 1, wherein the time period that the reaction liquid is held at an elevated temperature sufficient to destroy prions is between 1 second and 5 hours.

8. The method according to claim 1, further comprising separating solid residues from the neutralized liquid.

9. The method according to claim 1, wherein concentrating the neutralized liquid further comprises evaporating the neutralized liquid.

10. The method according to claim 1, wherein concentrating the neutralized liquid further comprises filtering the neutralized liquid.

11. The method according to claim 1, wherein concentrating the neutralized liquid further comprises freezing the neutralized liquid.

12. The method according to claim 1, wherein concentrating the neutralized liquid further comprises adding an immiscible amine and extracting water using the immiscible ammine.

13. The method according to claim 1, further comprising drying the concentrated liquid.

14. The method according to claim 1, further comprising producing process heat and reusing process heat.

15. The method according to claim 1, wherein the alkali comprises calcium hydroxide.

16. The recirculating method of solubilizing protein comprising the following steps in the following order:
    first, applying an alkali to a protein source to form a slurry, wherein the alkali is added in an amount sufficient to induce hydrolysis of the protein source when the slurry is heated;
    second, heating the slurry to a temperature sufficient to allow hydrolysis of protein in the protein source to obtain a reaction liquid comprising solid residues;
    third, separating the solid residues from the reaction liquid;
    fourth, neutralizing the reaction liquid with acid or an acid source to produce a neutralized liquid;
    fifth, concentrating the neutralized liquid to produce concentrated liquid and water; and
    sixth, returning the water to the slurry before or during the heating step.

17. The method according to claim 16, further comprising grinding the protein source.

18. The method according to claim 16, wherein the alkali comprises calcium oxide.

19. The method according to claim 16, wherein the alkali comprises a compound selected from the group consisting of: magnesium oxide, magnesium hydroxide, sodium hydroxide, sodium carbonate, potassium hydroxide, ammonia, and any combinations thereof.

20. The method according to claim 16, further comprising neutralizing the ammonia produced during the heating of the slurry with an acid.

21. The method according to claim 16, further comprising returning separated solid residues to the protein source.

22. The method according to claim 16, further comprising separating reactive solid residues from inert-solid residues in the separated solid residues.

23. The method according to claim 16, further comprising separating solid residues from the neutralized liquid.

24. The method according to claim 23, wherein the solid residues separated from the neutralized liquid comprise the alkali and further comprising adding the separated solid residues to the protein source.

25. The method according to claim 16, wherein concentrating the neutralized liquid further comprises evaporating the neutralized liquid.

26. The method according to claim 16, wherein concentrating the neutralized liquid further comprises filtering the neutralized liquid.

27. The method according to claim 16, wherein concentrating the neutralized liquid further comprises freezing the neutralized liquid.

28. The method according to claim 16, wherein concentrating the neutralized liquid further comprises adding an immiscible amine and extracting water using the immiscible amine.

29. The method according to claim 16, further comprising drying the concentrated liquid.

30. The method according to claim 16, further comprising producing process heat and reusing process heat.

31. The method according to claim 16, wherein the alkali comprises calcium hydroxide.

* * * * *